US007312246B2

(12) United States Patent
Hamilton et al.

(10) Patent No.: US 7,312,246 B2
(45) Date of Patent: Dec. 25, 2007

(54) PROTEOMIMETIC COMPOUNDS AND METHODS

(75) Inventors: Andrew D. Hamilton, Guilford, CT (US); Justin Ernst, San Diego, CA (US); Brendan Orner, Madison, WI (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 11/043,697

(22) Filed: Jan. 25, 2005

(65) Prior Publication Data

US 2005/0215563 A1   Sep. 29, 2005

Related U.S. Application Data

(63) Continuation of application No. 10/142,126, filed on May 8, 2002, now Pat. No. 6,858,600.

(60) Provisional application No. 60/289,640, filed on May 8, 2001.

(51) Int. Cl.
*A01N 37/10* (2006.01)
(52) U.S. Cl. .................................. 514/533
(58) Field of Classification Search ..................... None
See application file for complete search history.

(56) References Cited

U.S. PATENT DOCUMENTS 4,701,459 A    10/1987  Meanwell et al.
6,858,600 B2*  2/2005   Hamilton et al. ........... 514/183

FOREIGN PATENT DOCUMENTS

| EP | 0 933 346 A1 | 8/1999 |
| FR | 2 687 668 | 8/1993 |
| GB | 1 379 785 | 1/1975 |
| WO | WO 9804508 | 2/1998 |
| WO | WO 98/16503 | * 4/1998 |

OTHER PUBLICATIONS

Million et al, "Inhibition of the EGF-Stimulated Cellular Proliferation of ER 22 Cells by Hydroxybiphenyl Derivatives" Journal of Medicinal Chemistry, vol. 38(23), pp. 4693-4703 (1995).*
Nair, P. "Epidermal Growth Factor Receptor Family and its Role in Cancer Progression" Current Science, vol. 88(6), pp. 890-898 (Mar. 6, 2005).*
Angew. Chem. Int. Ed. 2002, vol. 41, pp. 278-281, 2002, Justin T. Ernst, Olaf Kutzki, Asim K. Debnath, Shibo Jiang, Hong Lu, and Andrew D. Hamilton.
American Chemical Society, vol. 123, No. 22, pp. 5382-5383, May 11, 2001, Brendan P, Orner, Justin T. Ernst, and Andrew Hamilton.
Agrawai and Aikhatib, Chemokine receptors: emerging opportunities for new anti-HIV therapies. Expert Opin. Ther. Targets, 5(3):303-326 (2001).
CAPLUS, DN 122:128607, also cited as Yoshida et al., Chemical & Pharmaceutical Bull., 39/5, 1157-62 (1991), Abstract.
CAPLUS DN 108: 131815, also cited as U.S.P. 4701459, CAS RN113260-0108, Abstract.
Cecil Textbook of Medicine, Simone, "Oncology", Part XIV, vol. 1, 20th Edition, p. 1004-1010 (1996).
Cecil Textbook of Medicine, Damasio, A.R., "Alzheimer's Disease and Related Dementias", Part 400, vol. 2, 20th Edition, p. 1992-1996 (1996).
Cheng, et al., Local helix content and RNA-binding activity of the N-terminal leucine-repeat region of hepatitis delta antigen, J Biomolecular MNR, 12:183-188, (1998).
Coyle et al., Alzheimer's Disease: A Disorder of Cortical Cholinergic Innervation. Science, vol. 219, pp. 1164-1168, (1983).
Debnath et al., Structure-based Identification of Small Molecule Antiviral Compounds Targeted to the gp41 Core Structure of the Hyman Immunodeficiency Virus Type 1, J. Med. Chem. 42:3203-3209, (1999).
Hong, et al., Identification of a Minimal Hydrophobic Domain in the Herpes Simplex Virus Type 1 Scaffolding Protein Which Is Required for Interaction with the Major Capsid Protein, J. Virology, Jan. pp. 533-540 (1996).
Liu and Jiang, High Throughput Screening and Characterization of HIV-1 Entry Inhibitors Targeting gp41: Theories and Techniques, Current Pharmaceutical Design, 10:1827-1843 (2004).
Lou, et al., Solution Structure of an N-Capping Peptide from the N-terminal Leucine-Repeat Region of Hepatitis Delta Antigen, Archives of Biochemistry and Biophysics, 337:219-227, (2000).
Offensperger, et al., Molecular therapeutic strategies in hepatitis B virus infection, Clin. Investig 72:737-741 (1994).
Root, et al., Protein Design of an HIV-1 Entry Inhibitor, Science, 291:884-888, (2001).
Tagat et al., Piperazine-Based CCR5 Antagonists as HIV-1 Inhibitors. I: 2(S)-Methyl Piperazine as a Key Pharmacophore Element, Biorganic & Medicinal Chemistry Letters, 11:2143-2146, (2001).
Uckun et al., Structure-Based Design of Novel Anticancer Agents, Current Cancer Drug Targets, 1:59-71, (2001).
Verani and Lusso, Chemokines as natural HIV antagonists, Curr Mol Med 2(8):691-702 (2002) (abstract).
Walters, et al., Mutation of Single Hydrophobic Residue I27, L35, F39, L58, L65, L67, or L71 in the N Terminus of VP5 Abolishes Interaction with the Scaffold Protein and Prevents Closure of Herpes Simplex Virus Type 1 Capsid Shells, Journal of Virology, 77(7):4043-4059, (2003).
Dehne et al. "Synthesis of liquid-crystalline 4,4"-bis(organo)-p-terphenyls. XP008055286, Z.Chem, 9(11):423-424, 1969.
Kobayashi et al, "Palladium complex-catalyzed carboalkoxylation of bis(chloromethyl)arenas." Journal of Molecular Catalysis, 45:91-109, 1988.
Brand et al., "Functionalized hexa-peri-hexabenzocoronenes: Stable supramolecular order by polymerization in the discotic mesophase." Chem. Mater., 12: 1638-1647, 2000.

* cited by examiner

*Primary Examiner*—Zachary C Tucker
(74) *Attorney, Agent, or Firm*—Henry D. Coleman; R. Neil Sudol; William J. Sapone

(57) ABSTRACT

The present invention relates to compounds and pharmaceutical compositions which are proteonaimetic and to methods for inhibiting the interaction of an alpha-helical protein with another protein or binding site. Methods for treating diseases or conditions which are modulated through interactions between alpha helical proteins and their binding sites are other aspects of the invention. In particular, the invention relates to treatment of viral infections using terphenyl derivatives.

1 Claim, 20 Drawing Sheets

Scheme 2

Scheme 3

Scheme 4

Scheme 6

Scheme 7

Scheme 8

Scheme 9

Scheme 10

Scheme 11

Design of the smMLCK mimetic.

```
RS20:    ARRKWQKHAVRAIGRLSS
C20W:    LRRGQILWFRNRIQTQIK
``` a    b 1-naphth    d    e
           c 2-naphth

Inhibitors of gp41 Disruption k  l  m  n

Figure G. Fluorescence polarization experiments measuring the displacement of fluorescein labelled Bak peptide from BcLxL.

Scheme 12

PROTEOMIMETIC COMPOUNDS AND METHODS

CROSS REFERENCE TO RELATED APPLICATIONS

This application is a Continuation of U.S. application Ser. No. 10/142,126, filed May 8, 2002, now U.S. Pat. No. 6,858,600 which claims priority to U.S. Provisional Application No. 60/289,640, filed May 8, 2001, from each of which priority is claimed, and each of which is hereby incorporated by reference in its entirety, including all tables, figures, and claims.

GOVERNMENT SUPPORT

The invention described herein was supported in part by grant number CA78038 from the National Institutes of Health. The government has certain rights to this invention.

FIELD OF THE INVENTION

The present invention relates to compounds and pharmaceutical compositions which are proteomimetic and to methods for inhibiting the interaction of an alpha-helical protein with another protein or binding site. Methods for treating diseases or conditions which are modulated through interactions between alpha helical proteins and their binding sites are other aspects of the invention. Methods of inhibiting the binding of proteins to their binding sites are other aspects of the present invention.

BACKGROUND OF THE INVENTION

The design of synthetic structures that mimic large and non-contiguous regions of a protein surface remains an extremely important but elusive goal.[1] There has been considerable success in the field of small peptidomimetics that reproduce features of short peptides in extended[2] or β-turn conformations.[3] However, much less progress has been made in the search for proteomimetics or non-peptide structures that mimic larger areas of the protein surface[4] such as an α-helix.[5] This is remarkable given the ubiquitous role of α-helical regions in mediating protein-protein interactions.[6] The difficulty clearly lies in the large and elongated surface area that is presented by 2-4 turns of an α-helix. One strategy involves the covalent or non-covalent stabilization of a 16-20-mer peptide in a helical conformation either through side chain contacts,[7] end capping templation,[8] specific folding[9] or use of β-peptides.[10] However, these approaches suffer the normal limitations of flexibility and instability associated with using peptide derivatives. As part of our interest in helix surface recognition,[11,12] the inventors of the present application sought an entirely non-peptidic scaffold that could be synthesized in a modular fashion and project side chain functionality with similar distance and angular relationships to those found in α-helices. One aspect of the present application, therefore, relates to a new family of proteomimetics, based on a functionalized terphenyl and related structure scaffold, that are structural mimics of two turns of the myosin light chain kinase α-helix and show functional analogy in binding with high affinity to calmodulin.

In α-helix-protein complexes critical interactions are often found along one face of the helix, involving side chains from the i, i+3, and i+7 residues.[6] The relative positions of these groups in an all-Ala α-helix have been shown and compared to the projection of substituents in a tris-functionalized 3,2',2"-terphenyl derivative.[13] This is an attractive template for proteomimetic design due to the simplicity of the structure and the potential for an iterative synthesis. The alternating arrangement of i, i+3, and i+7 groups through two turns in the helix compares well with the 3,2',2"-substituents when the terphenyl is in a staggered conformation with dihedral angles of 68° and 36° between the phenyl rings.[14] In this easily accessible conformation, the three subsituents project from the terphenyl core with similar angular relationships and 4-25% shorter distances than between the i, i+3, and i+7 β-carbons in an α-helix.[15]

OBJECTS OF THE INVENTION

It is an object of the invention of the present invention to provide novel compounds which exhibit proteomimetic characteristics, and in particular, mimic α-helical proteins.

It is another object of the invention to provide pharmaceutical compositions based upon the compounds according to the present invention which are useful to treat disease states or conditions which are modulated through the interaction of an α-helix protein with another protein or binding site for the protein.

It is still another object of the invention to provide methods for treating disease states or conditions which are modulated through the interaction of an α-helical protein with another protein or binding site for the protein.

It is yet another object of the present invention to provide a method of providing compounds which exhibit proteomimetic characteristics.

These and/or other objects of the present invention may be readily gleaned from the description of the invention which follows.

DESCRIPTION OF THE INVENTION

Figure 1:
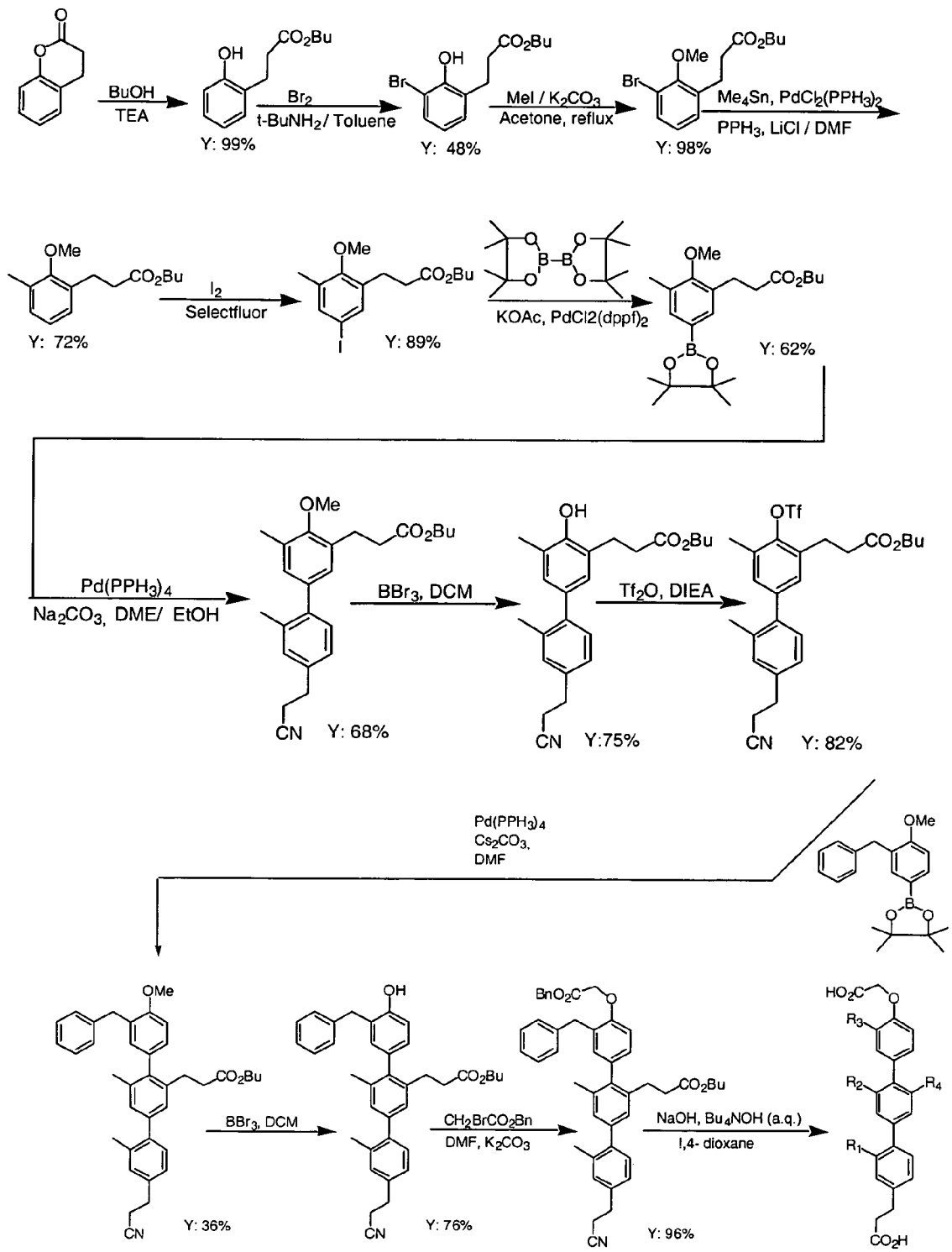
FIG. 1 shows a general chemical synthetic scheme for producing terphenyl compounds according to the present invention.

The present invention relates to compounds according to the general formula:

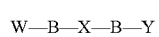

Where X is selected from the group consisting of a five or six-membered ring selected from the group consisting of

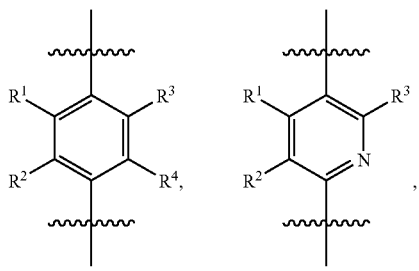
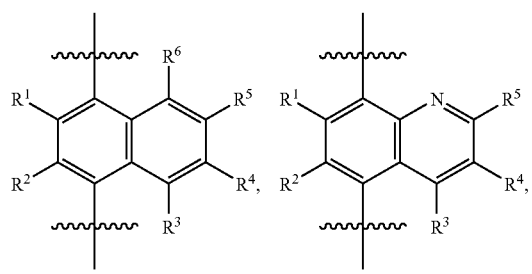
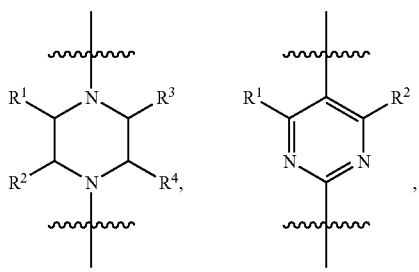
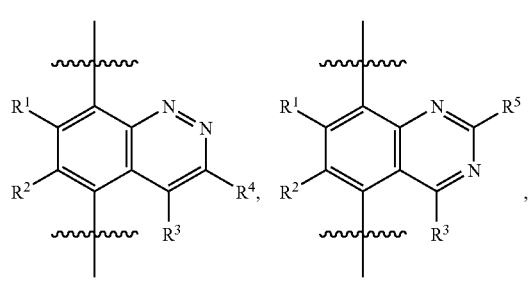
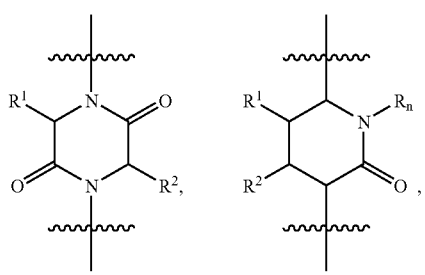
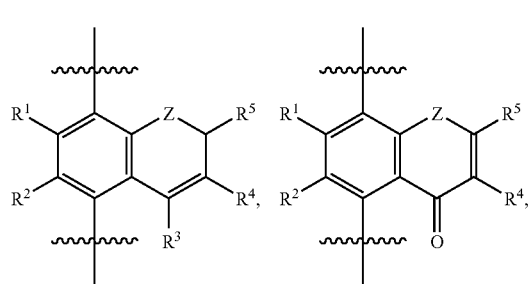
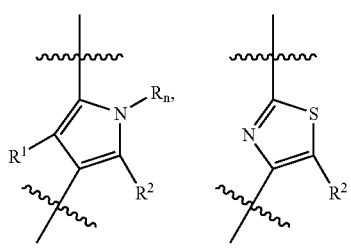
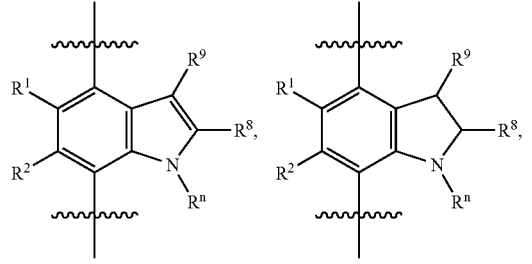
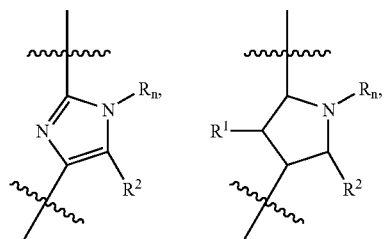
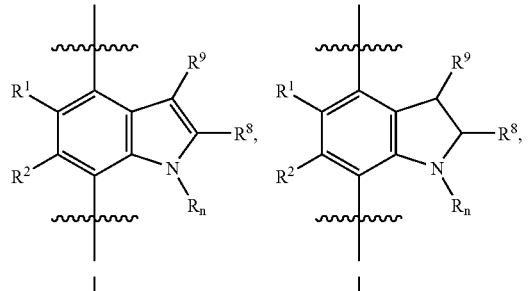
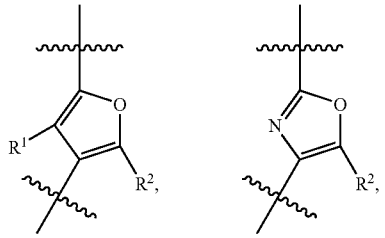
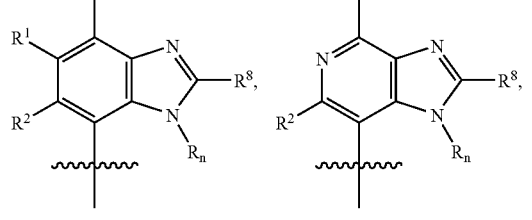
or a fused-ring system according to the structure:

-continued

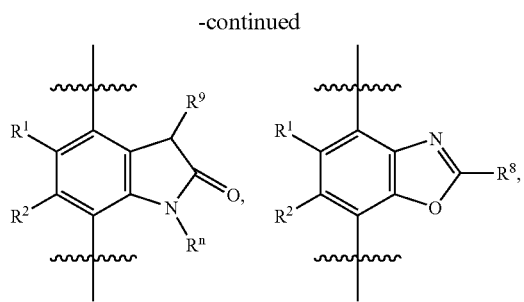

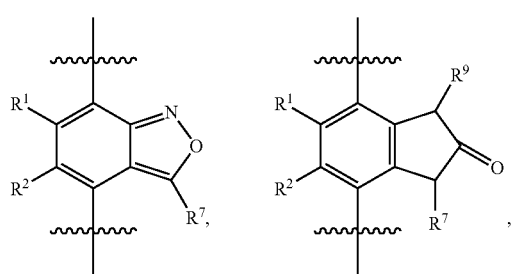

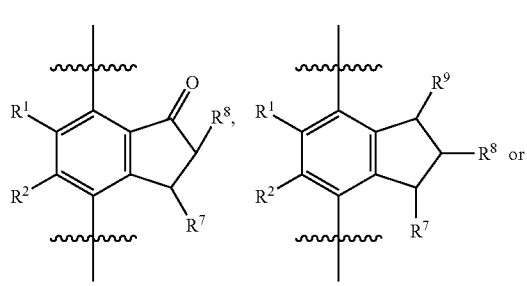

W and Y are each independently selected from the group consisting of

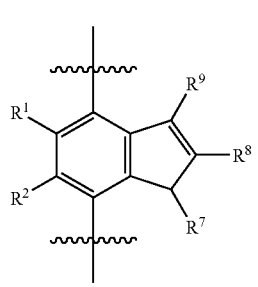

-continued

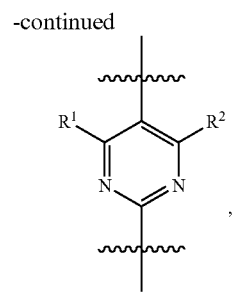

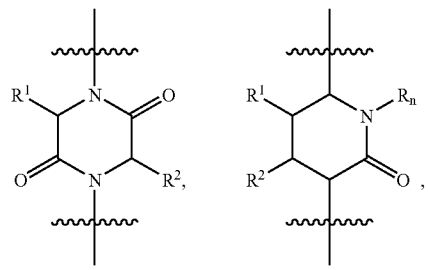

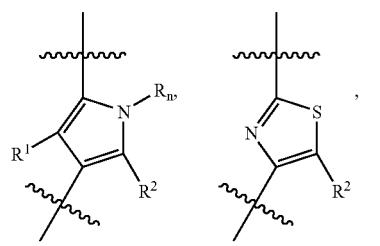

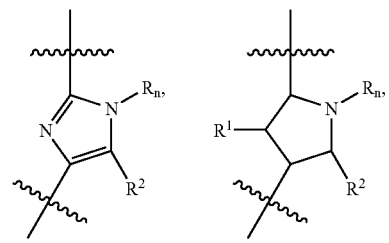

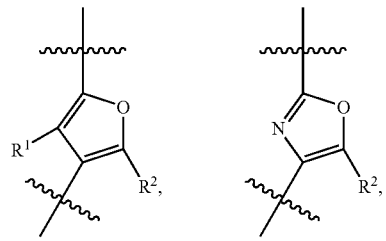

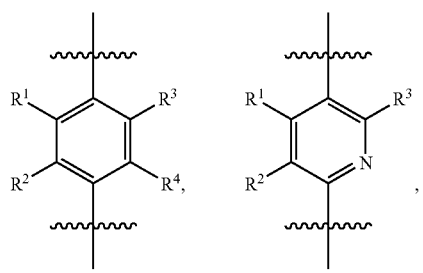

Where $R^1$, $R^2$, $R^3$, $R^4$, $R^5$, $R^6$, $R^7$, $R^8$ and $R^9$ are each independently selected from the group consisting of unsubstituted or substituted hydrocarbon, preferably an alkyl or alkylene group, unsubstituted or substituted aryl, including benzyl and naphthyl, alkylenearyl, alkylaryl, (preferably alkylene phenyl and alkylphenyl,) alkoxy, ester (including an alkyl or aryl ester or an alkylene ester wherein said ester group preferably comprises a $C_1$-$C_6$ alkyl or aryl, preferably benzyl or phenyl group), alkanol, alkanoic acid (said term including embracing a carboxylic acid without further substitution), thioester (preferably a $C_1$-$C_6$ alkyl/$C_1$-$C_6$ alkylene thioester), thioether (preferably a $C_1$-$C_6$ alkyl/$C_1$-$C_6$ alkylene thioether, even more preferably a methyl ethyl as methionine thioether), substituted or unsubstituted amine (including an alkylamine and dialkylamine, preferably $C_1$-$C_6$ alkyl), substituted or unsubstituted alkylamide (preferably, $C_1$-$C_6$ alkyl), substituted or unsubstituted alkylene amide (preferably $C_1$-$C_6$ alkylene which may be substituted on the amine groups of the amide, preferably with alkyl groups), substituted or unsubstituted alkyleneamine (preferably $C_1$-$C_6$ alkylene, such term including saturated ring systems containing nitrogen groups), alkyleneguanidine (preferably $C_1$-$C_6$ alkylene); preferably a $C_1$-$C_6$ alkanol, $C_1$-$C_6$ alkanoic acid, or $C_1$-$C_6$ alkylamide, $C_1$-$C_6$ alkyleneamine or a $C_1$-$C_6$ alkyleneguanidine;

Rn is a $C_1$-$C_{10}$ (preferably, $C_1$-$C_6$) alkyl, alkanol or aryl, or a

group, where T is H or a $C_1$-$C_{12}$ saturated or unsaturated hydrocarbon (forming an amide with the ring nitrogen) group, amine, alkylamine, dialkylamine (all preferably $C_1$-$C_6$ alkyl), substituted or unsubstituted alkyleneamine (preferably, $C_1$-$C_6$) or substituted or unsubstituted alkyleneamide (preferably, $C_1$-$C_6$);

Z is O or S; and

B is a single bond between carbon atoms of W—X or X—Y groups or an ester or amide group linking W—X or X—Y groups.

In certain preferred aspects of the present invention X is a phenyl, piperazinyl or pyridinyl group as set forth above and W and Y are selected from the group consisting of phenyl, piperazinyl, pyridinyl, napththyl and indole, preferably W and Y are phenyl, piperazinyl or pyridinyl and $R^1$, $R^2$, $R^3$, $R^4$, $R^5$, $R^6$, $R^7$, $R^8$ and $R^9$ are each independently selected from the group consisting of H, $C_1$-$C_6$ alkyl, benzyl, 4-hydroxybenzyl, $C_1$-$C_6$ alkanol, $C_1$-$C_6$ alkanoic acid, $C_1$-$C_6$ alkylamide, $C_1$-$C_6$ alkyleneamine, $C_1$-$C_6$ alkyleneguanidine with the proviso that no more than two R substituents on each of W, X or Y groups are other than H;

Rn is a $C_1$-$C_{10}$ alkyl, alkanol, aryl or a

group, where T is H or a $C_1$-$C_6$ alkyl, amine, $C_1$-$C_6$ alkylamine, $C_1$-$C_6$ dialkylamine, unsubstituted or substituted $C_1$-$C_6$ alkyleneamine or unsubstituted or substituted $C_1$-$C_6$ alkyleneamide;

Z is O or S; and

B is a single bond between carbon atoms of W—X or X—Y groups or an amide group linking W—X or X—Y groups.

Compounds according to the present invention may be used as active agents in pharmaceutical compositions as agonists or inhibitors of α-helical proteins in their interactions with proteins (such as receptors, enzymes, other proteins) or other binding sites, said compositions comprising an effective amount of one or more of the compounds disclosed above, formulated as a pharmaceutical dosage form, optionally in combination with a pharmaceutically acceptable carrier, additive or excipient. Pharmaceutical compositions according to the present invention may be used in the treatment of cancer (as, for example, a suppressor of Mdm2/p53 tumor, to inhibit BcL protein family/Bak protein family or AP-1 transcription factor/DNA complex), proliferative diseases including, for example, psoriasis, genital warts and hyperproliferative keratinocyte diseases including hyperkeratosis, ichthyosis, keratoderma or lichen planus, neuropeptide Y receptor interactions, including the resulting hypertension and and neuronal/neurological effects (to facilitate neuromodulation through, for example, inhibition of calmodulin binding on calmodulin dependent phosphodiesterase including PDE1A, PDE1B and PDE1C, among others), neurodegenerative diseases including Alzheimer's disease and Parkinson's disease, Herpes simplex virus infections (HSV, through inhibition of the HSV VP16/human TAF1131 HSV infection complex), HIV infections (through inhibition of HIVp7 nuclear capsid protein/RNA interaction or alternatively, through inhibition of the REV protein RNA complex), asthma, hypertension, cancer and autoimmune diseases (through immunomodulation, for example, by inhibition or modulation of interleukin/receptor interaction), numerous viral infections other than HIV or HSV through inhibition of ribonucleotide reductase dimerization, or to modulate nuclear receptor/coactivator protein complex interaction (eg. estrogen receptor for anticancer therapy) and to disrupt G protein coupled receptor (GPCR) function (through displacement of one of the helixes and disruption of the helix packing interactions or alternatively, by blocking the interacton of the ligand with GPCR, e.g. where the ligand contains a key helix binding domain (e.g. GCSF, calcitonin, interleukins, parathyroid hormones, among others).

In other aspects of the present invention, certain compounds according to the present invention may be used as agonists or antagonists in binding assays, as analytical agents, as agents to be used to isolate or purify proteins, and as intermediates in the synthesis of further peptidomimetic agents, among other uses.

The present invention also relates to methods of treating patients in need thereof for conditions or disease states which are modulated through interactions between alpha helical proteins and other proteins or binding sites are other aspects of the invention. Thus, in the method aspect of the present invention, pharmaceutical compositions comprising α-helical protein agonists or antagonists may be used to treat any condition or disease state in which α-helical proteins modulate their activity through a receptor or other binding site. In particular, the method aspect of the present invention relates to the inhibition of protein binding to binding sites within the patient in order to effect a biological/pharmacological result. Compounds according to the present invention may be used as proteomimetics to inhibit the interaction between a native α helical protein (i.e., a natural α helical protein normally found in a patient) and its binding site. Preferred compounds according to the present invention may be used to disrupt or compete with the binding of a number of proteins including, for example, calmodulin (CaM) with binding sites on smooth muscle light chain kinase (smMLCK) or phosphodiesterase (PDE1A, PDE1B, PDE1C) with resulting neuromuscular and neuronal (among other) effects in the treating of disease states or conditions, gp41 (HIV) and other viruses such as HSV or HBV, for the viral invasive binding cites in CD4 and/or other hematopoietic cells, genital/mucosal cells, among others (HSV)and hepatocytes (HBV), among numerous others and pro-apoptotic Bak- and/or Bad-proteins, for their binding interaction with BCl-$x_L$ protein in a preferred treatment for cancer.

Thus, the present application is directed to the treatment of disease states or conditions which are modulated through interactions between α-helical proteins and other proteins or binding sites of the α-helical proteins selected from the group consisting of viral infections (including Hepatitis B virus (HBV) infections, human immunodeficiency virus (HIV) infections or conditions associated with such infections (AIDS), Herpes Simplex virus infections (HSV) infections, tumors and/or cancer, proliferative diseases including psoriasis, genital warts and hyperproliferative keratinocyte diseases including hyperkeratosis, ichthyosis, keratoderma, lichen planus, hypertension, neuronal disorders by promoting neuromodulation including, for example, attention deficit disorder, memory loss, language and learning disorders, asthma, autoimmune diseases including lupus (lupus erythematosus), multiple sclerosis, arthritis, including rheumatoid arthritis, rheumatic diseases, fibromyalgia, Sjögren's disease and Grave's disease and neurodegenerative diseases including Alzheimer's disease and Parkinson's disease, said method comprising administering to a patient in need thereof an effective amount of a pharmaceutical composition comprising any one or more of the compounds previously described above.

Definitions: The following definitions shall be used when describing the present invention.

"Patient" refers to a mammal, preferably a human, in need of treatment or therapy to which compounds according to the present invention are administered in order to treat a condition or disease state modulated through the binding of an α-helical protein with a binding site.

"Modulated" means, with respect to disease states or conditions modulated through binding of α-helical proteins to binding sites, that the binding or lack or absence of binding of an α-helical protein to a binding site produces or will produce, either directly or indirectly, a condition or disease state which is sub-optimal and in many cases, debilitating and even life threatening.

"Sterically and electronically similar" refers to synthetic substituents on chemical cages or scaffolds according to the present invention which mimic the steric and/or electronic physicochemical characteristics of substituents on α carbons in natural α helical proteins. While not necessarily identical to the natural substituents, substituents which are sterically and electronically similar to the natural substituents promote the binding of synthetic compounds according to the present invention to α helical protein binding sites.

"Chemical cages or scaffords" according to the present invention represent terphenyl or other structures as otherwise disclosed herein in which three cyclical chemical moieties are bound together directly through chemical bonds or through amide or ester groups) and are substituted with groups bound to one or more of the three cyclical chemical moieties. These chemical cages are generally substituted with any number of substituents, preferably those which mimic natural substituents on α carbons (from the amino acids) of α helical proteins.

"Hydrocarbon" refers to any monovalent radical containing carbon and hydrogen, which may be straight or branch-chained or cyclic in nature. Hydrocarbons include linear, branched and cyclic hydrocarbons, including alkyl groups, alkylene groups, unsaturated hydrocarbon groups, both substituted and unsubstituted.

"Alkyl" refers to a fully saturated monovalent radical containing carbon and hydrogen, and which may be cyclic, branched or a straight chain. Examples of alkyl groups are methyl, ethyl, n-butyl, n-hexyl, isopropyl, 2-methylpropyl, cyclopropyl, cyclopropylmethyl, cyclobutyl, cyclopentyl, cyclopentylethyl, and cyclohexyl. "Alkylene" refers to a fully saturated hydrocarbon which is divalent (may be linear, branched or cyclic). Other terms used to indicate substituent groups in compounds according to the present invention are as conventionally used in the art. Thus, the term alkylene phenyl includes a benzyl group or ethylene phenyl group, alkylphenyl includes a phenyl group which has alkyl groups as substituents, etc.

"Aryl" refers to a substituted or unsubstituted monovalent aromatic radical having a single ring (e.g., benzene) or multiple condensed rings (e.g., naphthyl, anthracenyl, phenanthryl). Other examples of aryl groups include heterocyclic aromatic ring systems having one or more nitrogen, oxygen, or sulfur atoms in the ring, such as imidazole, furyl, pyrrole, pyridyl, indole and fused ring systems, among others, which may be substituted or unsubstituted.

The term "effective amount" refers to the amount of a selected compound which is effective within the context of its use or administration. In the case of therapeutic methods according to the present invention, the precise amount required will vary depending upon the particular compound selected, the age and weight of the subject, route of administration, and so forth, but may be easily determined by routine experimentation.

The term "substituted" shall mean substituted at a carbon (or nitrogen) position with an alkyl group (preferably, $C_1$-$C_6$), alkoxy group (preferably, $C_1$-$C_6$ alkyl or aryl), ester (preferably, $C_1$-$C_6$ alkyl or aryl) including alkylene ester (such that attachment is on the alkylene group, rather than at the ester function which is preferably substituted with a $C_1$-$C_6$ alkyl or aryl group), thioether (preferably, $C_1$-$C_6$ alkyl or aryl), thioester (preferably, $C_1$-$C_6$ alkyl or aryl), (preferably, $C_1$-$C_6$ alkyl or aryl), halogen (F, Cl, Br, I), nitro or amine (including a five- or six-membered cyclic alkylene amine, preferably, a $C_1$-$C_6$ alkyl amine or $C_1$-$C_6$ dialkyl amine), alkanol (preferably, $C_1$-$C_6$ alkyl or aryl), or alkanoic acid (preferably, $C_1$-$C_6$ alkyl or aryl). Preferably, the term "substituted" shall mean within its context alkyl, alkoxy, halogen, nitro and amine (including mono- or di-alkyl substituted amines). The term unsubstituted shall mean substituted with one or more H atoms.

The term "binding site" refers to a site at which an α-helical protein binds and elicits some response or action at that binding site, which action may be direct or indirect. Compounds according to the present invention will also bind at the binding site of the α-helical binding site in an agonistic or antagonistic manner. The binding site may be another protein, a receptor (such as a cell surface receptor or a G-protein coupled receptor), signaling proteins, proteins involved in apoptotic pathways (especially neuronal apoptosis), active sites and regulatory domains of enzymes, growth factors, DNA, RNA (including polynucleotides and oligonucleotides), viral fusion proteins and viral coat proteins, among numerous others.

The term "pharmaceutically acceptable carrier" refers to carrier, additive or excipient which is not unacceptably toxic to the subject to which it is administered. Pharmaceutically acceptable excipients are described at length by E. W. Martin, in "Remington's Pharmaceutical Sciences", among others well-known in the art.

A "pharmaceutically acceptable salt" of the present compound generally refers to pharmaceutically acceptable salts of an amine compound, such as those contemplated in the current invention, such as an ammonium salt having as counterion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like. Certain compounds according to the present invention which have carboxylic acid groups may also form pharmaceutically acceptable salts, generally, as carboxylate salts.

Aspects of the present invention include compounds which have been described in detail hereinabove or to pharmaceutical compositions which comprise an effective amount of one or more compounds according to the present invention, optionally in combination with a pharmaceutically acceptable carrier, additive or excipient.

Another aspect of the present invention is directed to compounds according to the present invention which may be used to mimic $\alpha$-helical proteins in an agonistic or antagonistic manner. In this aspect of the present invention, one or more of the compounds according to the present invention may be used to mimic or inhibit the binding of an $\alpha$-helical protein for its binding site, whether that binding site is another protein, a receptor (such as a cell surface receptor or a G-protein coupled receptor), signaling proteins, proteins involved in apoptotic pathways (especially neuronal apoptosis), active sites and regulatory domains of enzymes, growth factors, DNA, RNA (including oligonucleotides), viral fusion proteins and viral coat proteins, among numerous others. In certain aspects of the present invention, one or more compound according to the present invention may be used to inhibit the binding of calmodulin to a calmodulin dependent phosphodiesterase enzyme (PDE1A, PDE1B or PDE1C).

In another aspect, the present invention is directed to the use of one or more compounds according to the present invention in a pharmaceutically acceptable carrier, additive or excipient at a suitable dose ranging from about 0.05 to about 100 mg/kg of body weight per day, preferably within the range of about 0.1 to 50 mg/kg/day, most preferably in the range of 1 to 20 mg/kg/day. The desired dose may conveniently be presented in a single dose or as divided doses administered at appropriate intervals, for example as two, three, four or more sub-doses per day.

Ideally, the active ingredient should be administered to achieve effective peak plasma concentrations of the active compound within the range of from about 0.05 to about 5 uM. This may be achieved, for example, by the intravenous injection of about a 0.05 to 10% solution of the active ingredient, optionally in saline, or orally administered as a bolus containing about 1mg to about 5 g, preferably about 5 mg to about 500 mg of the active ingredient, depending upon the active compound and its intended target. Desirable blood levels may be maintained by a continuous infusion to preferably provide about 0.01 to about 2.0 mg/kg/hour or by intermittent infusions containing about 0.05 to about 15 mg/kg of the active ingredient. Oral dosages, where applicable, will depend on the bioavailability of the compounds from the GI tract, as well as the pharmacokinetics of the compounds to be administered. While it is possible that, for use in therapy, a compound of the invention may be administered as the raw chemical, it is preferable to present the active ingredient as a pharmaceutical formulation, presented in combination with a pharmaceutically acceptable carrier, excipient or additive.

Pharmaceutical formulations include those suitable for oral, rectal, nasal, topical (including buccal and sub-lingual), vaginal or parenteral (including intramuscular, sub-cutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenously or intramuscular dosage form, as well as via other parenteral routes, such as transdermal, buccal, subcutaneous, suppository or other route. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

In particular, the modification of the present compounds to render them more soluble in water or other vehicle, for example, may be easily accomplished by minor modifications (such as salt formulation, etc.) which are well within the ordinary skill in the art. It is also well within the routineer's skill to modify the route of administration and dosage regimen of a particular compound in order to manage the pharmacokinetics of the present compounds for maximum beneficial effect to the patient.

Formulations containing the compounds of the invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, and the like. Preferably, the composition will be about 0.05% to about 75-80% by weight of a compound or compounds of the invention, with the remainder consisting of suitable pharmaceutical additives, carriers and/or excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20%), and optional pharmaceutical additives, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or will be apparent to those skilled in the art; for example, see "Remington's Pharmaceutical Sciences" (17th Ed., Mack Pub. Co, 1985). The composition to be administered will contain a quantity of the selected compound in a pharmaceutically effective amount for effecting increased AMPA receptor currents in a subject.

The person of ordinary skill will take advantage of favorable pharmacokinetic parameters of the pro-drug forms of the present invention, where applicable, in delivering the present compounds to a patient suffering from a viral infection to maximize the intended effect of the compound.

The pharmaceutical compositions according to the invention may also contain other active ingredients such as antimicrobial agents, antinfective agents, or preservatives. Effective amounts or concentrations of each of the active compounds are to be included within the pharmaceutical compositions according to the present invention.

The individual components of such combinations may be administered either sequentially or simultaneously in separate or combined pharmaceutical formulations.

When one or more of the compounds according to the present invention is used in combination with a second therapeutic agent active the dose of each compound may be either the same as or differ from that when the compound is used alone. Appropriate doses will be readily appreciated by those skilled in the art.

In method aspects according to the present invention, one or more pharmaceutical compositions according to the present invention may be administered in the treatment or prevention of any disease state or condition which is modulated by the interaction of an α-helical protein with binding sites for the α-helical protein. Methods for treating conditions or disease states which are modulated through the binding of an α-helical protein according to the present invention comprise administering to a patient in need thereof an effective amount of a compound according to the present invention in an amount and for a duration to treat, resolve, reduce or eliminate the condition or disease state. Conditions or disease states which may be treated using compounds according to the present invention include, for example, viral infections (including Hepatitis B virus (HBV) infections, human immunodeficiency virus (HIV) infections or conditions associated with such infections (AIDS), Herpes Simplex virus infections (HSV) infections, tumors and/or cancer, proliferative diseases including psoriasis, genital warts and hyperproliferative keratinocyte diseases including hyperkeratosis, ichthyosis, keratoderma, lichen planus, hypertension, neuronal disorders so as to promote neuromodulation, asthma, autoimmune diseases including lupus (lupus erythematosus), multiple sclerosis, arthritis, including rheumatoid arthritis, rheumatic diseases, fibromyalgia, Sjögren's disease and Grave's disease, neuronal disorders such as ADD, memory loss, learning and language disorders, and neurodegenerative diseases including Alzheimer's disease and Parkinson's disease, among others.

Chemical Synthesis

Compositions according to the present invention are synthesized using the general and synthetic methods which are set forth below.

General Method

The invention relates to a method for the formation of synthetic pharmaceutically active agents that are mimics of α-helix structure and function. The general embodiment of the invention involves the grafting of essential amino side chain residues from different positions on the surface of an α-helix onto a synthetic, rigid molecular scaffold that reproduces the distance and angular orientation of the side chains for functional binding to a protein target. The key to the invention is the original design of the synthetic scaffold which exploits a cylindrical shape to provide substitution positions that match the positions of the α-carbon atoms of the amino acids of a peptide or protein sequence in an α-helical conformation. The synthetic scaffold will be chosen from two groups embodied by the structure

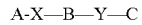

Where A, B and C are substituted aromatic or alicyclic rings linked either directly or through a connecting bond such as an amide or ester group (X, Y=ester or amide).

General Synthetic Methods

Two general synthetic routes are envisioned for the two major embodiments of the invention. The first involves directly linked substituted aromatic and alicyclic ring systems. These are prepared through a sequential series of palladium catalyzed coupling reactions of the individual monomeric components that are present as their substituted methoxy-halide (or boronate ester) derivatives. In the case of aromatic ring systems, reaction of the first component with a functionalized olefin or haloalkane through Heck or related reactions gives the terminally functionalized A component where W is chosen to enhance electrostatic or hydrophobic interaction to the target protein or to modulate solubility or pharmacokinetic properties. Deprotection of the methoxy group followed by formation of the triflate ester is followed by palladium catalyzed reaction (Suzuki, Stille through the intermediacy of the diketopiperazine) is attached through sequential palladium catalyzed aryl amination reactions.

For those embodiments of the invention that involve aromatic or alicyclic ring systems connected through a

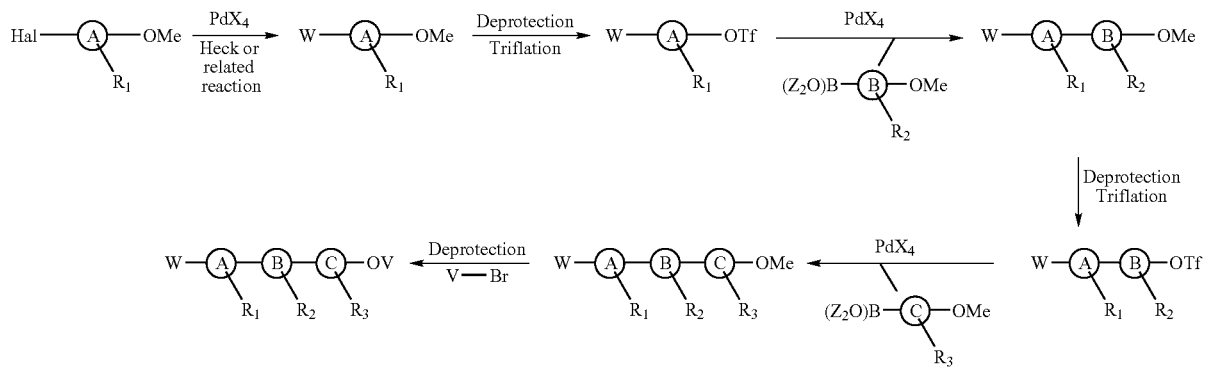

or related reaction) with the corresponding substituted methoxy boronate (or halide) derivative of component B (the boronate being formed directly from the halide derivative) to give the dimeric intermediate. Further deprotection of the methoxy group followed by formation of the triflate ester is followed by a second palladium catalyzed reaction with the corresponding substituted methoxy boronate (or halide) derivative of component C to give the methoxy-trimer intermediate. Further deprotection of the methoxy group followed by alkylation under basic conditions using a selected alkyl halide V-Br (where V is chosen to enhance electrostatic or hydrophobic interaction to the target protein or to modulate solubility or pharmacokinetic properties) gives the final product. The substituents on the individual components $R^1$, $R^2$, and $R^3$ are chosen to reproduce the recognition properties of the key amino acid side chains in an α-helix.

The synthetic route can be readily modified to permit the insertion of one or more alicyclic rings into the scaffold framework, either in positions A, B or C. For example, a bis azo ring system (such as a substituted piperazine, formed from the corresponding amino acid linking amide or ester group, a general synthetic sequence is outlined below. The individual substituted amino carboxylic acid derivative of component A is protected through a standard amine protecting group (Cbz, Boc, Fmoc, etc. or through nitro group reduction) and standard carboxylic acid protecting group (orthogonal to the amine e.g. tert.-Butyl, benzyl, trichloroethyl, etc). Deprotection of the carboxylate protecting group followed by reaction with a suitable amine or alcohol (WH, where W is chosen to enhance electrostatic or hydrophobic interaction to the target protein or to modulate solubility or pharmacokinetic properties) provides the terminally functionalized monomeric components. Amine deprotection followed by reaction with the N-protected carboxylic acid derivative of substituted component B (in the presence of a coupling reagent such as DCC, CDI, BOP) gives the N-protected dimeric derivative. Further amine deprotection followed by reaction with the N-protected carboxylic acid derivative of substituted component C B (in the presence of a coupling reagent) gives the N-protected trimeric derivative. Further amine deprotection followed by reaction with a carboxylic acid derivative V—COOH in the presence of a coupling reagent such as DCC, CDI, BOP) gives the final functionalized trimeric helix mimetic, where V is chosen to enhance electrostatic or hydrophobic interaction to the target protein or to modulate solubility or pharmacokinetic properties.

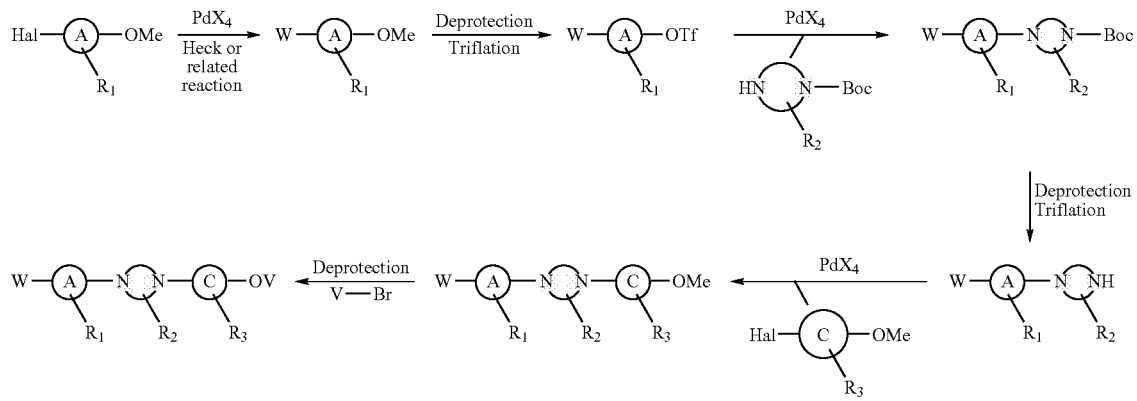

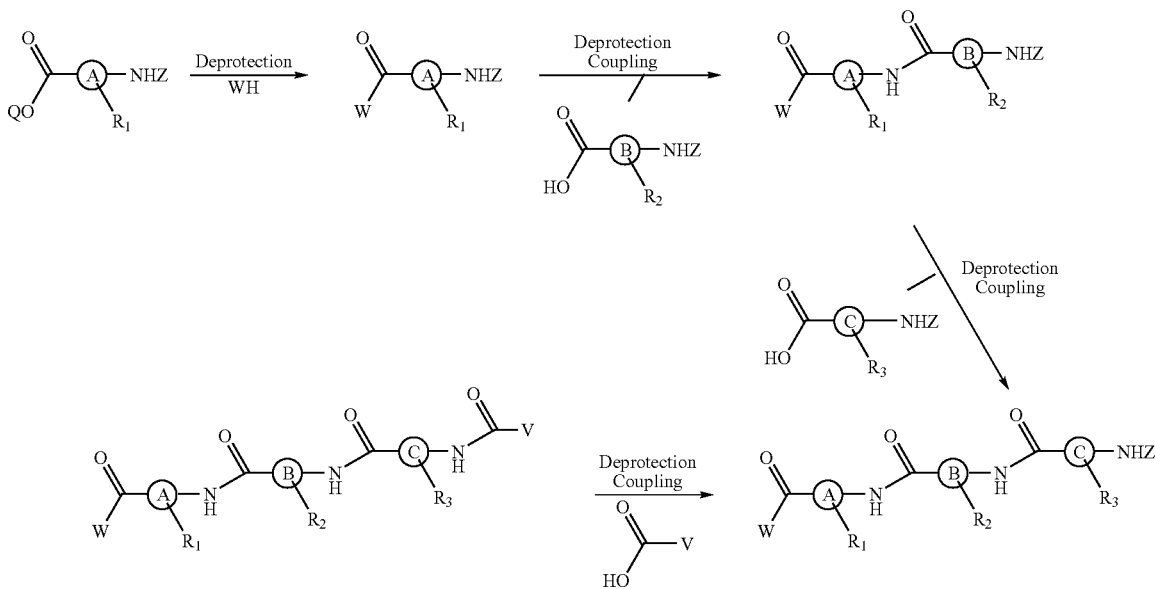

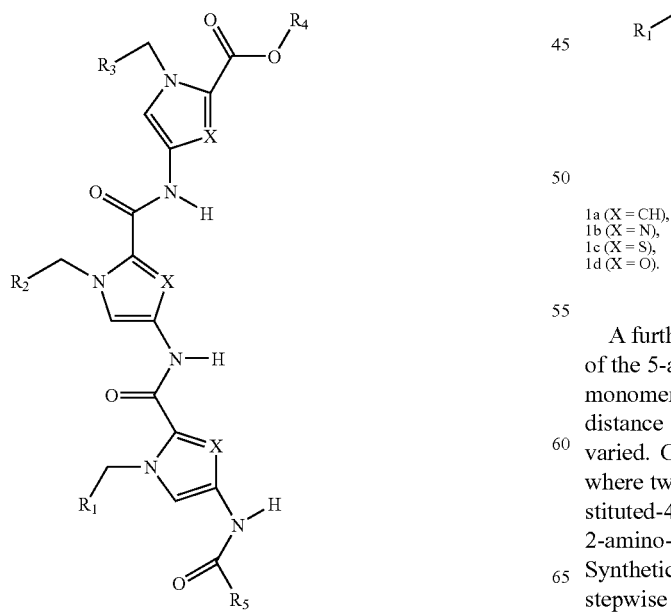

Further embodiments of the conformationally stabilized (foldamer) route to helix mimics is shown in a series of compounds based on pyrrole-4-amino-2-carboxylic acid derivatives (where X=CH), imidazole-4-amino-2-carboxylic acid derivatives (where X=N), thiazole-4-amino-2-carboxylic acid derivatives (where X=S) or oxazole-4-amino2-carboxylic acid derivatives (where X=O). See below, compounds 1a-d. Substituted derivatives of these core scaffolds can be constructed to reproduce the recognition characteristics of the side chains of an a-helix (where $R^1$, $R^2$ and $R^3$ are chosen from the group; alkyl, aryl, substituted benzyl, indolyl, hydroxyalkyl, hydroxycarbonylalkyl, thioalkyl etc.) as described earlier. These compounds can be prepared from stepwise condensation of the protected pyrrole-4-amino-2-carboxylic acid or imidazole-4-amino-2-carboxylic acid precursors. The synthetic routes to these compounds are embodied in the preparation of distamycin and netropsin derivatives through stepwise coupling of amino acid monomers using standard coupling agents. See Tumet, et al., *J. Am. Chem. Soc.*, 1997, 119, 7636-7644.

-continued

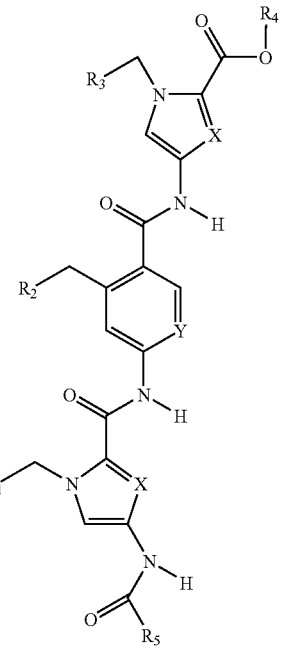

1a (X = CH),
1b (X = N),
1c (X = S),
1d (X = O).

A further embodiment of this approach involves a mixing of the 5-atom heterocycle monomer with the six atom cycle monomers to give a series of helix mimetics in which the distance and angle between the side chain components is varied. Compounds of this type are exemplified as above where two different 5-ring units are linked through a 2-substituted-4-aminobenzoic acid derivative (Y=CH) or a 2-amino-4-substituted nicotinic group derivative (Y=N). Synthetic procedures to these compounds follow similar stepwise coupling procedures in solution or on solid phase as generally described herein.

A further extension of the terphenyl helix mimetic approach involves attachment of additional substituents onto the core terphenyl scaffold as set forth in the chemical scheme presented in FIG. 1. An example of this class of compounds is shown below. The additional substituent ($R_4$ in 1 of FIG. 1) functions to reproduce additional amino acid side chain recognition points within the α-helix being mimicked as well as modulating the physical properties of the molecule (e.g. solubility). An enabling synthetic route to this class of compounds is shown in FIG. 1 using as an example compound 1 where $R_1$=Methyl, $R_2$=methyl, $R_3$=benzyl and $R_4$=hydroxycarbonylethyl.

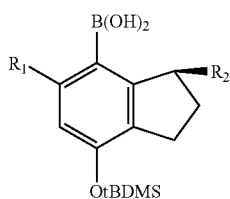

1S

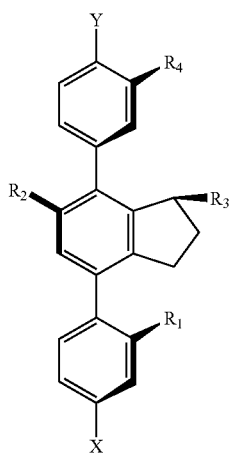

1A

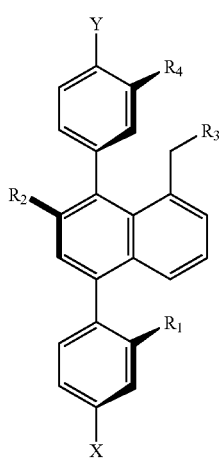

1B

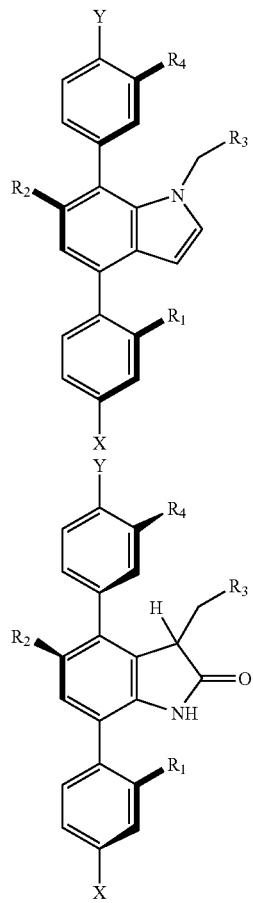

1C

-continued

A further refinement is available from the incorporation of indane subunit 1I in place of the phenyl derivative in the synthetic sequence which is presented in FIG. 1. 1,6-Disubstituted indanes had previously been shown to be good structural mimics of adjacent residues in an α-helical conformation. Subunit 1S can be prepared by modification of published routes and and used the formation of peptidomimetic 1A. The calculated structure for 1A shows that it presents a surface containing features of the i, i+4, i+5 and i+7 residues of the α-helix. Thus, in a small molecule (<550 M. Wt.) side chain functionality from four of the seven residues involved in almost two turns of an α-helix can be incorporated. Compounds of this type can be readily generated through standard aromatic substitution chemistry or modifications of the indane routes. In a similar way, helix mimetics based on 1,4-diaryl-2- and 8-substituted naphthyl derivatives can be prepared (as in 1B). Similarly, the corresponding N-alkylated indole or 3-substituted oxindole derivatives, as in 1C and 1D, respectively, provide different distance and angular constraints on the side chain mimics of the i, i+4, i+5 and i+7 residues of the α-helix. In these cases the indane, naphthyl, indole and oxindole components are occupying the central position of the helix mimetic. However in all cases the indane, naphthyl, indole and oxindole components can alternatively or additionally occupy the first and third positions.

In a further aspect of the present invention, a method of producing proteomimetic compounds is contemplated, such method comprising providing a cylindrical cage or rigid scaffold compound according to the structure:
W—B—X—B—Y
Wherein X is selected from the group consisting of a five or six-membered ring selected from the group consisting of:
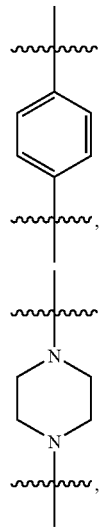
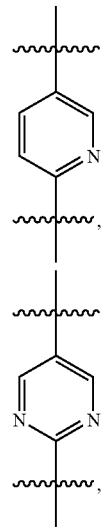
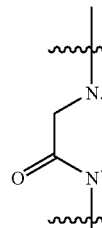
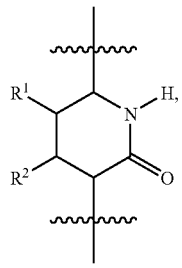
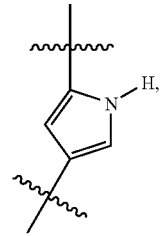
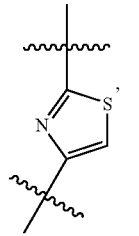
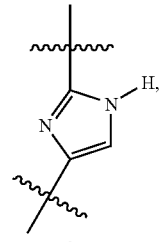
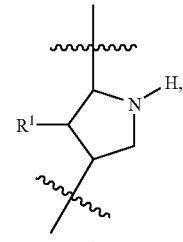
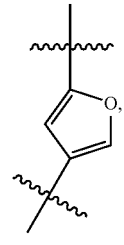
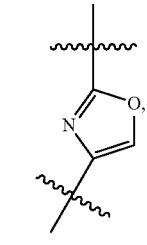
or a fused ring system selected according to the structure:
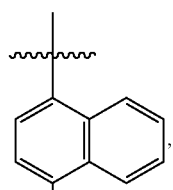
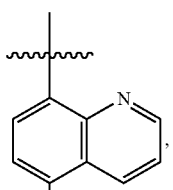
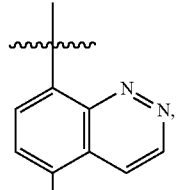
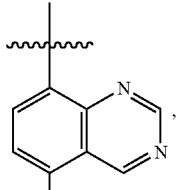
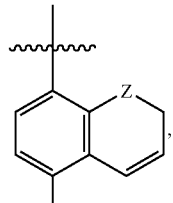
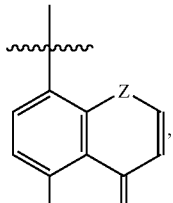
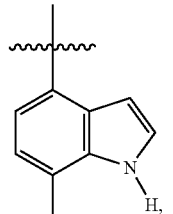
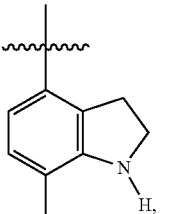
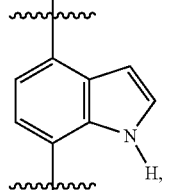
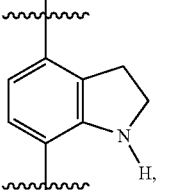
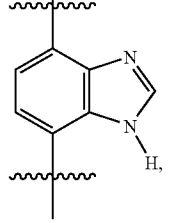
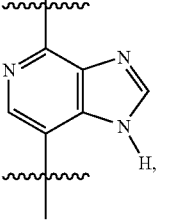

-continued

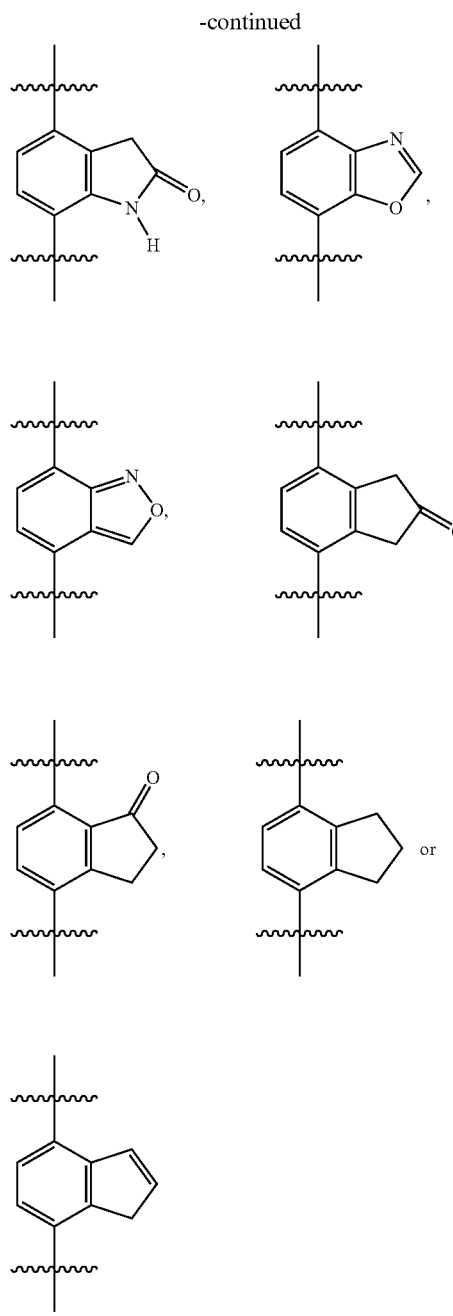

W and Y are each independently selected from the group consisting of

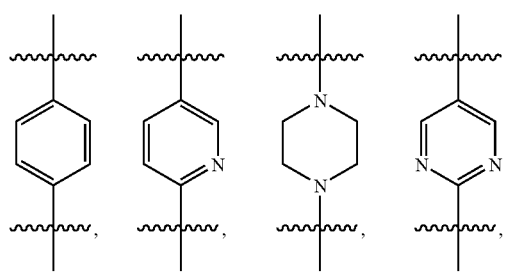

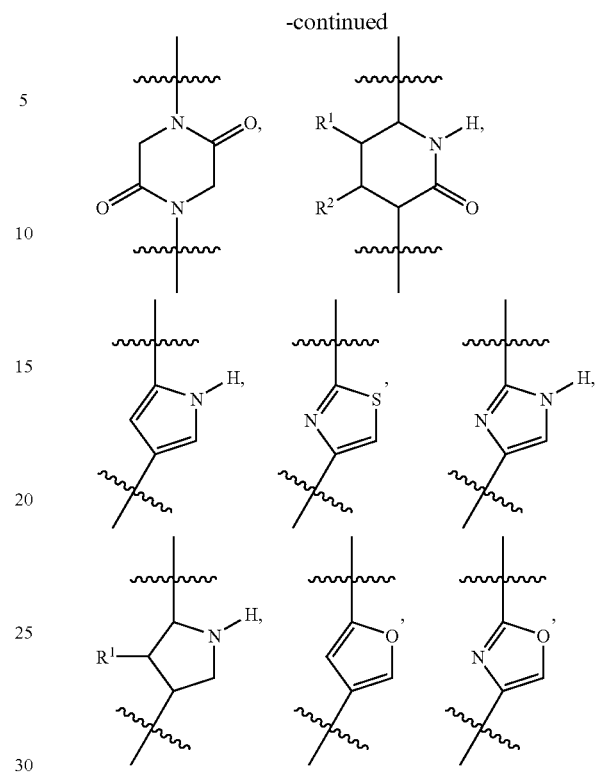

and each B is independently a connecting bond or an amide or ester group connecting W to said X and Y groups;

said method further comprising identifying chemical groups that are sterically and electronically similar to the substituents on the α carbon atoms of natural amino acids and attaching said substituents to unbound atoms on the ring structures of said chemical scaffold, said substituents closely matching the substituents on positions of the α carbon atoms of a peptide or protein sequence in an α helical protein. In such method, the substituent is selected from the group consisting of hydrogen, $C_1$-$C_6$ alkanol, thioether, mercaptan, benzyl, hydroxybenzyl, $C_1$-$C_6$ alkyleneamide, ethyleneamide, $C_1$-$C_6$ alkanoic acid, $C_1$-$C_6$ alkyleneamine, alkylene-1,3-pyrazole, $C_1$-$C_6$alkyleneguanidine and $C_1$-$C_6$ alkanolamine. In still further aspects of the method, the substitutent is selected from the group consisting of hydrogen (glycine), methyl (alanine), isopropyl (valine), isobutyl (isoleucine), sec-butyl (leucine), benzyl, 4-hydroxybenzyl (from tyrosine), pyrrolidinyl (from proline), indole (tryptophan), methyl-methylenethioether (methionine), methanol (serine), 1-ethanol (threonine), acetate, propionate, methyleneamide (asparagine), ethyleneamide (glutamine), butyleneamine (lysine), propyleneguanidine (arginine), methylenepyrazole (histidinyl) and methylmercaptan (cysteine).

One of ordinary skill in the art will readily recognize the variations and modifications which can be made to the general synthetic methods which have been presented above.

EXAMPLES

The following examples illustrate but are not intended in any way to limit the invention.

All chemicals were obtained from Sigma/Aldrich unless otherwise noted. All peptides were purchased from the HHMI Biopolymer/Keck Foundation Biotechnology Resource Center at the Yale University School of Medicine (New Haven, Conn.). All solvents were appropriately distilled, all glassware was flame dried prior to use and all reactions were run under an inert (N$_2$) atmosphere unless otherwise noted. Column chromatography was performed using silica gel (230-400 mesh) and preparative thin layer chromatography was completed using 20×20 cm, 1000 micron precoated silica gel plates with fluorescent indicator (Analtech Inc., Newark Del.). $^1$H NMR spectra were recorded on Bruker Avance DPX-500 and DPX-400 spectrometers at 500 or 400 MHz. $^{13}$C NMR spectra were recorded on a Bruker Avance DPX-500 spectrometer at 125 MHz. Chemical shifts are expressed as parts per million using solvent as the internal standard. All mass data were obtained from the mass spectroscopy facility at the University of Illinios at Urbana Champaign under the supervision of Dr. Steven Mullen.

Computation. Computational analysis, where presented, was completed using Macromodel (W. C. Still, Columbia). MM2 energy minimizations performed on 3, 2', 2"-trimethylterphenyl indicate that the structure with 55° torsion angles to be the closest of several low energy conformers to the structure that presents i, i+4, i+7 side chain mimicry. The six carbon atoms of this conformation corresponding to the three Cα and the three Cα carbons of the i, i+4, i+7 alanines (yellow in FIG. 2) were overlayed on the helix. The resulting root mean squared difference (rmsd) between these atoms was calculated to be 0.90 Å.

Circular Dichroism. CD spectra, where reported, were obtained on an Aviv Dichroism Model 202 spectrometer at 4° C., using a 1 nm bandwith, 1 nm resolution, 0.1 nm path length, and a 5.0 sec averaging time. Spectra were corrected by the subtraction of a blank corresponding to the solvent composition of each sample. All spectra were recorded in aqueous buffer (50 mM PBS, 150 mM NaCl, pH 7.0). Inhibitor stock solutions were composed of 1:1 buffer/trifluoroethanol (TFE). Overall TFE concentrations in the experiments never exceeded 0.5%. TFE had no effect on the CD spectra up to 5% (maximum tested). CD thermal denaturation experiments were completed by monitoring the Θ222 signal using a 4-90° C. temperature range with a temperature step of 2 deg/min, dead band value of 0.2, equilibration time of 1 min, and an averaging time of 30 sec. The $T_m$ values for the unfolding transitions were estimated from the maximum of the first derivative with respect to a plot of CD signal at Θ222 versus $T^{-1}$.

The following compounds, as indicated, were synthesized.

Figure 2:
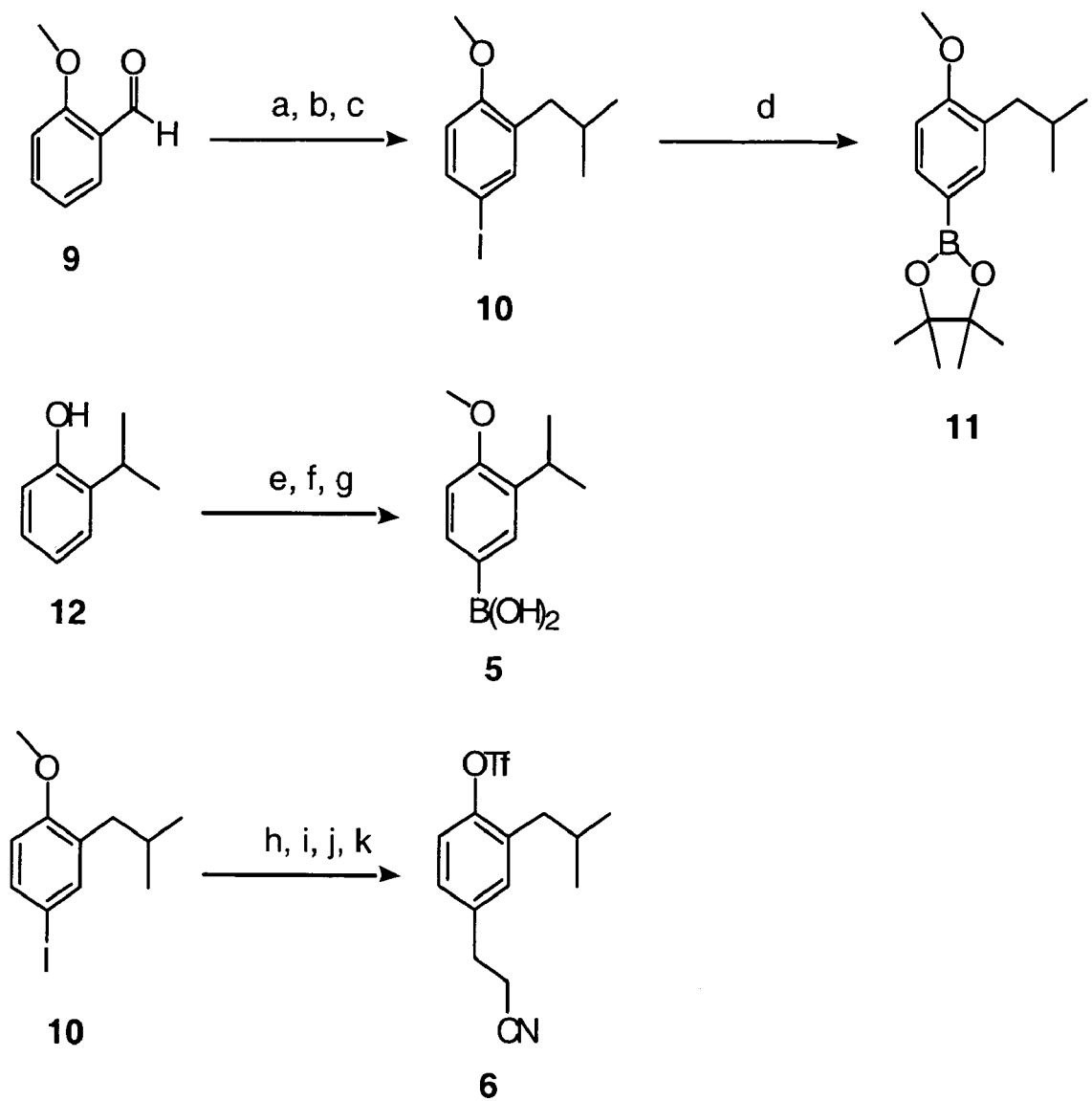
FIG. 2 is a scheme representing the chemical synthesis of substituted phenyl derivative 6. The following legend applies to FIG. 2, Scheme 2: a) (i) isopropyl triphenylphosphonium iodide, BuLi, $Et_2O$, 0° C.-rt, 35 min, (ii) 9, rt, 20 h, 61%; b) $H_2$ (60 psi), 10% Pd/C, EtOH, rt, 9 h, 84%; c) Selectfluor reagent, $I_2$, $CH_3CN$, rt, 8 h, 73%; d) bis(pinacolato)diboron, KOAc, $PdCl_2dppf$, DMSO, 85° C., 3 h, 67%; e) dioxane dibromide, $Et_2O$, 0° C.-rt, 30 min, 66%; f) MeI, $K_2CO_3$, acetone, 56° C., 24 h, 91%; g) (i) BuLi, THF, −78° C., 30 min, (ii) $B(OMe)_3$, rt, 24 h, (iii) NaOH, rt, 1 h, (iv) HCl, 95%; h) acrylonitrile, $Pd(OAc)_2$, tetra-n-butylammonium chloride, $NaHCO_3$, DMF, 40° C., 19 h, 74%; i) (i) Mg, MeOH, 0° C.-rt, 5 h, (ii) 6M HCl, 96%; j) $BBr_3$, $CH_2Cl_2$, 10° C., 9 h, 99%; k) $Tf_2O$, pyridine, 0° C.-rt, 17 h, 93%.

Synthesis Following the Presentation in FIG. 2, Scheme 2

1-(2-methoxyphenyl)-2-methylpropene (9a). Isopropyl triphenylphosphonium iodide (5.95 g, 13.7 mmol, 1.5 eqv) was suspended in 230 ml of Et$_2$O at 0° C. n-BuLi (8.6 ml of a 1.6 M solution in hexanes, 13.7 mmol, 1.5 eqv) was added via syringe. The subsequent red solution was allowed to stir for 35 min at rt. 2-Methoxybenzaldehyde (9) (1.25 g, 9.18 mmol) in 10 ml of Et$_2$O was added via syringe and the resulting solution was allowed to stir for 20 h at rt. The reaction mixture was filtered. The filtrate was diluted with H$_2$O and extracted with Et$_2$O. The organic fractions were combined, dried (MgSO$_4$), filtered, and concentrated in vacuo. Column chromatography [Hexanes/Et$_2$O (9/1)] yielded 0.91 g of a clear oil (61%): $^1$H NMR (500 MHz, CDC$_3$) δ 1.82 (s, 3H), 1.94 (s, 3H), 3.85 (s, 3H), 6.32 (s, 1H), 6.87 (d, J=8.0 Hz, 1H), 6.63 (t, J=7.5 Hz, 1H), 7.21 (m, 2H); $^{13}$C NMR (125 MHz, CDCl$_3$) δ 19.50, 26.60, 55.39, 110.27, 120.01, 120.51, 127.33, 127.50, 130.42, 135.51, 156.96; HRMS (EI) Calcd for C$_{11}$H$_{14}$O: 162.1044. Found 162.1044.

2-isobutylanisole (9b). A solution of 1-(2-methoxyphenyl)-2-methylpropene (9a) (3.37 g, 20.8 mmol) and 10% Pd/C (300 mg) in 100 ml of anhydrous EtOH at rt was hydrogenated at 60 psi until complete conversion was determined by GC/MS (9 h). The reaction mixture was filtered through celite and concentrated in vacuo to yield 2.87 g of a clear oil (84%): $^1$H NMR (500 MHz, CDCl$_3$) δ 0.90 (d, J=6.6 Hz, 6H), 1.92 (m, 1H), 2.49 (d, J=7.1 Hz, 2H), 3.82 (s, 3H), 6.88 (m, 2H), 7.10 (d, J=8.9 Hz, 1H), 7.18 (t, J=8.0 Hz, 1H); $^{13}$C NMR (125 MHz, CDCl$_3$) δ 22.55, 28.64, 39.43, 55.22, 110.27, 120.07, 126.80, 130.22, 130.80, 157.70; HRMS (EI) Calcd for C$_{11}$H$_{16}$O: 164.1201. Found 164.1207.

4-iodo-2-isobutylanisole (10). 2-isobutylanisole (9b) (1.5 g, 9.14 mmol), 1-(chloromethyl)-4-fluoro-1,4-diazoniabicyclo[2.2.2]octane bis(tetrafluoroborate) (3.24 g, 9.14 mmol, 1.0 eqv) and I$_2$ (1.18 g, 4.66 mmol, 0.51 eqv) were dissolved in 90 ml of CH$_3$CN. The solution was stirred for 8 h at rt, diluted with H$_2$O, and extracted with CH$_2$Cl$_2$. The organic fractions were combined, dried (MgSO$_4$), filtered, and concentrated in vacuo. Column chromatography [Hexanes/CH$_2$Cl$_2$ (2/1)] yielded 1.93 g of a clear oil (73%): $^1$H NMR (500 MHz, CDCl$_3$) δ 0.89 (d, J=4.3 Hz, 6H), 1.88 (m, 1H), 2.42 (d, J=7.2 Hz, 2H), 3.78 (s, 3H), 6.61 (d, J=8.5 Hz, 1H), 7.38 (s, 1H), 7.45 (d, J=10.8 Hz, 1H); $^{13}$C NMR (125 MHz, CDCl$_3$) δ 22.45, 28.64, 39.02, 55.37, 82.58, 112.67, 133.20, 135.61, 139.21, 157.72; LRMS (EI) (M+, 290).

2-(3-isobutyl-4-methoxyphenyl)-4,4,5,5-tetramethyl-1,3,2-dioxaborolane (11). A solution of 4-iodo-2-isobutylanisole (10) (0.150 g, 0.52 mmol), bis(pinacolato)diboron (0.144 g, 0.57 mmol, 1.1 eqv), KOAc (0.152 g, 1.55 mmol, 3 eqv), and PdCl$_2$dppf (21 mg, 5 mol %) in 3 ml of DMSO was stirred at 85° C. for 3 h. The mixture was then added to H$_2$O and extracted with CH$_2$Cl$_2$. The organic fractions were combined, back extracted with H$_2$O, dried (MgSO$_4$), filtered, and concentrated in vacuo. Column chromatography [Hexanes/EtOAc (9/1)] yielded 0.100 g of a clear oil (67%): $^1$H NMR (500 MHz, CDCl$_3$) δ 0.84 (d, J=6.5 Hz, 6H), 1.34 (s, 12H), 1.92 (m, 1H), 2.48 (d, J=7 Hz, 2H), 3.84 (s, 3H), 6.84 (d, J=8.5 Hz, 1H), 7.54 (s, 1H), 7.66 (d, J=10 Hz, 1H); $^{13}$C NMR (125 MHz, CDCl$_3$) δ 22.59, 24.86, 28.84, 39.21, 55.15, 83.44, 109.58, 129.56, 134.31, 137.38, 160.39; HRMS (EI) Calcd for C$_{17}$H$_{27}$BO$_3$: 290.2053. Found 290.2052.

4-bromo-2-isopropylphenol (12e). To a solution of 2-isopropylphenol (12) (2.0 g, 14.6 mmol) in 15 ml of Et$_2$O at 0° C. was added dioxane dibromide (3.62 g, 14.6 mmol, 1 eqv). The solution was allowed to stir for 30 min at rt. The reaction mixture was washed with sat. NaCl and 10% NaHCO$_3$. The Et$_2$O phase was concentrated in vacuo and then vacuum distilled (142-145° C., 20 mm Hg) to yield 2.07 g of a clear oil (66%) which solidified upon standing: $^1$H NMR (500 MHz, CDCl$_3$) δ 1.23 (d, J=3.7 Hz, 6H), 3.16 (m, 1H), 4.84 (s, 1H), 6.61 (d, J=8.6 Hz, 1H), 7.15 (d, J=11.0 Hz, 1H), 7.28 (s, 1H); $^{13}$C NMR (125 MHz, CDCl$_3$) δ 22.33, 27.17, 113.24, 116.99, 129.34, 129.50, 136.91, 151.81; LRMS (EI) (M+, 214/216).

4-bromo-2-isopropylanisole (12f). A solution of 4-bromo-2-isopropylphenol (12e) (15.0 g, 69.8 mmol), K$_2$CO$_3$ (48.2 g, 349 mmol, 5.0 eqv), and CH$_3$I (99.0 g, 698 mmol, 10.0 eqv.) in 200 ml of acetone was refluxed for 24 h. The mixture was filtered and concentrated in vacuo. Column chromatography [Hexanes/Et$_2$O (9/1)] yielded 14.5 g of a clear oil (91%): $^1$H NMR (500 MHz, CDCl$_3$) δ 1.18 (d, J=7.0 Hz, 6H), 3.27 (m, 1H), 3.79 (s, 3H), 6.70 (d, J=8.6 Hz, 1H), 7.24

(d, J=10.8 Hz, 1H), 7.28 (s, 1H); $^{13}$C NMR (125 MHz, CDCl$_3$) δ 22.46, 26.74, 55.52, 112.00, 113.02, 129.06, 129.10, 139.38, 155.85; LRMS (EI) (M+, 228/230).

3-(3-isobutyl-4-methoxyphenyl)propanenitrile (10i). 4-iodo-2-isobutylanisole (10) (1.92 g, 6.64 mmol), acrylonitrile (0.49 g, 9.29 mmol, 1.4 eqv), tetra-n-butylammonium chloride (1.85 g, 6.63 mmol, 1.0 eqv), NaHCO$_3$ (1.34 g, 15.9 mmol, 2.4 eqv), and Pd(OAc)$_2$ (10 mol %, 150 mg) were dissolved in 10 ml of DMF and the resulting solution was stirred at 40° C. for 19 h. The mixture was diluted with Et$_2$O, filtered, and concentrated in vacuo. Column chromatography [Hexanes/EtOAc (4/1)] yielded 1.06 g of a clear oil (74%). GC/MS showed a 2:1 ratio of trans/cis isomers: The oil was dissolved in 40 ml of anhydrous MeOH and the soln was cooled to 0° C. Mg turnings (4.79 g, 19.7 mmol, 40 eqv) were added very slowly and the suspension was allowed to stir for 5 h at rt. The reaction was cooled to 0° C. and 14 ml of 6 M HCl was added very slowly. The mixture was extracted with CHCl$_3$ and the organic fractions were combined, dried (MgSO$_4$), filtered, and concentrated in vacuo. Column chromatography [Hexanes/EtOAc (5/2)] yielded 1.03 g of a clear oil (96%): $^1$H NMR (500 MHz, CDCl$_3$) δ 0.93 (d, J=6.6 Hz, 6H), 1.94 (m, 1H), 2.50 (d, J=7.2 Hz, 2H), 2.58 (t, J=7.4 Hz, 2H), 2.89 (t, J=7.4 Hz, 2H), 3.81 (s, 3H), 6.82 (d, J=8.3 Hz, 1H), 6.97 (s, 1H), 7.05 (d, J=10.6 Hz, 1H); $^{13}$C NMR (125 MHz, CDCl$_3$) δ 19.52, 22.40, 28.51, 30.71, 39.28, 55.20, 110.42, 119.16, 126.39, 129.46, 130.52, 130.60, 156.76; HRMS (EI) Calcd for C$_{14}$H$_{19}$NO: 217.1467. Found 217.1468.

3-(4-hydroxy-3-isobutylphenyl)propanenitrile (10j). 3-(3-isobutyl-4-methoxyphenyl)propanenitrile (10i) (0.73 g, 3.36 mmol) was dissolved in 20 ml of CH$_2$Cl$_2$ and cooled to 0° C. BBr$_3$ (10.1 ml of a 1 M solution in CH$_2$Cl$_2$, 10.0 mmol, 3 eqv) was added slowly via syringe. The solution was allowed to stir for 9 h at 10° C. The reaction mixture was added to H$_2$O and extracted with CH$_2$Cl$_2$. The organic fractions were combined, dried (MgSO$_4$), filtered, and concentrated in vacuo. Column chromatography [Hexanes/EtOAc (2/1)] yielded 0.68 g of a clear oil (99%): $^1$H NMR (500 MHz, CDCl$_3$) δ 0.94 (d, J=6.6 Hz, 6H), 1.93 (m, 1H), 2.47 (d, J=7.0 Hz, 2H), 2.58 (t, J=7.4 Hz, 2H), 2.87 (t, J=7.4 Hz, 2H), 4.64 (s, 1H), 6.73 (d, J=8.8 Hz, 1H), 6.94 (m, 2H); $^{13}$C NMR (125 MHz, CDCl$_3$) δ 19.72, 22.50, 28.87, 30.87, 39.26, 115.62, 119.21, 126.81, 127.96, 130.09, 131.09, 152.84; HRMS (EI) Calcd for C$_{13}$H$_{17}$NO: 203.1310. Found 203.1306.

4-(2-cyanoethyl)-2-isobutylphenyltrifluoromethanesulfonate (6). 3-(4-hydroxy-3-isobutylphenyl)propanenitrile (10j) (0.67 g, 3.31 mmol) was dissolved in 3.5 ml of pyridine and cooled to 0° C. Triflic anhydride (1.12 g, 3.97 mmol, 1.2 eqv) was added slowly via syringe and the solution was allowed to stir for 17 h at rt. The reaction mixture was added to H$_2$O and extracted with Et$_2$O. The organic fractions were combined, dried (MgSO$_4$), filtered, and concentrated in vacuo. Column chromatography [Hexanes/EtOAc (1/1)] yielded 1.03 g of a clear oil (93%): $^1$H NMR (500 MHz, CDCl$_3$) δ 0.94 (d, J=7.3 Hz, 6H), 1.95 (m, 1H), 2.58 (d, J=7.2 Hz, 2H), 2.64 (t, J=7.3 Hz, 2H), 2.97 (t, J=7.3 Hz, 2H), 7.17 (m, 2H), 7.25 (d, J=15.4 Hz, 1H); $^{13}$C NMR (125 MHz, CDCl$_3$) δ 19.17, 22.26, 29.17, 30.95, 39.33, 114.83, 117.37, 118.48, 119.91, 121.72, 122.46, 127.52, 131.99, 135.01, 138.07, 147.47; HRMS (EI) Calcd for C$_{14}$H$_{16}$F$_3$NO$_3$S: 335.0803. Found 335.0807.

Figure 3:
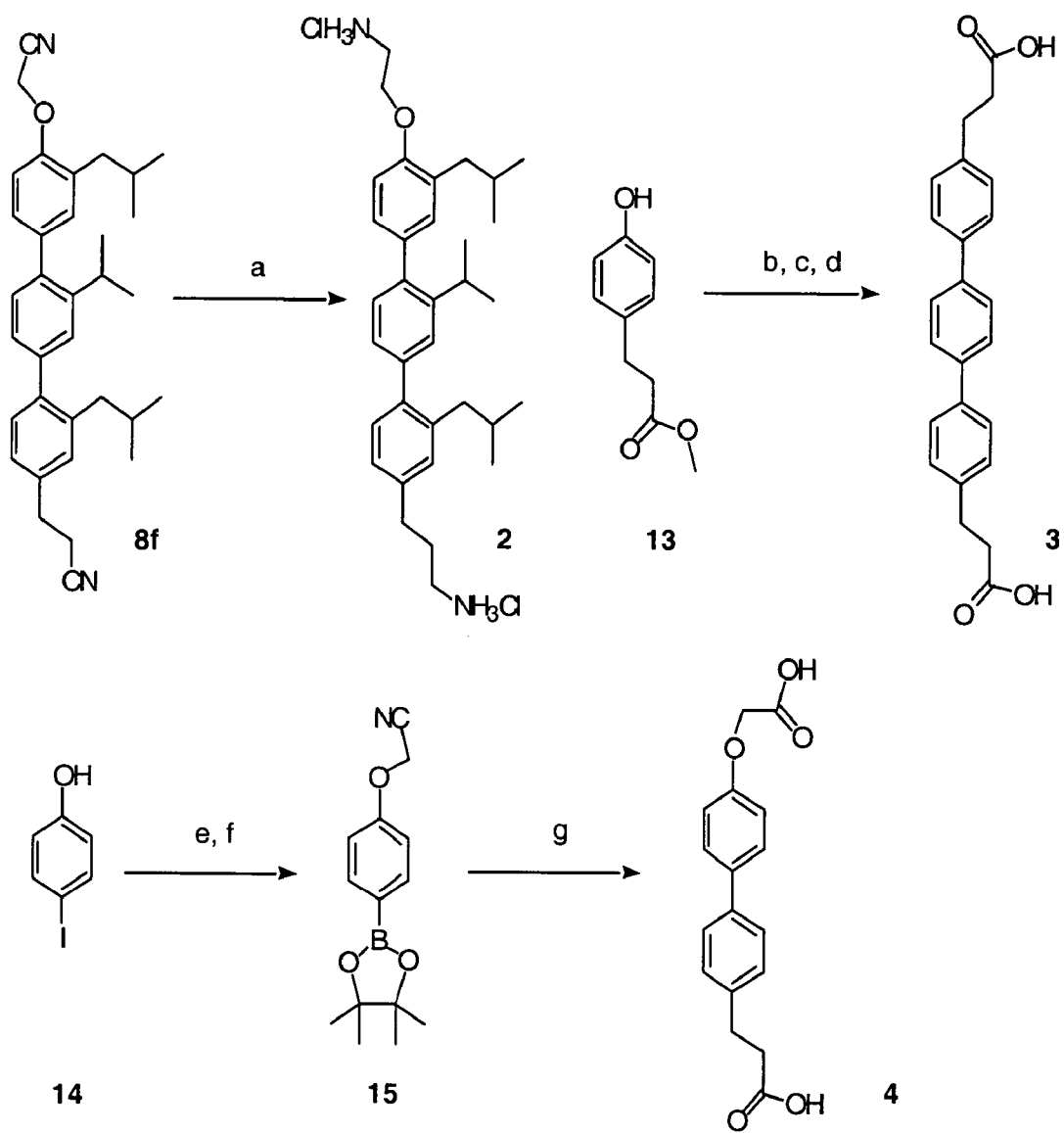
FIG. 3 is a scheme representing the chemical synthesis of terphenyl derivative 3 and biphenyl derivative 4. The following legend applies to FIG. 3, Scheme 3: a) $H_2$ (20 psi), 10% Pd/C, EtOH, rt, 12 h, 91%; b) $Tf_2O$, pyridine, 0° C.-rt, 48 h, 92%; c) 1,4-phenylenebisboronic acid, $Pd(PPh_3)_4$, $Na_2CO_3$ (aq), DME/EtOH, 80° C., 36 h, 79%; d) (i) NaOH, dioxane/$H_2O$/HMPA, 110° C., 2 h, (ii) HCl, 95%; e) $ClCH_2CN$, $K_2CO_3$, acetone, 45° C., 24 h, 66%; f) bis(pinacolato)diboron, KOAc, $PdCl_2dppf$, DMSO, 85° C., 16 h, 80%; g) (i) 4-bromophenylhydrocinnamonitrile, $Pd(PPh_3)_4$, $Na_2CO_3$ (aq), DME, 80° C., 24 h, (ii) NaOH, MeOH/$H_2O$, 50° C., 24 h, (iii) HCl, 93%.
Figure 11:
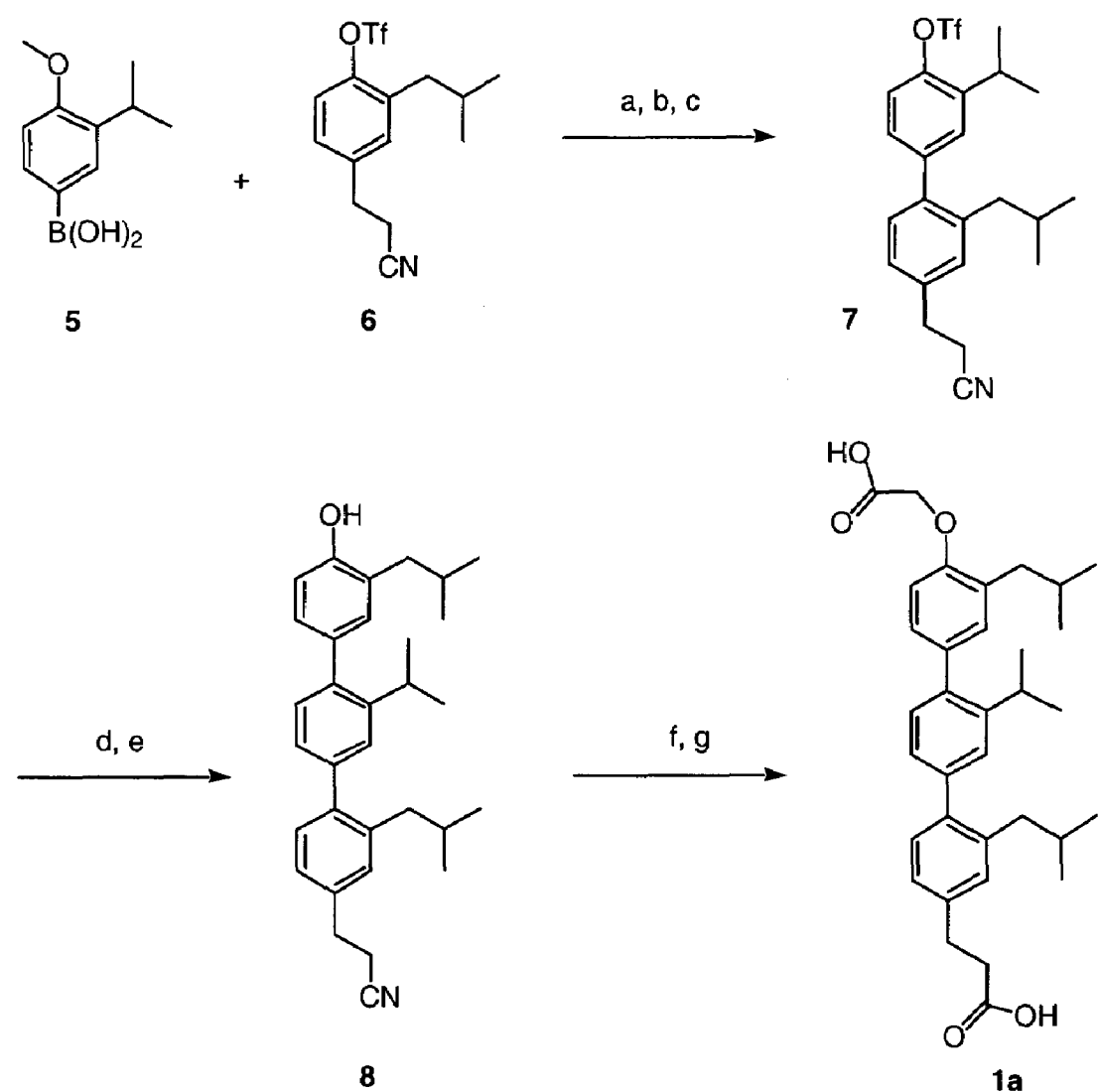
FIG. 11 represents a synthetic route to alternative terphenyl derivatives of the present invention. The following legend applies to FIG. 11: a) Pd(PPh$_3$)$_4$, Na$_2$CO$_3$ (aq), DME/EtOH, 80° C., 17 h, 98%; b) BBr$_3$, CH$_2$Cl$_2$, 0-10° C., 9 h, 92%; c) Tf$_2$O, pyridine, 0° C.-rt, 17 h, 95%; d) Pd(PPh$_3$)$_4$, 2-(3-isobutyl-4-methoxyphenyl)-4,4,5,5-tetramethyl-1,3,2-dioxaborolane, Na$_2$CO$_3$ (aq), DME/EtOH, 80° C., 20 h, 87%; e) BBr$_3$, CH$_2$Cl$_2$, 0-10° C., 9 h, 97%; f) CH$_2$ClCN, K$_2$CO$_3$, acetone, 55° C., 40 h, 95%; g) NaOH (aq), MeOH, 50° C., 24 h, 74%.

Synthesis Following the Presentation in FIG. 11, Scheme 11 and FIG. 3, Scheme 3

FIG. 11, Scheme 11

3-(2-isobutyl-3'-isopropyl-4'-methoxy-1,1'-biphenyl-4-yl)propanenitrile (6a). A solution of 4-bromo-2-isopropylanisole (12f) (6.0 g, 26.2 mmol) in 200 ml of THF was cooled to −78° C. To this solution was added n-BuLi (16.4 ml of 1.6 M solution in hexanes, 26.2 mmol, 1 eqv) via syringe and the mixture was stirred for 30 min. B(OMe)$_3$ (8.17 g, 78.6 mmol, 3.0 eqv) was then added and the solution was stirred for 24 h at rt. Water (20 ml) and 10% NaOH aq (50 ml) were added and stirring was continued for 1 h. The pH was adjusted to 4-5 (1 M HCl) and most of the solvent was removed in vacuo. The residue was taken up in EtOAc and the layers separated. The organic layer was dried (MgSO$_4$), filtered, and concentrated in vacuo to yield 4.81 g of a crude solid (95%). This material was used without further purification. The crude boronic acid (5) (0.081 g, 0.417 mmol, 1.4 eqv), 4-(2-cyanoethyl)-2-isobutylphenyl trifluoromethanesulfonate (6) (0.10 g, 0.30 mmol), and Pd(PPh$_3$)$_4$ (10 mol %, 33 mg) were dissolved in 4 ml of 9/1 DME/EtOH. Na$_2$CO$_3$ (0.3 ml of 2 M aq solution, 0.59 mmol, 2 eqv) was added via syringe and the solution was stirred at 80° C. for 17 h. The reaction mixture was concentrated in vacuo and taken up in 2:1 H$_2$O/CH$_2$Cl$_2$. The layers were separated and the H$_2$O layer was extracted further with CH$_2$Cl$_2$. The combined organic fractions were dried (MgSO$_4$), filtered, and concentrated in vacuo. Column chromatography [Hexanes/EtOAc (3/1)] yielded 0.098 g of a clear oil (98%): $^1$H NMR (500 MHz, CDCl$_3$) δ 0.76 (d, J=6.6 Hz, 6H), 1.22 (d, J=6.9 Hz, 6H), 1.69 (m, 1H), 2.48 (d, J=7.2 Hz, 2H), 2.67 (t, J=7.5 Hz, 2H), 2.99 (t, J=7.4 Hz, 2H), 3.37 (m, 1H), 3.88 (s, 3H), 6.88 (d, J=8.3 Hz, 1H), 7.08 (m, 4H), 7.18 (d, J=7.6 Hz, 1H); $^{13}$C NMR (125 MHz, CDCl$_3$) δ 19.39, 22.44, 22.79, 26.65, 29.58, 31.41, 42.26, 55.46, 109.99, 119.18, 125.31, 127.26, 127.30, 129.83, 130.76, 133.97, 136.37, 136.50, 140.05, 141.61, 155.69; HRMS (EI) Calcd for C$_{23}$H$_{29}$NO: 335.2249. Found 335.2252.

3-(4'-hydroxy-2-isobutyl-3'-isopropyl-1,1'-biphenyl-4-yl)propanenitrile (6b). 3-(2-isobutyl-3'-isopropyl-4'-methoxy-1,1'-biphenyl-4-yl)propanenitrile (6a) (0.56 g, 1.67 mmol) was dissolved in 25 ml of CH$_2$Cl$_2$ and cooled to 0° C. BBr$_3$ (5.0 ml of a 1 M solution in CH$_2$Cl$_2$, 5.0 mmol, 3 eqv) was added slowly via syringe. The solution was allowed to stir for 9 h at 10° C. The reaction mixture was added to H$_2$O and extracted with CH$_2$Cl$_2$. The organic fractions were combined, dried (MgSO$_4$), filtered, and concentrated in vacuo. Column chromatography [Hexanes/EtOAc (2/1)] yielded 0.49 g of a clear oil (92%): $^1$H NMR (500 MHz, CDCl$_3$) δ 0.76 (d, J=6.6 Hz, 6H), 1.26 (d, J=7 Hz, 6H), 1.68 (m, 1H), 2.48 (d, J=7.2 Hz, 2H), 2.67 (t, J=7.5 Hz, 2H), 2.98 (t, J=7.4 Hz, 2H), 3.26 (m, 1H), 4.76 (s, 1H), 6.78 (d, J=8.1 Hz, 1H), 6.95 (d, J=8.1 Hz, 1H), 7.09 (m, 3H), 7.17 (d, J=7.7 Hz, 1H); $^{13}$C NMR (125 MHz, CDCl$_3$) δ 19.39, 22.43, 22.67, 27.01, 29.58, 31.39, 42.25, 114.93, 119.17, 125.32, 127.49, 127.61, 129.86, 130.73, 133.91, 134.48, 136.42, 140.02, 141.47, 151.60; HRMS (EI) Calcd for C$_{22}$H$_{27}$NO: 321.2093. Found 321.2095.

4'-(2-cyanoethyl)-2'-isobutyl-3-isopropyl-1,1'-biphenyl-4-yl trifluoromethanesulfonate (7). 3-(4'-hydroxy-2-isobutyl-3'-isopropyl-1,1'-biphenyl-4-yl)propanenitrile (6b) (0.48 g, 1.48 mmol) was dissolved in 7.0 ml of pyridine and cooled to 0° C. Triflic anhydride (0.502 g, 1.78 mmol, 1.2 eqv) was added slowly via syringe and the solution was allowed to stir for 17 h at rt. The reaction mixture was added to H$_2$O and extracted with Et$_2$O. The organic fractions were combined, dried (MgSO$_4$), filtered, and concentrated in vacuo. Column chromatography [Hexanes/EtOAc (3/1)] yielded 0.639 g of a clear oil (95%): $^1$H NMR (500 MHz, CDCl$_3$) δ 0.75 (d, J=6.6 Hz, 6H), 1.29 (d, J=6.9 Hz, 6H), 1.64 (m, 1H), 2.45 (d, J=7.2 Hz, 2H), 2.68 (t, J=7.4 Hz, 2H), 2.99 (t, J=7.3 Hz, 2H), 3.35 (m, 1H), 7.16 (m, 4H), 7.28 (d, J=8.4 Hz, 1H), 7.31 (s, 1H); $^{13}$C NMR (125 MHz, CDCl$_3$)

δ 19.29, 22.27, 23.07, 27.07, 29.67, 31.22, 42.04, 114.79, 117.32, 119.02, 119.87, 120.73, 122.42, 125.57, 128.29, 128.83, 130.07, 130.27, 137.40, 139.67, 139.72, 140.64, 142,15, 145.89; HRMS (EI) Calcd for $C_{23}H_{26}F_3NO_3S$: 453.1586. Found 453.1594.

3-(2,3"-diisobutyl-3'-isopropyl-4"-methoxy-1,1':4',1"-terphenyl-4-yl)propane nitrile (7d). 2-(3-isobutyl-4-methoxyphenyl)-4,4,5,5-tetramethyl-1,3,2-dioxaborolane (11) (0.076 g, 0.26 mmol, 1.2 eqv), 4'-(2-cyanoethyl)-2'-isobutyl-3-isopropyl-1,1'-biphenyl-4-yl trifluoromethanesulfonate (7) (0.099 g, 0.22 mmol), and $Pd(PPh_3)_4$ (15 mol %, 37 mg) were dissolved in 4 ml of 9/1 DME/EtOH. $Na_2CO_3$ (0.22 ml of 2 M aq solution, 0.44 mmol, 2 eqv) was added via syringe and the solution was stirred at 80° C. for 20 h. The reaction mixture was concentrated in vacuo and taken up in 2:1 $H_2O/CH_2Cl_2$. The layers were separated and the $H_2O$ layer was extracted further with $CH_2Cl_2$. The combined organic fractions were dried ($MgSO_4$), filtered, and concentrated in vacuo. Column chromatography [Hexanes/EtOAc (6/1)] yielded 0.089 g of a clear oil (87%): $^1H$ NMR (500 MHz, $CDCl_3$) δ 0.79 (d, J=6.6 Hz, 6H), 0.94 (d, J=6.6 Hz, 6H), 1.17 (d, J=6.9 Hz, 6H), 1.74 (m, 1H), 1.97 (m, 1H), 2.54 (m, 4H), 2.69 (t, J=7.5 Hz, 2H), 3.01 (t, J=7.4 Hz, 2H), 3.17 (m, 1H), 3.88 (s, 3H), 6.91 (d, J=8.3 Hz, 1H), 7.17 (m, 8H); $^{13}C$ NMR (125 MHz, $CDCl_3$) δ 19.37, 22.46, 22.58, 24.28, 28.62, 29.37, 29.65, 31.44, 39.59, 42.23, 55.39, 109.89, 119.15, 125.38, 126.21, 126.69, 127.63, 129.66, 129.79, 129.87, 130.64, 132.06, 133.68, 136.62, 139.54, 139.94, 140.52, 141.71, 146.13, 156.72; HRMS (EI) Calcd for $C_{33}H_{41}NO$: 467.3188. Found 467.3194.

3-(4"-hydroxy-2,3"-diisobutyl-3'-isopropyl-1,1':4',1"-terphenyl-4-yl)propanenitrile (8). 3-(2,3"-diisobutyl-3'-isopropyl-4"-methoxy-1,1':4',1"-terphenyl-4-yl)propane nitrile (7d) (0.076 g, 0.16 mmol) was dissolved in 4 ml of $CH_2Cl_2$ and cooled to 0° C. $BBr_3$ (0.49 ml of a 1 M solution in $CH_2Cl_2$, 0.49 mmol, 3.0 eqv) was added slowly via syringe. The solution was allowed to stir for 9 h at 10° C. The reaction mixture was added to $H_2O$ and extracted with $CH_2Cl_2$. The organic fractions were combined, dried ($MgSO_4$), filtered, and concentrated in vacuo. Column chromatography [Hexanes/EtOAc (3/1)] yielded 0.072 g of a clear oil (97%): $^1H$ NMR (500 MHz, $CDCl_3$) δ 0.80 (d, J=6.6 Hz, 6H), 0.99 (d, J=6.6 Hz, 6H), 1.17 (d, J=6.9 Hz, 6H), 1.74 (m, 1H), 2.00 (m, 1H), 2.54 (m, 4H), 2.69 (t, J=7.5 Hz, 2H), 3.01 (t, J=7.4 Hz, 2H), 3.16 (m, 1H), 4.70 (s, 1H), 6.83 (d, J=8.6 Hz, 1H), 7.09 (m, 5H), 7.19 (d, J=7.7 Hz, 1H), 7.25 (m, 2H); $^{13}C$ NMR (125 MHz, $CDCl_3$) δ 19.42, 22.46, 22.56, 24.29, 28.81, 29.34, 29.67, 31.39, 39.42, 42.17, 114.86, 119.23, 125.39, 126.22, 126.69, 126.89, 128.01, 129.75, 129.89, 130.62, 132.33, 134.17, 136.63, 139.31, 139.89, 140.55, 141.61, 146.06, 152.58; HRMS (EI) Calcd for $C_{32}H_{39}NO$: 453.3031. Found 453.3025.

FIG. 3, Scheme 3

3-[4"-(cyanomethoxy)-2,3"-diisobutyl-3'-isopropyl-1,1':4',1"-terphenyl-4-yl]propanenitrile (8f). To a solution of 3-(4"-hydroxy-2,3"-diisobutyl-3'-isopropyl-1,1':4', 1"-terphenyl-4-yl)propanenitrile (8) (18.6 mg, 0.04 mmol) and $K_2CO_3$ (28.0 mg, 0.20 mmol, 5.0 eqv) in 2.0 ml of acetone was added $ClCH_2CN$ (31.0 mg, 0.41 mmol, 10.0 eqv) via syringe. The solution was stirred for 40 h at 55° C. and was then added to 20 ml of 1:1 $H_2O$/brine. The mixture was extracted with EtOAc and the combined organic fractions were washed (brine), dried ($MgSO_4$), filtered, and concentrated in vacuo. Column chromatography [Hexanes/EtOAc (3/1)] yielded 19.2 mg of a clear oil (95%): $^1H$ NMR (500 MHz, $CDCl_3$) δ 0.80 (d, J=6.6 Hz, 6H), 0.95 (d, J=6.6 Hz, 6H), 1.18 (d, J=6.8 Hz, 6H), 1.75 (m, 1H), 1.95 (m, 1H), 2.55 (m, 4H), 2.70 (t, J=7.5 Hz, 2H), 3.01 (t, J=7.4 Hz, 2H), 3.12 (m, 1H), 4.86 (s, 2H), 6.98 (d, J=8.4 Hz, 1H), 7.18 (m, 8H); $^{13}C$ NMR (125 MHz, $CDCl_3$) δ 19.43, 22.44, 22.49, 24.27, 28.87, 29.32, 29.66, 31.30, 39.27, 42.07, 53.65, 111.09, 115.41, 119.25, 125.39, 126.26, 126.73, 127.85, 129.60, 129.89, 130.49, 130.56, 132.76, 136.14, 136.65, 138.65, 139.81, 140.79, 141.37, 145.93, 153.58; HRMS (EI) Calcd for $C_{34}H_{40}N_2O$: 492.3140. Found 492.3131.

3-[4"-(carboxymethoxy)-2,3"-diisobutyl-3'-isopropyl-1,1':4',1"-terphenyl-4-yl]propanoic acid (1a). 3-[4"-(cyanomethoxy)-2,3"-diisobutyl-3'-isopropyl-1,1':4',1"-terphenyl-4-yl]propanenitrile (8f) (19.2 mg, 0.039 mmol) was dissolved in a solution containing 2 ml of 25% NaOH (aq) and 3.5 ml of MeOH. The mixture was stirred at 50° C. for 24 h. The temperature was then reduced to 0° C. and the solution was acidified to pH 2 with 1N HCl. The mixture was partitioned between EtOAc and brine and the organic layer was separated, dried ($MgSO_4$), filtered, and concentrated in vacuo. Prep TLC [Hexanes/EtOAc/AcOH (66/33/1)] yielded 15.3 mg of a white solid (74%): $^1H$ NMR (500 MHz, $CDCl_3$) δ 0.77 (d, J=6.6 Hz, 6H), 0.96 (d, J=6.6 Hz, 6H), 1.15 (d, J=6.8 Hz, 6H), 1.72 (m, 1H), 2.00 (m, 1H), 2.51 (d, J=7.2 Hz, 2H), 2.60 (d, J=7.1 Hz, 2H), 2.77 (t, J=7.6 Hz, 2H), 3.01 (t, J=7.4 Hz, 2H), 3.12 (m, 1H), 4.75 (s, 2H), 6.79 (d, J=8.9 Hz, 1H), 7.13 (m, 8H); $^{13}C$ NMR (125 MHz, $CDCl_3$) δ 22.44, 22.57, 24.31, 28.78, 29.36, 29.65, 30.29, 35.33, 39.58, 42.17, 65.23, 110.89, 125.49, 126.32, 126.75, 126.83, 127.82, 129.67, 130.08, 130.26, 132.59, 135.28, 138.67, 138.81, 139.40, 140.64, 140.94, 145.90, 154.48, 172.99, 177.73; HRMS (EI) Calcd for $C_{34}H_{42}O_5$: 530.3032. Found 530.3031.

Synthesis Following the Presentation in FIG. 3, Scheme 3

3-[4"-(2-aminoethoxy)-2,3"-diisobutyl-3'-isopropyl-1,1':4',1"-terphenyl-4-yl]propan-1-amine dihydrochloride (2). 3-[4"-(cyanomethoxy)-2,3"-diisobutyl-3'-isopropyl-1,1':4',1"-terphenyl-4-yl]propanenitrile (8f) (19.0 mg, 0.038 mmol) was dissolved in 5 ml of EtOH containing 10% Pd/C (15 mg) and 0.1 ml HCl (conc.). The solution was stirred overnight under 20 psi of $H_2$. The reaction mixture was filtered through celite and the filtrate was concentrated in vacuo to yield 20 mg of a white solid (91%): $^1H$ NMR (500 MHz, $CD_3OD$) δ 0.75 (d, J=6.6 Hz, 6H), 0.93 (d, J=6.9 Hz, 6H), 1.14 (d, J=6.9, 6H), 1.68 (m, 2H), 1.96 (m, 1H), 1.99 (m, 1H), 2.54 (d, J=6.6 Hz, 2H), 2.62 (d, J=6.9 Hz, 2H), 2.76 (t, J=7.4, 2H), 2.96 (t, J=6.8 Hz, 2H), 3.11 (m, 1H), 3.41 (t, J=4.5 Hz, 2H), 4.29 (t, J=5.0 Hz, 2H), 7.13 (m, 9H); $^{13}C$ NMR (125 MHz, $CD_3OD$) δ 22.85, 22.96, 24.61, 30.15, 30.53, 30.54, 30.81, 33.34, 40.12, 40.53, 40.70, 43.42, 66.06, 112.90, 126.84, 127.50, 127.67, 129.06, 130.75, 131.25, 131.29, 131.33, 133.29, 136.26, 140.46, 140.49, 140.59, 141.95, 142.56, 147.13, 156.52; HRMS (FAB, M+H) Calcd for $C_{34}H_{49}N_2O$: 501.3845. Found 501.3845.

Methyl-3-(4-{[(trifluoromethyl)sulfonyl]oxy}phenyl)propanoate (13b). Methyl 3-(4-hydroxyphenyl)propanoate (13) (1.0 g, 5.5 mmol) was dissolved in 5 ml of pyridine at 0° C. Triflic anhydride (1.1 ml, 6.6 mmol, 1.2 eqv) was added and the solution was allowed to stir for 48 h at rt. The reaction mixture was added to $H_2O$ and extracted with $Et_2O$. The organic fractions were combined, dried ($MgSO_4$), filtered, and concentrated in vacuo. Column chromatography [Hexanes/EtOAc (2/1)] yielded 1.60 g of a clear oil (92%): $^1H$ NMR (400 MHz, $CDCl_3$) δ 2.64 (t, J=8.0 Hz, 2H), 2.98 (t, J=7.2 Hz, 2H), 3.67 (s, 3H), 7.19 (d, J=8.8 Hz, 2H), 7.28 (d, J=8.4 Hz, 2H); $^{13}C$ NMR (125 MHz, $CDCl_3$) δ 30.12, 35.20, 51.66, 114.88, 117.43, 119.98, 121.29, 122.53, 130.07, 141.10, 148.04, 172.77; HRMS (EI) Calcd for $C_{11}H_{11}F_3O_5S$: 312.0279. Found 312.0275.

Bis methyl 3-(1,1':4',1"-terphenyl-4,4"-yl)propanoate (13c). Methyl-3-(4-{[(trifluoromethyl)sulfonyl]oxy}phenyl)propanoate (13b) (188 mg, 0.60 mmol, 2.0 eqv), 1,4-phenylenebisboronic acid (50 mg, 0.30 mmol), and Pd(PPh$_3$)$_4$ (30 mol %, 100 mg) were dissolved in 7 ml of 6/1 DME/EtOH. Na$_2$CO$_3$ (0.6 ml of 2 M aq solution, 1.2 mmol, 4.0 eqv) was added via syringe and the solution was stirred at 80° C. for 36 h. The reaction mixture was concentrated in vacuo. Column chromatography [Hexanes/EtOAc/CH$_2$Cl$_2$ (2/1/1)] yielded 0.095 g of a white solid (79%): $^1$H NMR (400 MHz, CDCl$_3$) δ 2.55 (t, J=8.0 Hz, 4H), 2.88 (t, J=7.2 Hz, 4H), 3.56 (s, 6H), 7.16 (d, J=8.0 Hz, 4H), 7.43 (d, J=7.6 Hz, 4H), 7.52 (s, 4H); $^{13}$C NMR (125 MHz, CDCl$_3$) δ 30.54, 35.59, 51.64, 127.07, 127.28, 128.73, 138.68, 139.64, 139.66, 173.29; HRMS (EI) Calcd for $C_{26}H_{26}O_4$: 402.1831. Found 402.1832.

Bis methyl 3-(1,1':4',1"-terphenyl-4,4"-yl)propanoic acid (3). Bis methyl 3-(1,1':4', 1"-terphenyl-4,4"-yl)propanoate (13c) (23 mg, 0.06 mmol) was dissolved in 5 ml of a 3/1/1 mixture of dioxane/HMPA/H$_2$O. NaOH (0.3 ml of a 25% aq solution) was added and the mixture was stirred at 110° C. for 2 h. The reaction was cooled to rt, added to H$_2$O, and acidified to pH 1.0 with 1 N HCl. The mixture was extracted with EtOAc and the organics were combined, washed with H$_2$O, dried (MgSO$_4$), filtered, and concentrated in vacuo. The resulting solid was washed several times with CH$_2$Cl$_2$ and then sufficiently dried to yield 20 mg of the purified product as a white solid (95%): $^1$H NMR (400 MHz, DMSO) δ 2.58 (t, J=7.6 Hz, 4H), 2.87 (t, J=7.2 Hz, 4H), 7.34 (d, J=8 Hz, 4H), 7.63 (d, J=8 Hz, 4H), 7.73 (s, 4H); $^{13}$C NMR (125 MHz, DMSO) δ 29.86, 34.99, 126.35, 126.84, 128.79, 137.27, 138.68, 140.15, 173.64; LRMS (ESI) (M+, 374.4).

(4-iodophenoxy)acetonitrile (14e). 4-iodophenol (14) (2.0 g, 9.1 mmol), chloroacetonitrile (5.75 ml, 91 mmol, 10 eqv), and K$_2$CO$_3$ (6.28 g, 45.5 mmol, 5 eqv) were added to 20 ml of acetone. The mixture was stirred at 45° C. for 24 h. The mixture was then added to 1/1 H$_2$O/brine and extracted with EtOAc. The organics were combined, washed with brine, dried (MgSO$_4$), filtered, and concentrated in vacuo. Column chromatography [Hexanes/EtOAc (2/1)] yielded 1.55 g of a white solid (66%): $^1$H NMR (400 MHz, CDCl$_3$) δ 4.74 (s, 2H), 6.77 (d, J=7.2 Hz, 2H), 7.64 (d, J=7.2 Hz, 2H); $^{13}$C NMR (125 MHz, CDCl$_3$) δ 53.59, 85.85, 114.69, 117.25, 138.74, 156.38; HRMS (EI) Calcd for $C_8H_6INO$: 258.9494. Found 258.9505.

[4-(4,4,5,5-tetramethyl-1,3,2-dioxaborolan-2-yl)phenoxy]acetonitrile (15). A solution of (4-iodophenoxy)acetonitrile (14e) (0.30 g, 1.16 mmol), bis(pinacolato)diboron (0.32 g, 1.27 mmol, 1.1 eqv), KOAc (0.34 g, 3.47 mmol, 3.0 eqv), and PdCl$_2$dppf (5 mol %, 47 mg) in 4 ml of DMSO was stirred at 85° C. for 16 h. The mixture was added to H$_2$O and extracted with CH$_2$Cl$_2$. The organic fractions were combined, back extracted with H$_2$O, dried (MgSO$_4$), filtered, and concentrated in vacuo. Column chromatography [Hexanes/EtOAc (2/1)] yielded 0.241 g of a white solid (80%): $^1$H NMR (400 MHz, CDCl$_3$) δ 1.34 (s, 12H), 4.79 (s, 2H), 6.97 (d, J=8.4 Hz, 2H), 7.81 (d, J=8.0 Hz, 2H); $^{13}$C NMR (125 MHz, CDCl$_3$) δ 24.85, 53.18, 83.80, 114.03, 114.89, 136.79, 158.89; HRMS (EI) Calcd for $C_{14}H_{18}BNO_3$: 258.1416. Found 258.1412.

3-[4'-(carboxymethoxy)-1,1'-biphenyl-4-yl)propanoic acid (4). [4-(4,4,5,5-tetramethyl-1,3,2-dioxaborolan-2-yl)phenoxy]acetonitrile (15) (55 mg, 0.21 mmol), 4-bromophenylhydrocinnamonitrile (44 mg, 0.21 mmol, 1 eqv), and Pd(PPh$_3$)$_4$ (5 mol %, 12 mg) were dissolved in 3 ml of DME. Na$_2$CO$_3$ (0.21 ml of 2 M aq solution, 0.42 mmol, 2 eqv) was added via syringe and the solution was stirred at 80° C. for 20 h. The reaction mixture was concentrated in vacuo and taken up in 2:1 H$_2$O/CH$_2$Cl$_2$. The layers were separated and the water layer was extracted further with CH$_2$Cl$_2$. The combined organic fractions were dried (MgSO$_4$), filtered, and concentrated in vacuo to yield a white solid. The crude solid was dissolved in 3/1 MeOH/dioxane. NaOH (1.5 ml of a 25% aq solution) was added and the mixture was stirred vigorously at 50° C. for 24 h. The solution was acidified to pH 1.0 with 1N HCl and extracted with EtOAc several times. The organics were combined, dried (MgSO$_4$), filtered, and concentrated in vacuo to yield a white solid. This material was washed several times with CH$_2$Cl$_2$ to yield 59 mg of purified product (93%): $^1$H NMR (400 MHz, DMSO) δ 2.56 (t, J=7.2 Hz, 2H), 2.84 (t, J=7.2 Hz, 2H), 4.71 (s, 2H), 6.98 (d, J=8.8 Hz, 2H), 7.28 (d, J=8.4 Hz, 2H), 7.52 (d, J=8.0 Hz, 2H), 7.56 (d, J=8.8 Hz, 2H); $^{13}$C NMR (125 MHz, DMSO) δ 29.84, 35.07, 64.41, 114.75, 126.05, 127.46, 128.69, 132.66, 137.42, 139.37, 157.13, 170.10, 173.68; HRMS (EI) Calcd for $C_{17}H_{16}O_5$: 300.0998. Found 300.1003.

Figure 4:
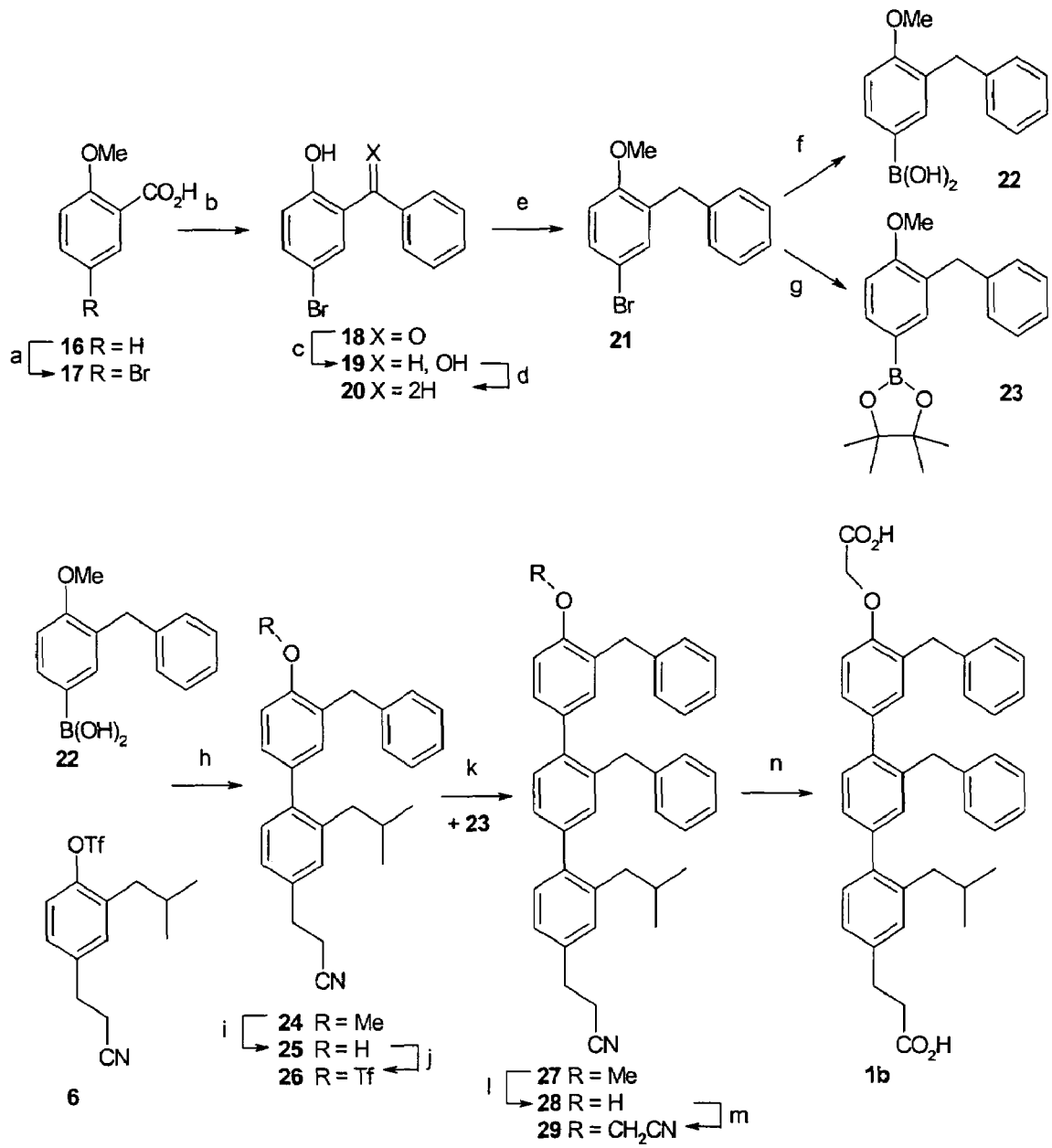
FIG. 4, is a scheme representing the chemical synthesis of terphenyl derivatives as depicted. The following legend applies to FIG. 4, Scheme 4: a) Br$_2$, CH$_2$Cl$_2$/H$_2$O, rt, 19 h, 92%; b) SOCl$_2$, toluene, DMF, 70° C., 1.5 h, (ii) AlCl$_3$, benzene, rfl., 5 h, 90%; c) NaBH$_4$, MeOH, rt, 2 h, 98%; d) (i) LiAlH$_4$, AlCl$_3$, Et$_2$O, rfl., 12 h, 62%; e) MeI, K$_2$CO$_3$, acetone, rfl., 24 h, 98%; f) (i) n-BuLi, THF, −78° C., 30 min, (ii) B(OMe)$_3$, rt, 24 h, (iii) H$_2$O, 10% aq. NaOH, rt, 1 h; g) bis(pinacolato)diboron, KOAc, PdCl$_2$dppf*CH$_2$Cl$_2$, DMSO, 85° C., 3 h, 55%; h) Pd(Ph$_3$P)$_4$, DME/EtOH (9+1), 2 M aq. Na$_2$CO$_3$, 80° C., 17 h, 52%; i) BBr$_3$, CH$_2$Cl$_2$, 0° C.-rt, 9 h, 96%; j) Tf$_2$O, Py, 0° C.-rt, 18 h, 85%; k) 23, Pd(Ph$_3$P)$_4$, DME/EtOH (9+1), 2 M aq. Na$_2$CO$_3$, 80° C., 8 h, 91%; 1) BBr$_3$, CH$_2$Cl$_2$, 0° C.-rt, 6 h, 86%; m) K$_2$CO$_3$, acetone, ClCH$_2$CN, 55° C., 40 h, 97%; n) 25% aq. NaOH, MeOH/THF (1:1), rfl., 24 h, 11%.

Synthesis Following the Presentation in FIG. 4, Scheme 4

5-Bromo-2-methoxy-benzoic acid (17). 6.42 ml (125 mmol, 1.1 eqv) Br$_2$ was added to a solution of 17.50 g (115 mmol) 2-Methoxy-benzoic acid (16) in 220 ml CH$_2$Cl$_2$H$_2$O (1:1) and the resulting mixture was stirred at rt for 19 h. After adding 1.32 g NaHSO$_3$ (12.7 mmol, 0.11 eq) the aq. layer was extracted with CH$_2$Cl$_2$. The comb. org. fractions were dried over MgSO$_4$ and the solvent was evaporated. The resulting white solid was suspended in 45 ml CH$_2$Cl$_2$ and treated with 450 ml ice-cold hexanes. The obtained white residue was filtered, washed with ice-cold hexanes and dried in high vacuum. This led to 24.53 g (106 mmol, 92%) 17: $^1$H NMR (500 MHz, CDCl$_3$) δ 4.10 (s, 3H), 6.96 (d, 1H, J=8.83 Hz), 7.67 (dd, 1H, J$_1$=8.83 Hz, J$_2$=2.52 Hz), 8.31 (d, 1H, J=2.68 Hz), 11.91 (s, 1H), 10.50 (s, br., 1H).

(5-bromo-2-hydroxy-phenyl)-phenyl-methanone (18). 10.07 ml (138.8 mmol, 2.2 eqv) SOCl$_2$ was added to a solution of 14.77 g (63.9 mmol) 5-Bromo-2-methoxy-benzoic acid (17) in 140 ml dry toluene, followed by 0.5 ml (6.5 mmol, 0.1 eqv) DMF. After stirring this solution for 1.5 h at 70° C. the solvent was evaporated and the the crude acyl chloride was dissolved in 75 ml of dry benzene. This solution was then added cautiously under stirring to a suspension of 10.30 g (77.3 mmol, 1.2 eqv) AlCl$_3$ in 80 ml dry benzene at 10° C. After complete addition the resulting mixture was refluxed for 5 h and then quenched by adding H$_2$O and conc. hydrochloric acid. The aq. layer was extracted with EtOAc and the comb. org. fractions were dried over NaSO$_4$ and evaporated. Column chromatography (CH$_2$Cl$_2$) yielded 16.03 g (57.9 mmol, 90%) 18 as a yellow solid: R$_f$(CH$_2$Cl$_2$) 0.67; $^1$H NMR (500 MHz, CDCl$_3$) δ 6.99 (d, 1H, J=8.99 Hz), 7.52-7.68 (m, 6H), 7.70 (d, 1H, J=2.36 Hz), 11.91 (s, 1H); LRMS (EI) m/z 278 (80), 277 (100), 276 (86), 275 (92), 201 (31), 200 (22), 199 (30), 198 (20), 105 (63), 77 (57), 63 (19); HRMS (EI) Calcd. for $C_{13}H_9BrO_2$: 275.978591. Found: 275.977717.

4-bromo-2-(hydroxy-phenyl-methyl)-phenol (19). 1.02 g (27 mmol, 3.9 eqv) NaBH$_4$ was added cautiously at rt to a solution of 1.92 g (6.9 mmol) (5-Bromo-2-hydroxy-phenyl)-phenyl-methanone (18) in 70 ml dry MeOH. After stirring this solution for 2 h at rt the solvent was evaporated and the residue was taken up in 70 ml water and 70 ml Et$_2$O. The aq. layer was extracted with Et$_2$O and the comb. org. fractions were washed twice with water, dried over Na$_2$SO$_4$ and evaporated. Column chromatography (Hexanes/EtOAc (1+1)) yielded 1.88 g (6.7 mmol, 98%) 19 as a white solid: R$_f$ (Hexanes/EtOAc (1+1)) 0.57; mp 96-97° C.; $^1$H NMR (500 MHz, CDCl$_3$) δ 2.76 (d, 1H, J=3.15 Hz), 5.98 (d, 1H, J=3.00 Hz), 6.79 (d, 1H, J=8.67 Hz), 6.98 (dd, 1H, J$_1$=2.21 Hz, J$_2$=0.47 Hz), 7.28 (dd, 1H, J$_1$=8.67 Hz, J$_2$=2.36 Hz), 7.33-7.41 (m, 5H), 7.92 (s, 1H); LRMS (EI) m/z 278 (5), 276 (4), 262 (56), 261 (100), 260 (46), 259 (95), 181 (21), 180 (12), 153 (12), 152 (33), 77 (16), 76 (16), 63 (10); HRMS (EI) Calcd. for C$_{13}$H$_{11}$BrO$_2$: 277.994241. Found: 277.993366.

2-benzyl-4-bromo-phenol (20). A solution of 13.24 g (99.3 mmol, 4.1 eqv) AlCl$_3$ in 85 ml dry Et$_2$O was added cautiously under stirring to a suspension of 3.91 g (102.9 mmol, 4.2 eqv) LiAlH$_4$ in 100 ml dry Et$_2$O. After complete addition the resulting mixture was stirred for 30 min at rt and then a solution of 6.85 g (24.5 mmol) 4-Bromo-2-(hydroxy-phenyl-methyl)-phenol (19) in 80 ml dry Et$_2$O was added dropwise. The mixture was refluxed for 12 h and after that cooled to 0° C. After adding cautiously 60 ml of a mixture of Et$_2$O/MeOH (1:1), 170 ml 1 N HCl-solution was added and the mixture was extracted with Et$_2$O. The comb. org. fractions were washed with brine, dried over Na$_2$SO$_4$ and evaporated. Column chromatography (CH$_2$Cl$_2$) yielded 4.00 g (15.2 mmol, 62%) 20 as a colorless liquid: R$_f$ (CH$_2$Cl$_2$) 0.41; $^1$H NMR (500 MHz, CDCl$_3$) δ 3.95 (s, 2H), 4.64 (s, 1H), 6.67 (dd, 1H, J$_1$=8.04 Hz, J$_2$=0.79 Hz), 7.23 (m, 5H), 7.31 (m, 2H); LRMS (EI) m/z 265 (17), 264 (98), 263 (21), 262 (100), 186 (53), 184 (49), 183 (78), 182 (18), 181 (27), 165 (49), 153 (23), 152 (26), 91 (29), 84 (14), 78 (25), 77 (31), 76 (16), 63 (15); HRMS (EI) Calcd. for C$_{13}$H$_{11}$BrO: 261.999326. Found: 261.998568.

2-benzyl-4-bromo-anisole (21). 9.48 ml (152 mmol, 10 eqv) iodomethane was added to a suspension of 4.00 g (15.2 mmol) 2-Benzyl-4-bromo-phenol (20) and 10.50 g (76 mmol, 5 eqv) K$_2$CO$_3$ in 70 ml acetone and the resulting mixture was refluxed for 24 h. After adding water and aq. NH$_3$-solution, the aq. layer was extracted with Et$_2$O. The comb. org. fractions were washed with brine, dried over Na$_2$SO$_4$ and evaporated. Column chromatography (CH$_2$Cl$_2$) yielded 4.11 g (14.8 mmol, 98%) 21 as a colorless liquid: R$_f$ (CH$_2$Cl$_2$) 0.77; $^1$H NMR (400 MHz, CDCl$_3$) δ 3.79 (s, 3H), 3.92 (s, 2H), 6.72 (d, 1H, J=8.59 Hz), 7.18 (m, 4H), 7.27 (m, 3H); LRMS (EI) m/z 279 (17), 278 (95), 277 (18), 276 (96), 263 (14), 261 (17), 198 (18), 197 (65), 182 (34), 181 (31), 166 (20), 165 (56), 154 (19), 153 (24), 152 (29), 92 (11), 91 (100), 77 (13), 76 (16), 63 (13); HRMS (EI) Calcd. for C$_{14}$H$_{13}$BrO: 276.014976. Found: 276.014234.

3-benzyl-4-methoxy-benzene-1-boronic acid (22). 8.61 ml (13.8 mmol, 1 eqv) of a 1.6 M solution of n-BuLi in hexanes was added to a solution of 3.82 g (13.8 mmol) 2-Benzyl-4-bromo-anisol (21) in 100 ml dry THF at −78° C. After stirring this mixture for 30 min at −78° C., 4.70 ml (41.4 mmol, 3 eqv) B(OMe)$_3$ was added and the solution was stirred for 24 h at rt. Now 10 ml water and 25 ml of a 10% aq. NaOH-solution were added and stirring was continued for further 60 min. Then the pH was adjusted to 4-5 with 1-N-HCl-solution and most of the solvent was evaporated. The residue was extracted with EtOAc and the comb. org. fractions were dried over MgSO$_4$ and evaporated, which led after drying in high vacuum to 3.33 g (13.8 mmol, 100%) of an orange solid. This crude boronic acid 22 was used without further purification: $^1$H NMR (500 MHz, CDCl$_3$) δ 3.81 (s, 3H), 3.98 (s, 2H), 6.89 (d, 1H, J=8.20 Hz), 7.10-7.23 (m, 5H), 7.79 (d, 1H, J=1.58 Hz), 7.96 (dd, 1H, J$_1$=8.20 Hz, J$_2$=1.73 Hz).

2-(3-benzyl-4-methoxy-phenyl)-4,4,5,5-tetramethyl-[1,3,2]dioxaborolane (23). A solution of 250.7 mg (0.91 mmol) 2-Benzyl-4-bromo-anisole (21), 243.1 mg (0.96 mmol, 1.1 eqv) bis(pinacolato)diboron, 269.3 mg (2.74 mmol, 3 eqv) KOAc and 37.7 mg (46 µmol, 0.05 eqv) PdCl$_2$dppf*CH$_2$Cl$_2$ in 5 ml DMSO was heated at 85° C. for 3 h. After that, water was added and the mixture was extracted with CH$_2$Cl$_2$. The comb. org. fractions were washed with water, dried over MgSO$_4$ and evaporated. Column chromatography (Hexanes/EtOAc (9+1)) yielded 160 mg (0.49 mmol, 55%) 23 as a white solid: R$_f$ (Hexanes/EtOAc (9+1)) 0.22; $^1$H NMR (400 MHz, CDCl$_3$) δ 1.26 (s, 12H), 3.74 (s, 3H), 3.90 (s, 2H), 6.80 (d, 1H, J=8.21 Hz), 7.05-7.24 (m, 5H), 7.57 (d, 1H, J=1.64 Hz), 7.62 (dd, 1H, J$_1$=8.21 Hz, J$_2$=1.64 Hz); LRMS (EI) m/z 325 (24), 324 (100), 323 (28), 309 (18), 238 (21), 225 (33), 224 (36), 223 (12), 209 (16), 191 (9), 165 (20), 147 (14), 117 (10), 91 (15), 83 (10); HRMS (EI) Calcd. for C$_{20}$H$_{25}$BO$_3$: 324.189675. Found: 324.188981.

3-(3'-benzyl-2-isobutyl-4'-methoxy-1,1'-biphenyl-4-yl)propanenitrile (24). 490 mg (1.46 mmol) Trifluoro-methanesulfonic acid 4-(2-Cyanoethyl)-2-isobutyl-phenyl ester (6), 505 mg (2.09 mmol, 1.4 eqv) crude 3-Benzyl-4-methoxy-benzene-1-boronic acid (22) and 169.4 mg (0.15 mmol, 0.1 eqv) Pd(Ph$_3$P)$_4$ were dissolved in 20 ml DME/EtOH (9+1). 1.46 ml (2.92 mmol, 2 eqv) of a 2 M aq. Na$_2$CO$_3$-solution was added to this yellow solution and the resulting mixture was heated at 80° C. for 17 h. After concentrating the mixture in vacuo the residue was taken up in water and extracted with CH$_2$Cl$_2$. The comb. org. fractions were dried over MgSO$_4$ and evaporated. Column chromatography (Hexanes/EtOAc (3+1)) yielded 290.8 mg (0.76 mmol, 52%) 24 as a clear oil: R$_f$ (Hexanes/EtOAc (3+1)) 0.34; $^1$H NMR (400 MHz, CDCl$_3$) δ 0.63 (d, 6H, J=6.70 Hz), 1.55 (m, 1H), 2.35 (d, 2H, J=7.33 Hz), 2.57 (t, 2H, J=7.45 Hz), 2.88 (t, 2H, J=7.45 Hz), 3.79 (s, 3H), 3.92 (s, 2H), 6.82 (d, 1H, J=8.34 Hz), 6.92 (d, 1H, J=2.15 Hz), 6.96-7.20 (m, 9H); LRMS (EI) m/z 383 (13), 335 (15), 293 (23), 214 (17), 187 (21), 161 (20), 160 (100), 145 (35), 144 (35), 105 (50), 91 (58), 77 (11); HRMS (EI) Calcd. for C$_{27}$H$_{29}$NO: 383.224914. Found: 383.225267.

3-(3'-benzyl-4'-hydroxy-2-isobutyl-1,1'-biphenyl-4-yl)propanenitrile (25). 2.20 ml (2.20 mmol, 3 eqv) of a 1 M solution of BBr$_3$ in CH$_2$Cl$_2$ was added to a solution of 279 mg (0.73 mmol) 3-(3'-Benzyl-2-isobutyl-4'-methoxy-1,1'-biphenyl-4-yl)propanenitrile (24) in 12 ml dry CH$_2$Cl$_2$ at 0° C. via syringe. After that, the solution was stirred for 2 h at 0° C. and then for 7 h at rt. The reaction mixture was then added to water and extracted with CH$_2$Cl$_2$. The comb. org. fractions were dried over MgSO$_4$ and evaporated. Column chromatography (Hexanes/EtOAc (2+1)) yielded 258.5 mg (0.70 mmol, 96%) 25 as a pale yellow oil: R$_f$ (Hexanes/EtOAc (2+1)) 0.53; $^1$H NMR (500 MHz, CDCl$_3$) δ 0.65 (d, 6H, J=6.62 Hz), 1.57 (m, 1H), 2.38 (d, 2H, J=7.25 Hz), 2.57 (t, 2H, J=7.41 Hz), 2.89 (t, 2H, J=7.41 Hz), 3.95 (s, 2H), 4.62 (s, br., 1H), 6.74 (d, 1H, J=8.04 Hz), 6.94-7.24 (m, 10H); LRMS (EI) m/z 369 (8), 335 (10), 293 (15), 161 (13), 160 (66), 91 (35), 86 (63), 84 (100); HRMS (EI) Calcd. for C$_{26}$H$_{27}$NO: 369.209264. Found: 369.209026.

Trifluoro-methanesulfonic acid 3-benzyl-4'-(2-cyanoethyl)-2'-isobutyl-biphenyl-4-yl ester (26). 0.10 ml (0.59 mmol, 1.8 eqv) triflic anhydride was added to a solution of 116.8 mg (0.32 mmol) 3-(3'-Benzyl-4'-hydroxy-2-Isobutyl-1,1'-biphenyl-4-yl)propanenitrile (25) in 5 ml pyridine at 0° C. The resulting mixture was stirred at 0° C. for 30 min and then at rt for 18 h. After that, water was added and the mixture was extracted with Et$_2$O. The comb. org. fractions were washed with brine, dried over MgSO$_4$ and evaporated.

Column chromatography (Hexanes/EtOAc (1+1)) yielded 136.9 mg (0.27 mmol, 85%) 26 as a pale violet solid: $R_f$ (Hexanes/EtOAc (1+1)) 0.59, $^1$H NMR (500 MHz, CDCl$_3$) δ 0.64 (d, 6H, J=6.62 Hz), 1.51 (m, 1H), 2.31 (d, 2H, J=7.25 Hz), 2.61 (t, 2H, J=7.41 Hz), 2.93 (t, 2H, J=7.41 Hz), 4.07 (s, 2H), 7.03-7.08 (m, 4H), 7.13-7.21 (m, 4H), 7.24-7.31 (m, 3H); LRMS (EI) m/z 503 (10), 502 (36), 501 (100), 369 (17), 368 (45), 326 (14), 91 (43); HRMS (EI) Calcd. for C$_{27}$H$_{26}$F$_3$NO$_3$S: 501.158551. Found: 501.158983.

3-(3',3"-dibenzyl-2-isobutyl-4"-methoxy-1,1':4',1"-terphenyl-4-yl)propanenitrile (27). 167.7 mg (0.33 mmol) 4'-(2-Cyanoethyl)-3-benzyl-2'-isobutyl-1,1'-biphenyl-4-yl-trifluoromethanesulfonate (26), 158.7 mg (0.49 mmol, 1.5 eqv) 2-(3-Benzyl-4-methoxy-phenyl)-4,4,5,5-tetramethyl-[1,3,2]dioxaborolane (23) and 58.8 mg (50.9 pmol, 0.15 eqv) Pd(Ph$_3$P)$_4$ were dissolved in 10 ml DME/EtOH (9+1). 0.33 ml (0.66 mmol, 2 eqv) of a 2 M aq. Na$_2$CO$_3$-solution was added to this yellow solution and the resulting mixture was heated at 80° C. for 8 h. After concentrating the mixture in vacuo the residue was taken up in water and extracted with CH$_2$Cl$_2$. The comb. org. fractions were dried over MgSO$_4$ and evaporated. Column chromatography (Hexanes/EtOAc (3+1)) yielded 165.6 mg (0.30 mmol, 91%) (27) as a clear oil: $R_f$ (Hexanes/EtOAc (3+1)) 0.30; $^1$H NMR (500 MHz, CDCl$_3$) δ 0.69 (d, 6H, J=6.62 Hz), 1.63 (m, 1H), 2.43 (d, 2H, J=7.41 Hz), 2.61 (t, 2H, J=7.57 Hz), 2.93 (t, 2H, J=7.57 Hz), 3.82 (s, 3H), 3.93 (s, 4H), 6.85 (d, 1H, J=8.36 Hz), 6.94 (m, 2H), 7.02-7.22 (m, 16H); LRMS (EI) m/z 549 (3), 501 (2), 446 (11), 383 (5), 335 (6), 293 (9), 256 (14), 215 (16), 214 (100), 199 (16), 160 (49), 91 (47); HRMS (EI) Calcd. for C$_{40}$H$_{39}$NO: 549.303164. Found: 549.302298.

3-(3',3"-dibenzyl-4"-hydroxy-2-isobutyl-1,1':4',1"-terphenyl-4-yl)propanenitrile (28). 0.90 ml (0.90 mmol, 3 eqv) of a 1 M solution of BBr$_3$ in CH$_2$Cl$_2$ was added to a solution of 164.3 mg (0.30 mmol) 3-(3',3"-Dibenzyl-2-isobutyl-4"-methoxy-1,1':4',1"-terphenyl-4-yl)propanenitrile (27) in 7 ml dry CH$_2$Cl$_2$ at 0° C. via syringe. After that, the solution was stirred for 2 h at 0° C. and then for 4 h at rt. The reaction mixture was then added to water and extracted with CH$_2$Cl$_2$. The comb. org. fractions were dried over MgSO$_4$ and evaporated. Column chromatography (Hexanes/EtOAc (2+1)) yielded 137.5 mg (0.26 mmol, 86%) 28 as a colorless oil: $R_f$ (Hexanes/EtOAc (2+1)) 0.35; $^1$H NMR (500 MHz, CDCl$_3$) δ 0.67 (d, 6H, J=6.62 Hz), 1.61 (m, 1H), 2.40 (d, 2H, J=7.09 Hz), 2.58 (t, 2H, J=7.41 Hz), 2.91 (t, 2H, J=7.41 Hz), 3.89 (s, 2H), 3.93 (s, 2H), 5.57 (s, 1H), 6.74 (d, 1H, J=8.04 Hz), 6.90 (m, 2H), 6.99-7.26 (m, 16H); LRMS (EI) m/z 536 (19), 535 (46), 501 (10), 446 (9), 369 (21), 91 (100), 78 (12), 76 (10); HRMS (EI) Calcd. for C$_{39}$H$_{37}$NO: 535.287514. Found: 535.287420.

3-(3',3"-dibenzyl-4"-(cyanomethoxy)-2-isobutyl-1,1':4',1"-terphenyl-4-yl)propanenitrile (29). To a suspension of 136.8 mg (0.26 mmol) 3-(3',3"-Dibenzyl-4"-hydroxy-2-isobutyl-1,1':4',1"-terphenyl-4-yl)propanenitrile (28) and 184.9 mg (1.34 mmol, 5.2 eqv) K$_2$CO$_3$ in 12 ml acetone, 0.17 ml (2.69 mmol, 10.3 eqv) chloroacetonitrile was added. The resulting mixture was stirred for 40 h at 55° C. and then added to 40 ml of a mixture of brine/water (1+1). After extraction with EtOAc the combined org. fractions were washed with brine, dried over MgSO$_4$ and evaporated. Column chromatography (Hexanes/EtOAc (2+1)) yielded 144.9 mg (0.25 mmol, 97%) 29 as a colorless oil: $R_f$ (Hexanes/EtOAc (2+1)) 0.33; $^1$H NMR (500 MHz, CDCl$_3$) δ 0.70 (d, 6H, J=6.62 Hz), 1.64 (m, 1H), 2.44 (d, 2H, J=7.41 Hz), 2.62 (t, 2H, J=7.41 Hz), 2.94 (t, 2H, J=7.41 Hz), 3.92 (s, 2H), 3.94 (s, 2H), 4.71 (s, 2H), 6.92 (m, 3H), 7.03-7.18 (m, 14H), 7.20-7.26 (m, 2H); $^{13}$C NMR (125 MHz, CDCl$_3$) δ 19.38, 21.04, 22.39, 29.53, 31.33, 35.96, 39.11, 42.02, 53.96, 111.86, 115.18, 119.18, 125.39, 125.79, 126.07, 127.27, 128.27, 128.41, 128.52, 128.64, 128.76, 129.86, 129.94, 130.31, 130.55, 131.64, 132.33, 136.32, 136.78, 137.69, 139.77, 140.19, 140.88, 140.89, 141.40, 149.00, 153.60; LRMS (EI) m/z 575 (2), 574 (5), 535 (1), 501 (1), 446 (2), 409 (15), 408 (50), 369 (13), 91 (100); HRMS (EI) Calcd. for C$_{41}$H$_{38}$N$_2$O: 574.298413. Found: 574.298309.

3-(3',3"-dibenzyl-4"-(carboxymethoxy)-2-isobutyl-1,1':4',1"-terphenyl-4-yl)propanoic acid (1b). 5 ml (41.5 mmol, 178 eqv) of a 25% aq. NaOH-solution was added to a solution of 134.0 mg (233.1 μmol) 3-(3',3"-Dibenzyl-4"-(cyanomethoxy)-2-isobutyl-1,1':4',1"-terphenyl-4-yl)propanenitrile (29) in 8 ml MeOH, 8 ml THF and 1 ml 1,4-dioxane. The resulting mixture was refluxed for 29 h and then cooled to 0° C. After adjusting the pH to 2 by adding 1 N aq. HCl-solution, which led to a white precipitate, brine was added and the mixture was extracted with THF. The comb. org. fractions were washed twice with brine, dried over MgSO$_4$ and evaporated. Column chromatography (first CH$_2$Cl$_2$/MeOH (10+1), then EtOAc/HOAc (95+5)) yielded 16.2 mg (26.4 μmol, 11%) 1b as a white solid: $R_f$ (CH$_2$Cl$_2$/MeOH (10+1)) 0.20; $^1$H NMR (500 MHz, d$_4$-MeOH+d$_4$-HOAc) δ 1.06 (d, 6H, J=6.62 Hz), 1.99 (m, 1H), 2.83 (d, 2H, J=7.25 Hz), 3.03 (t, 2H, J=7.57 Hz), 3.31 (t, 2H, J=7.57 Hz), 4.31 (s, 2H), 4.40 (s, 2H), 5.09 (s, 2H), 7.27 (m, 3H), 7.41 (d, 1H, J=2.21 Hz), 7.45-7.54 (m, 10H), 7.57-7.62 (m, 5H); $^{13}$C NMR (100 MHz, d$_4$-MeOH+d$_4$-HOAc) δ 20.86, 22.84, 30.58, 31.59, 31.61, 36.67, 39.95, 43.23, 92.03, 112.62, 126.74, 126.80, 126.87, 128.35, 129.28, 129.31, 129.32, 129.74, 130.13, 131.04, 131.14, 131.18, 131.39, 132.69, 135.83, 139.17, 140.21, 140.77, 141.26, 141.47, 142.30, 142.38, 142.94, 176.09, 176.14; LRMS (FAB) m/z 658 (16), 635 (19), 331 (16), 329 (38), 309 (15), 297 (13), 193 (10), 179 (14), 177 (100), 155 (48), 154 (14), 153 (26), 152 (23), 135 (52), 121 (18), 119 (100); HRMS (FAB) Calcd. for C$_{41}$H$_{40}$O$_5$Na: 635.277345. Found: 635.277200. Lyophilization of 1b from NH$_4$OH led to the corresponding Bisammonia salt: $^1$H NMR (500 MHz, d$_4$-MeOH) δ 0.67 (d, 6H, J=6.62 Hz), 1.59 (m, 1H), 2.41 (d, 2H, J=7.41 Hz), 2.46 (t, 2H, J=8.04 Hz), 2.90 (t, 2H, J=8.20 Hz), 3.90 (s, 2H), 4.05 (s, 2H), 4.43 (s, 2H), 6.85-6.91 (m, 3H), 6.94 (d, 1H, J=1.89 Hz), 7.02-7.24 (m, 15H).

Figure 5A:
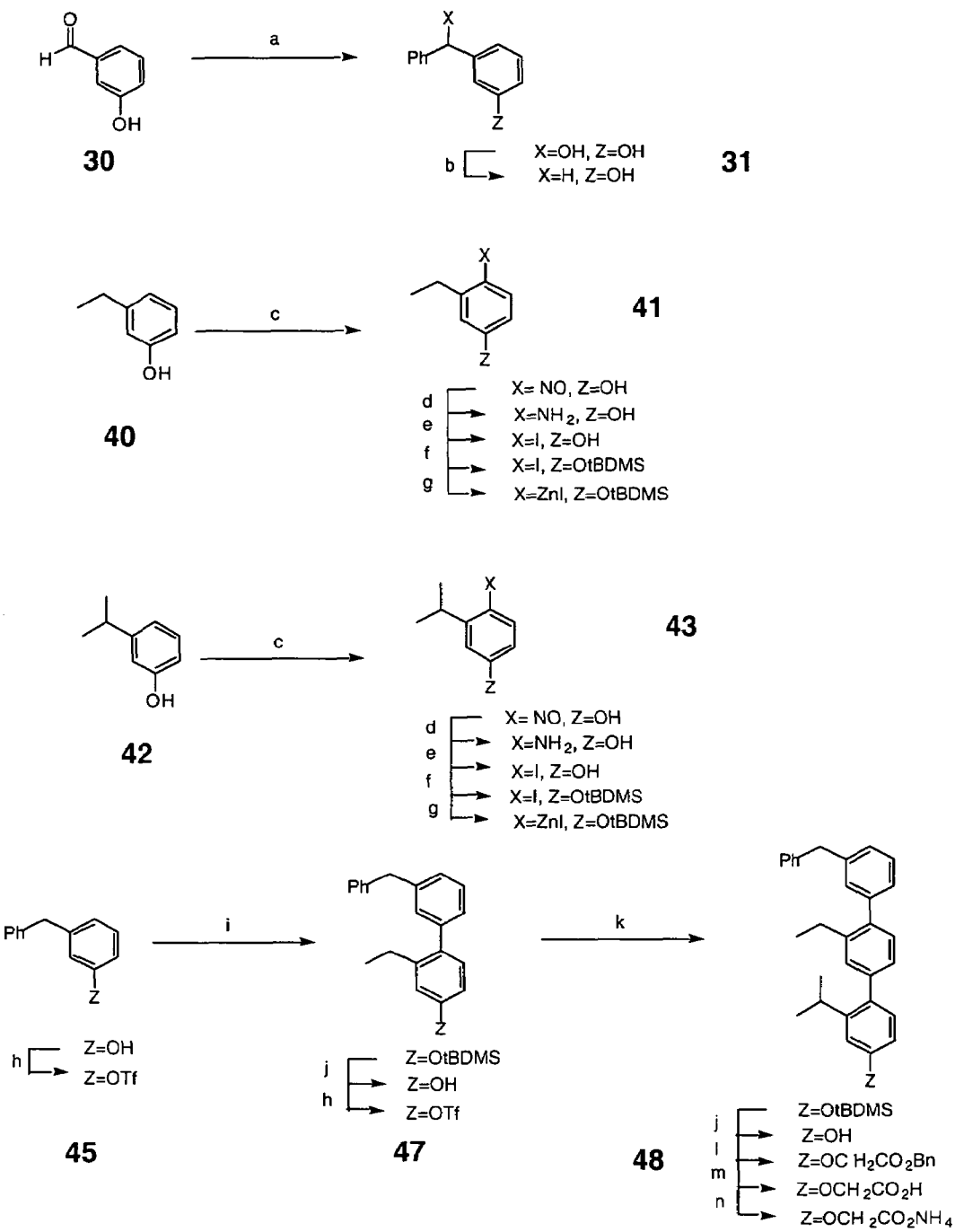
FIG. 5A represents the chemical synthesis of alternative Terphenyl derivatives according to the present invention which are CaM-binding-peptide mimetic. The following legend applies to FIG. 5A, Scheme 5A: (a) PhMgBr, THF; (b) H$_2$, Pd/C, MeOH; (c) NaNO$_2$, HCl, EtOH; (d) H$_2$, Pd/C, HCl, THF; (e) NaNO$_2$, H$_2$SO$_4$, KI, Cu; (f) tBDMSCl, imid., DMF; (g) tBuLi, ZnCl$_2$, THF; (h)Tf$_2$O, TEA, DCM; (i) A, Pd$_2$dba$_3$, dppf, THF; (j) TBAF; (k) B, Pd$_2$dba$_3$, dppf, THF; (l) BrCH$_2$CO$_2$Bn, K$_2$CO$_3$, DMF; (m) KOH, MeOH/DCM; (n) NH$_4$OH.
Figure 5B:
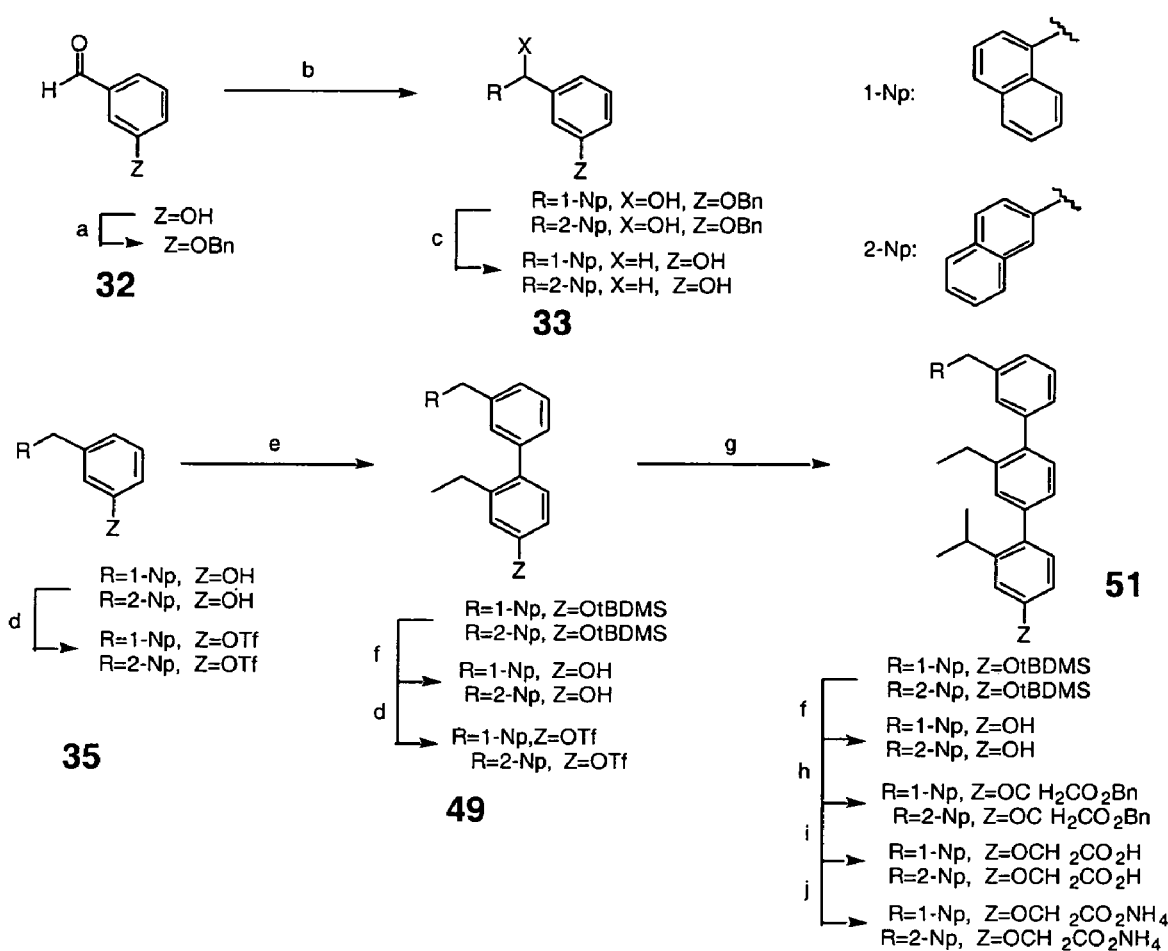
FIG. 5B represents the chemical synthesis of alternative Terphenyl derivatives according to the present invention which represent second generation CaM-binding-peptide mimetic. The following legend applies to FIG. 5B, Scheme 5B: (a) BnBr, K$_2$CO$_3$; (b) 2-Li-napthalene or 1-Li-naptha-lene, THF; (c) H$_2$, Pd/C, THF; (d)Tf$_2$O, TEA, DCM; (e) A, Pd$_2$dba$_3$, dppf, THF; (f) TBAF; (g) B, Pd$_2$dba$_3$, dppf, THF; (h) BrCH$_2$CO$_2$Bn, K$_2$CO$_3$, DMF; (i) KOH, MeOH/DCM; (j) NH$_4$OH

Synthesis Following the Presentation in FIGS. 5A, Scheme 5A and 5B, Scheme 5B

3-Benzyl-phenol (31). To a solution of m-hydroxybenzaldehyde 30 (5 g, 0.04 mol, 20 ml THF, 0° C.) was added phenylmagnesium bromide (32.8 ml, 3 M in THF, 0.010 mol). The reaction was stirred at 0° C. for one hour and then refluxed an additional hour. The solvent was removed by evaporation and the residue was dissolved in ether, extracted with 1 M HCl, washed with brine, and dried (MgSO$_4$). 69 (crude): $^1$H NMR (500 MHz, CD$_3$OD) δ 9.25 (s, 1H), 7.37-7.33 (m, 2H), 7.30-7.29 (m, 1H), 7.20-7.18 (m, 1H), 7.08-7.05 (m, 1H), 6.78-6.77 (m, 12H), 6.58-6.55 (m, 1H), 5.78 (d, J=4.0 Hz), 5.59 (d, J=4.0 Hz). The crude benzyl alcohol, 30(a), was dissolved in methanol (20 ml) and hydrogenated (60 psi, 0.500 g Pd/C) for 5 hours. The reaction mixture was filtered through Celite and concentrated to yield the substituted phenol which was purified by column chromatography. (6.9 g, 0.038 mol, 93%). $^1$H NMR (500 MHz, CDCl$_3$) δ 7.30-7.27 (m, 2H), 7.21-7.13 (m, 4H), 6.78-6.77 (m, 1H), 6.67-6.65 (m, 1H), 6.63 (s, 1H), 3.93 (s, 2H), $^{13}$C NMR (500 MHz, CDCl$_3$) δ 155.3, 142.8, 140.7, 129.5, 128.8, 128.3, 125.9, 121.3, 115.8, 113.0, 41.5.

3-Benzyloxy-benzaldehyde (32). To a solution of 3-hydroxylbenzaldehyde 31 (5.0 g, 40 mmol) and $K_2CO_3$ (27.2 g, 197 mmol) in 200 ml $CHCl_3$: 100 ml MeOH was added benzylbromide (5.9 ml, 49 mmol). The suspension was refluxed under nitrogen overnight. The solvent was removed by evaporation and the resulting oil was taken up in DCM and washed with water and brine and dried ($Na_2SO_4$). The crude product was purified by column chromatography to yield the product as a viscous oil which solidified upon sitting (8.48 g, 40 mmol, 98%). m.p. 46°. $^1$H NMR (500 MHz, $CDCl_3$) δ 9.97 (s, 1H), 7.48-7.25 (m, 9H), 5.13 (s, 2H). $^{13}$C NMR (125 MHz, $CD_3OD$) δ 191.8, 159.2, 137.8, 136.3, 130.0, 128.6, 128.1, 127.5, 123.41, 121.9, 113.3, 70.0. HRMS (EI) m/e calcd for $C_{14}H_{12}O_2$: 212.08373, found: 212.0827.

General Condensation of Napthyllithium Derivatives with 32

To a solution of bromonaphthalene (6.0 mmol) in THF (10 ml, −78°) was added t-BuLi (12.5 mmol, 1.7 M in hexanes) dropwise. This solution was added slowly to a solution of 32 (7.1 mmol) in THF (5 ml, −78°) and the mixture was allowed to warm to room temperature under nitrogen. The reaction was quenched with dilute HCl and the product was extracted into DCM, washed with acid and brine, dried ($Na_2SO_4$), and purified by column chromatography.

(3-Benzyloxy-phenyl)-naphthalen-1-yl-methanol (33). $^1$H NMR (500 MHz, $CDCl_3$) δ 8.05 (d, J=7.1 Hz, 1H), 7.86 (d, J=9.4 Hz, 1H), 7.83 (d, J=8.1 Hz, 1H), 7.63 (d, J=7.1 Hz, 1H), 7.50-7.23 (m, 8H), 7.07 (s, 1H), 7.01 (d, J=7.6 Hz, 1H), 6.89 (dd, J=8.0, 2.0 Hz, 1H), 6.52 (d, J=3.5 Hz, 1H), 5.01 (s, 2H), 2.31 (d, J=4.0 Hz, 1H). $^{13}$C NMR (125 MHz, $CDCl_3$) δ 159.0, 144.9, 138.7, 136.7, 134.0, 130.7, 129.6, 128.8, 128.6, 128.55, 128.0, 127.6, 126.2, 125.6, 125.3, 124.7, 124.0, 119.7, 114.0, 113.7. HRMS (EI) m/e calcd for $C_{24}H_{10}O_2$: 340.1463, found: 340.1459.

(3-Benzyloxy-phenyl)-naphthalen-2-yl-methanol (33). $^1$H NMR (500 MHz, $CDCl_3$) δ 7.84-7.77 (m, 3H), 7.48-7.25 (m, 9H), 7.48-7.23 (m, 10H), 7.07 (s, 1H), 7.01 (d, J=10.0 Hz, 1H), 6.49 (dd, J=10.0, 3.8), 5.97 (d, J=3.8 Hz, 1H), 5.02 (s, 2H). $^{13}$C NMR (125 MHz, $CDCl_3$) δ 159.6, 144.8, 138.6, 136.7, 133.7, 130.6, 129.3, 128.5, 128.3, 128.2, 127.7, 127.4, 125.9, 125.4, 125.2, 124.5, 123.9, 119.6, 113.6, 113.6, 73.0, 69.6.

General Hydrogenation of Naphthylmethanol Derivatives

The naphthylmethanol derivatives 33 (6 mmol) were hydrogenated (1 atm) in THF (10 ml) with HCl (1 ml) in the presence of Pd/C (100 mg) at atmospheric pressure of hydrogen. The suspension was stirred for 5 hrs, and then filtered through celite and concentrated in vacuo. The product eluted on TLC with the same $R_f$ as the starting material, however the product stained pink with vanillin while the starting material stained grey. Separation from unreacted starting material was possible only after the subsequent triflation.

3-Naphthalen-1-ylmethyl-phenol (33c). $^1$H NMR (500 MHz, $CDCl_3$) δ 7.90 (d, J=7.6 Hz, 1H), 7.76 (d, J=7.1 Hz, 1H), 7.79 (d, J=8.3 Hz, 1H), 7.40-7.31 (m, 3H), 7.21 (d, J=6.8 Hz, 1H), 7.03 (t, J=7.8 Hz, 1H), 6.72 (d, J=7.6 Hz, 1H), 6.52 (m, 2H), 5.30 (bs, 1H), 4.28 (s, 2H). $^{13}$C NMR (125 MHz, $CDCl_3$) δ 155.6, 142.7, 136.2, 133.9, 132.1, 129.6, 128.7, 127.7, 127.3, 126.0, 125.5, 125.6, 124.3, 121.3, 115.6, 113.0. HRMS (EI) m/e calcd for $C_{17}H_{14}O$: 234.1045, found: 234.1046.

3-Naphthalen-2-ylmethyl-phenol (33c). $^1$H NMR (500 MHz, $CDCl_3$) δ 7.76-7.69 (m, 3H), 7.57 (s, 1H), 7.41-7.38 (m, 2H), 7.25 (d, J=8.6 Hz, 1H), 7.09 (t, J=7.6 Hz, 1H), 6.77 (d, J=7.6 Hz, 1H), 6.59 (m, 1H), 5.16 (bs, 1H), 4.00 (S, 2H).

General Nitrosation

To a solution of 95% ethanol and HCl (90 ml, 1:1) was added m-alkylphenol 40, 42 (0.074 mol). The solution was chilled (0° C.) and sodium nitrite (0.110 mol was added slowly as a neat solid. The suspension was stirred an additional 2 hours. The reaction was quenched with water, and the crude product was isolated by filtration. The resulting solid was recrystalized from benzene.

3-Ethyl-4-nitroso-phenol (41). m.p. 134°. $^1$H NMR (500 MHz, $CDCl_3$) δ 9.15 (s, 1H), 7.79 (d, J=10 Hz, 1H), 6.44 (d, J=10.5 Hz, 1H), 6.35 (m, 1H), 2.64 (q, J=7.5 Hz, 2H), 1.20 (t, J=7.5 Hz, 2H). $^{13}$C NMR (125 MHz, $CD_3OD$) δ 189.7, 155.7, 150.8, 130.9, 127.2, 126.5, 25.2, 14.5; HRMS (EI) m/e calcd for $C_8H_9NO_2$: 151.0633, found: 151.0635.

3-Isopropyl-4-nitroso-phenol (43). m.p. 153°. $^1$H NMR (500 MHz, $CD_3OD$) δ 7.71 (d, J=10 Hz, 1H), 6.26 (d, J=10 Hz, 1H), 6.21 (s, 1H), 3.26 (m, 1H), 1.12 (d, J=6.5 Hz, 6H). $^{13}$C NMR (125 MHz, $CD_3OD$) δ 189.7, 159.7, 150.1, 130.1, 126.5, 125.0, 28.8, 23.3.

General Hydrogenation of Nitro and Nitroso Phenols

The nitro- or nitroso-phenol (28.7 mmol) was dissolved in acidic methanol or THF (50 ml methanol, 2 ml HCl) and Pd/C (0.300 g) was added. The reaction was hydrogenated (60 psi for MeOH and atmospheric pressure for THF) overnight. The catalyst was removed by Celite filtration and the solvent was removed by evaporation. The crude anilinium derivative was neutralized (extraction with EtOAc from NaOH) and purified by column chromatography but, because the product was highly susceptable to oxidation (as exhibited by dark color formation) it was generally used immediately as crude material.

4-Hydroxy-2-ethyl-phenyl-ammonium chloride (41d). $^1$H NMR (300 MHz, DMSO-d6) δ 9.97 (bs, 3H), 9.71 (bs, 1H), 7.23 (d, 1H), 6.72 (m, 1H), 6.57 (dd, 1H).

2-isopropyl-4-hydroxyl-phenyl-ammonium chloride (43d). $^1$H NMR (300 MHz, DMSO-d6) δ 8.33(bs, 1H), 6.33-6.20 (m, 3H), 4.23 (bs, 2H), 2.51 (q, J=5.7 Hz, 2H), 0.97 (t, J=5.4 Hz 3H).

General Sandmeyer Reaction

The anilinium salts (27.8 mmol) from the nitroso/nitro hydrogenations were dissolved in cold water (50 ml) with enough methanol to provide solubility. The solution was cooled (0° C.) and sulfuric acid (31.5 mmol) was added. An aqueous solution of sodium nitrite (36.1 mmol, in 5 ml water) was added over the course of one hour. The reaction was stirred for another hour at 0° C. upon which time another aliquot of cold sulfuric acid (0.5 ml) was added. A solution of potassium iodide (51.6 mmol) in water and copper bronze (2.3 mmol) were added. After a one hour reflux, the mixture was cooled and extracted with DCM and subsequently washed with sodium thiosulfate (1M), brine, and dried ($Na_2SO_4$). The resutling orange oil was difficult to purify by column chromatography and was therefore usually used crude in the silylation.

3-Ethyl-4-iodo-phenol (41e). $^1$H NMR (300 MHz, DMSO-d6) δ 7.63 (d, J=8.4, 1H), 6.75 (d, J=2.9, 1H), 6.44 (dd, J=2.9, 8.4), 4.70 (bs, 1H), 2.67 (q, J=7.8, 2H), 1.19 (t, J=7.7, 3H).

General Silylation

The concentrated iodophenols (28.7 mmol) were dissolved in DMF (20 ml) and imidazole (71.7 mmol) and t-butyldimethylsilylchloride (34.4 mmol) were added. The reaction was stirred overnight after which time the reaction was diluted with water and extracted with hexanes. The organic layers were washed with brine and dried ($Na_2SO_4$). The resulting oil was purified via silica gel column chromatography (hexanes), to yield the silyl ethers as a colorless oils.

tert-Butyl-(4-iodo-3-methyl-phenoxy)-dimethyl-silane. $^1$H NMR (500 MHz, $CDCl_3$) δ 7.59 (d, J=8.5 Hz, 1H), 6.75 (d, J=2.2 Hz, 1H), 6.41 (dd, J=2.9, 8.5 Hz, 1H), 2.36 (s, 3H), 0.97 (s, 9H), 0.18 (s, 6H)

tert-Butyl-(3-ethyl-4-iodo-phenoxy)-dimethyl-silane (41f). $^1$H NMR (500 MHz, $CDCl_3$) δ 7.61 (d, J=8.5 Hz, 1H), 6.73 (d, J=3 Hz, 1H), 6.41 (dd, J=3, 8.5 Hz, 1H), 2.65 (q, J=8, 2H), 1.18 (t, J=7.5 Hz, 3H), 0.98 (s, ~9H), 0.19 (s, 6H). $^{13}$C NMR (125 MHz, $CD_3OD$) δ 156.2, 147.6, 139.7, 120.7, 119.7, 89.9, 34.1, 25.7, 18.2, 14.5, −4.4; HRMS (EI) m/e calcd for $C_{14}H_{23}OSiI$: 362.0563, found: 362.0564.

tert-Butyl-(4-iodo-3-isopropyl-phenoxy)-dimethyl-silane (43f). $^1$H NMR (500 MHz, $CDCl_3$) δ 7.63 (d, J=8.5 Hz, 1H), 6.75 (d, J=3 Hz, 1H), 6.44 (dd, J=2.5, 8.5 Hz, 1H), 3.10 (sept, J=6.5 Hz, 1H), 1.22 (d, J=7.0 Hz, 6H), 0.91 (s, 9H), 0.21 (s, 6H); HRMS (EI) m/e calcd for $C_{15}H_{25}OSiI$: 376.0719, found: 376.0719.

General Triflation

To a solution of phenol (2.3 mmol) in dry DCM (50 ml, 0° C.) was added DIEA (2.7 mmol) and $Tf_2O$ (2.7 mmol) were added slowly. The solution was stirred for 1 hour. The reaction was diluted with DCM and washed with cold water and brine and dried ($Na_2SO_4$). The resulting crude oil was purified by column chromatography.

Trifluoro-methanesulfonic acid 3-methyl-4-nitro-phenyl ester. $^1$H NMR (300 MHz, $CDCl_3$) δ 8.10 (m, 1H), 7.33 (m, 2H), 2.66 (s, 3H). $^{13}$C NMR (125 MHz, $CDCl_3$) δ 151.6, 148.6, 137.2, 127.2, 125.6, 120.1, 118.9 (q, J=319 Hz), 20.5. LRMS (EI) m/e calcd for $C_8H_3NO_5SF_3$: 285.0, found: 285.0.

Trifluoro-methane sulfonic acid 3-benzyl-phenyl ester (45). $^1$H NMR (300 MHz, $CDCl_3$) δ 7.60-7.20 (m, 9H), 4.1 (s, 2H). $^{13}$C NMR (300 MHz, $CDCl_3$) δ 153.0, 145.1, 139.8, 132.3, 128.2, 127.5, 126.1, 123.2, 122.0, 119.6, 117.0, 42.3. $^{13}$C NMR (125 MHz, $CDCl_3$) δ 149.4, 144.4, 139.7, 130.3, 129.0, 128.9, 126.8, 121.8, 119.0, 119.2 (q, J=321 Hz) 118.3, 41.6. .6. HRMS (EI) m/e calcd for $C_{14}H_9O_3SF_3$: 315.0235, found: 315.0303.

Trifluoro-methane sulfonic acid 3-naphthalene-1-ylmethyl-phenyl ester (35d-1). $^1$H NMR (300 MHz, $CDCl_3$) δ 7.89 (d, J=6.9 Hz, 2H), 7.81 (d, J=8.2 Hz, 2H), 7.46 (m, 3H), 7.34-7.28 (m, 2H), 7.19 (d, J=7.9 Hz, 1H) 7.11 (m, 2H), 4.49 (s, 2H). $^{13}$C NMR (125 MHz, $CDCl_3$) δ 149.8, 143.8, 135.1, 134.0, 131.8, 130.2, 128.8, 128.7, 127.7, 127.5, 126.3, 125.8, 125.6, 123.9, 121.5, 121.2 (q, J=320 Hz), 119.0, 38.7. HRMS (EI) m/e calcd for $C_{18}H_{13}O_3SF_3$: 366.0537, found: 366.0539.

Trifluoro-methane sulfonic acid 3-naphthalene-2-ylmethyl-phenyl ester (35d-2). $^1$H NMR (300 MHz, $CDCl_3$) δ 7.78 (m, 3H), 7.62 (s, 1H), 7.46 (m, 2H), 7.36 (t, J=7.9, 1H), 7.28-7.24 (m, ~4H), 7.14 (m, 2H). $^{13}$C NMR (125 MHz, $CDCl_3$) δ 149.8, 144.1, 137.0, 133.6, 132.3, 130.2, 129.0, 128.5, 127.6, 127.7, 127.3, 127.2, 126.3, 125.7, 121.9 (q, J=320 Hz,), 121.8, 119.1. HRMS (EI) m/e calcd for $C_{18}H_{13}O_3SF_3$: 366.0537, found: 366.0539.

Trifluoro-methane sulfonic acid 2,3'-dimethyl-4'-nitro-biphenyl-4-yl ester. $^1$H NMR (300 MHz, $CDCl_3$) δ 8.08 (m, 2H), 7.30-7.17 (m, 5H), 2.67 (s, 3H), 2.31 (s, 3H). $^{13}$C NMR (125 MHz, $CDCl_3$) δ 149.1, 148.3, 145.1, 140.0, 138.2, 134.0, 133.4, 131.1, 127.6, 124.9, 123.1, 118.9, 118.7 (q, J=387.7), 20.7, 20.6. HRMS (EI) m/e calcd for $C_{27}H_{12}NO_5SF_3$: 376.0467, found: 376.0467.

Trifluoro-methane sulfonic acid 2-ethyl-3'-naphthalen-1-ylmethyl-biphenyl-4-yl ester (49-d1). $^1$H NMR (300 MHz, $CDCl_3$) δ 7.98 (m, 1H), 7.87 (m, 1H), 7.77 (m, 1H) 7.44 (m, 3H), 7.32 (m, 2H), 7.25 (m, 1H), 7.19 (m, 1H), 7.08 (m, 4H), 4.49 (s, 2H), 2.44 (q, J=8.0 Hz, 2H), 0.94 (t, H=8.0 Hz, 3H). HRMS (EI) m/e calcd for $C_{28}H_{18}O_3SF_3$: 470.1164, found: 470.1163.

Trifluoro-methane sulfonic acid 2-ethyl-3'-naphthalen-2-ylmethyl-biphenyl-4-yl ester (49-d2). $^1$H NMR (300 MHz, $CDCl_3$) δ 7.74 (m, 2H), 7.61 (s, 1H), 7.39 (m, 2H), 7.30 (m, 2H), 7.23-7.04 (m, 7H), 4.13 (s, 2H), 2.53 (q, J=7.3 Hz, 2H), 1.02 (t, J=7.5 Hz, 3H). $^{13}$C NMR (125 MHz, $CDCl_3$) δ 148.9, 144.5, 141.9, 141.1, 140.3, 138.3, 133.6, 132.1, 131.5, 129.7, 128.4, 128.2, 128.1, 127.5, 127.2, 126.9, 126.1, 125.5, 124.3, 121.0, 119.7 (q, J=327) 118.2, 42.1, 26.3, 15.1. HRMS (EI) m/e calcd for $C_{28}H_{18}O_3SF_3$: 470.1164, found: 470.1163.

General Aryl-Aryl Coupling

Following the general method of Baston and Hartmann, Synth., Commun., 28, 2725-2729 (1998) and Mislow, et al., J Am. Chem. Soc., 84, 1455-1478 (1962). To a solution of the iodo-silylethers (3.00 mmol) in THF (30 ml, −78° C.) t-butyllithium (1.5 M in hexanes, 5.96 mmol) was added dropwise. The solution was stirred 15 min, freshly fused zinc chloride (3.57 mmol) was added and the reaction was stirred at 0° C. for an additional 30 min. This was then added to a solution of triflate (2.83 mmol), tris(dibenzylideneacetone) dipalladium(0) (0.298 mmol) and 1,1'-bis(diphenylphosphino)-ferrocene (0.298 mmol) in THF (5 ml). The reaction was refluxed under nitrogen overnight. The solution was diluted with 0.5 M HCl and extracted with ethyl acetate. The combined organic layers were washed with brine and dried ($Na_2SO_4$). The crude product was filtered through a plug of silica gel (this was necessary to ensure that all the palladium was removed, otherwise desilylation on silica gel is sometimes observed) and then purified by means of column chromatography. It was found that the difficulty of separation of the very non-polar product from unreacted iodide or triflate could be overcome by first subjecting the material to deprotecting conditions.

tert-Butyl-(2,3'-dimethyl-4'-nitro-biphenyl-4-yloxy)-dimethyl-silane. $^1$H NMR (300 MHz, $CDCl_3$) δ 8.02 (d, J=8.9, 1H), 7.28 (m, ~2H), 7.06 (d, J=8.1 Hz, 1H), 6.77 (m, 1H), 6.73 (m, 1H), 2.66 (s, 3H), 2.23 (s, 3H), 1.01 (s, 9H), 0.24 (s, 6H). $^{13}$C NMR (125 MHz, $CDCl_3$) δ 155.7, 147.4, 147.2, 136.5, 133.70, 133.65, 132.8, 130.5, 127.9, 124.7, 122.1, 117.6, 25.7, 20.9, 20.7, 18.2, −4.4. HRMS (EI) m/e calcd for $C_{20}H_{27}NO_3Si$: 357.1760, found: 357.1758.

tert-Butyl-dimethyl-(3,2,2,-trimethyl-4-nitro-[1,1':4',1"]terphenyl-4"-yloxy)-silane. $^1$H NMR (300 MHz, $CDCl_3$) δ 8.06 (d, J=8.0 Hz, 1H), 7.35 (m, 2H), 7.21 (m, 3H), 7.11 (d, J=8.0 Hz, 1H), 6.77 (d, J=4.0 Hz, 1H), 6.73 (dd, J=8.0, 4.0 Hz, 1H), 2.67 (s, 3H), 2.31 (s, 3H), 2.28 (s, 3H), 1.01 (s, 9H), 0.24 (s, 6H). $^{13}$C NMR (125 MHz, $CDCl_3$) δ 154.9, 147.7, 147.1, 141.9, 137.7, 163.5, 134.7, 134.4, 133.6, 133.5, 131.7, 130.7, 129.1, 127.8, 127.1, 124.7, 121.8, 117.3, 25.7, 20.74, 20.65, 20.4, 18.2, −4.4. HRMS (EI) m/e calcd for $C_{27}H_{33}NO_3Si$: 447.2230, found: 447.2230.

(3'-Benzyl-2-ethyl-biphenyl-4-yloxy)-tert-butyl-dimethyl-silane (47) $^1$H NMR (300 MHz, $CDCl_3$) δ 7.33-7.29 (m, 3H), 7.24-7.22 (m, 3H), 7.17-7.14 (m, 3H), 7.05 (d, J=8.1 Hz, 1H), 6.77 (s, 1H), 6.70 (d, J=8.1 Hz, 1H) 4.03 (s, 2H), 2.51 (q, J=7.7, 2H), 1.07 (t, J=7.4, 3H), 1.02 (s, 9H), 0.25 (s, 6H). $^{13}$C NMR (125 MHz, $CDCl_3$) δ 154.9, 142.9, 142.0, 141.2, 140.8, 134.8, 130.8, 130.2, 129.0, 128.5, 128.1, 127.2, 127.0, 126.1, 119.9, 117.0, 42.0, 26.2, 25.8, 18.3, 15.6, −4.3. HRMS (EI) m/e calcd for $C_{27}H_{34}SiO$: 403.2456, found: 403.2457.

(3-Benzyl-2'-ethyl-2"-isopropyl-[1,1':4',1"]terphenyl-4"yloxy)-tert-butyl-dimethyl-silane (48). $^1$H NMR (300 MHz, $CDCl_3$) δ 7.35-7.28 (m, 3H), 7.23-7.18 (m, 8H), 7.11 (m, 1H), 7.08 (d, J=8.0 Hz, 1H), 6.84 (d, J=4.0 Hz, 1H), 6.70 (dd, J=8.0, 4.0 Hz, 1H), 4.04 (s, 2H), 3.09 (sept, J=4.0 Hz, 1H), 2.60 (q, J=8.0 Hz, 2H), 1.17 (d, J=4.0 Hz, 6H), 1.09 (t, J=8.0 Hz, 3H), 1.02 (s, 9H), 0.25 (s, 6H). HRMS (EI) m/e calcd for $C_{36}H_{44}SiO$: 520.3130 found: 520.3161.

tert-Butyl-(2'-ethyl-2"-isopropyl-3-naphthalen-1-ylmethyl-[1,1':4',1"]terphenyl-4"-yloxy)-dimethyl-silane (51-1). $^1$H NMR (300 MHz, $CDCl_3$) δ 8.02 (d, J=6.9, 1H), 7.85 (d, J=6.8 Hz, 1H), 7.76 (d, J=8.2 Hz, 1H), 7.47-7.40 (m, 4H), 7.33-7.28 (m, 2H), 7.16 (d, J=7.6 Hz, 1H), 7.10 (s, 1H), 7.02 (d, J=8.2 Hz, 1H), 6.71 (d, J=2.6 Hz, 1H), 6.65 (dd, J=8.2, 2.5 Hz, 1H), 4.48 (s, 2H), 2.39 (sept, J=7.6 Hz, 1H), 1.01 (s, 9H), 0.95 (t, J=7.8 Hz, 3H), 0.24 (s, 6H). $^{13}$C NMR (125 MHz, $CDCl_3$) δ 154.9, 142.9, 141.9, 140.3, 136.7, 134.7, 134.0, 132.2, 130.8, 129.9, 128.7, 128.1, 127.4, 127.26, 127.24, 126.9, 125.9, 125.56, 125.55, 124.4, 119.9, 117.0, 39.2, 29.7, 26.2, 18.2, 15.5, −4.3. HRMS (EI) m/e calcd for $C_{40}H_{46}OSi$: 570.3318, found: 570.3318.

tert-Butyl-(2'-ethyl-2"isopropyl-3-naphthalen-2-ylmethyl-[1,1':4',1"]terphenyl-4"-yloxy)-dimethyl-silane (51-2). $^1$H NMR (300 MHz, $CDCl_3$) δ 7.82 (m, 4H), 7.67 (s, 1H), 7.44 (m, 3H), 7.35 (m, 2H), 7.24-7.18 (m, 3H), 7.11-7.06 (m, 2H), 6.83 (d, J=2.5 Hz, 1H), 6.69 (dd, J=8.3, 2.5, 1H), 4.21 (s, 2H), 3.08 (sept, J=8.0 Hz, 1H), 2.60 (q, J=7.6 Hz, 2H), 1.16 (d, J=6.8 Hz, 6H), 1.07 (t, J=7.6 Hz 3H), 1.01 (s, 9H), 0.24 (s, 6H). $^{13}$C NMR (125 MHz, $CDCl_3$) δ 155.1, 147.8, 142.0, 141.0, 140.7, 139.7, 138.7, 134.1, 133.6, 132.1, 130.9, 130.1, 129.8, 129.5, 128.2, 128.1, 127.7, 127.63, 127.55, 127.4, 127.19, 127.15, 126.7, 126.0, 125.4, 116.99, 116.97, 42.16, 29.73, 29.69, 25.8, 24.4, 18.3, 15.7, −4.3. HRMS (EI) m/e calcd for $C_{40}H_{47}OSi$: 570.3345 found: 570.3318.

General Desilylation

The silyl ethers (2.0 mmol) were dissolved in dry THF (20 ml, 0° C.) and TBAF (4.0 mmol, 1 M in THF) was added dropwise and the reaction was stirred at 0° C. for 0.5 hr, after which time the solution was diluted with 1M HCl and extracted into DCM. The organic layers were washed with brine and dried ($Na_2SO_4$) and the resulting crude oil was purified by column chromatography.

2,3'-Dimethyl-4'-nitro-biphenyl-4-ol. $^1$H NMR (300 MHz, $CDCl_3$) δ 8.04 (d, J=8.8, 1H), 7.26 (m, 2H), 7.10 (d, J=8.3, 1H), 6,76 (m, 2H), 5.06 (bs, 3H), 2.66 (s, 3H), 2.24 (s, 3H).

3,2',2'",2'''-Tetramethyl-4-nitro-[1,1':4',1",4",1'''']quaterphenyl-4'''-ol. $^1$H NMR (300 MHz, $CDCl_3$) δ 8.04 (d, J=8.8 Hz, 1H), 7.38 (m, 2H), 7.32-7.25 (m, 4H), 7.22-7.15 (m, 3H), 6.78-6.74 (m, 2H), 2.69 (s, 3H), 2.37 (s, 3H), 2.34 (s, 3H), 2.31 (s, 3H). $^{13}$C NMR (125 MHz, $CDCl_3$) δ 154.7, 147.8, 147.1, 141.9, 140.7, 139.4, 138,1, 137.1, 134.93, 134.85, 134.4, 133.7, 133.6, 131.6, 131.5, 131.1, 129.4, 129.2, 127.8, 127.0, 126.9, 124.7, 117.0, 112.7, 20.8, 20.7, 20.6, 20.5.

3'-Benzyl-2-ethyl-biphenyl-4-ol (47j). $^1$H NMR (500 MHz, $CDCl_3$) δ 7.30-7.24 (m, 3H), 7.20-7.09 (m, 6H), 7.05 (d, J=8 Hz), 6.75 (d, J=3 Hz, 1H), 6.65 (m, 1H) 5.2 (bs, 1H), 3.99 (s, 2H), 2.49 (q, J=7.5 Hz, 2H), 1.02 (t, J=7 Hz, 3H). $^{13}$C NMR (125 MHz, $CDCl_3$) δ 154.8, 143.4, 141.7, 141.1, 140.8, 134.5, 131.2, 130.1, 129.0, 128.5, 128.1, 127.2, 127.1, 126.1, 115.2, 112.5, 42.0, 26, 2, 15.4. HRMS (EI) m/e calcd for $C_{21}H_{18}O$: 286.1514 found: 286.1511.

3-Benzyl-2'-ethyl-2"-isopropyl-[1,1':4',1"]terphenyl-4"-ol (48j). $^1$H NMR (500 MHz, $CDCl_3$) δ 7.35-7.28 (m, 3H), 7.25-7.18 (m, 8H), 7.11 (d, J=8.1 Hz 1H), 6.85 (d, J=2.6, 1H), 6.70 (dd, J=8.1, 2.6 Hz, 1H), 4.74 (bs, 1H), 4.04 (s, 2H), 3.11 (sept, J=6.6, 1H), 2.60 (q, J=7.4, 2H), 1.18 (d, J=7.0, 6H), 1.08 (t, J=7.7, 3H). $^{13}$C NMR (125 MHz, $CDCl_3$) δ 153.0, 148.4, 142.0, 141.13, 141.11, 140.9, 140.8, 139.8, 134.0, 131,3, 130.0, 129.8, 129.6, 129.0, 128.5, 128.2, 127.4, 127.1, 126.7, 126.1, 112.4, 112.3, 42.0, 29.7, 26.2, 24.4, 15.7. HRMS (EI) m/e calcd for $C_{30}H_{29}O$: 406.2297 found: 406.2295.

2-Ethyl-3'-naphthalen-1-ylmethyl-biphenyl-4-ol (51f-1). $^1$H NMR (500 MHz, $CDCl_3$) δ 8.00 (m, 1H), 7.85 (m, 1H), 7.75 (d, J=8.1 Hz, 1H), 7.42 (m, 3H), 7.28 (m, 2H), 7.18 (m, 1H), 7.08 (m, 2H), 7.02 (d, J=8.1 Hz, 1H), 6.69-6.63 (m, 2H).

2-Ethyl-3'-naphthalen-2-ylmethyl-biphenyl-4-ol (51f-2). $^1$H NMR (500 MHz, $CDCl_3$) δ 7.80 (m, 3H), 7.66 (s, 1H), 7.43 (m, 2H), 7.35 (m, 2H), 7.24-7.18 (m, 5H), 7.08 (m, 2H), 6.84 (s, 1H), 6.67 (d, J=7.0, 1H), 5.31 (bs, 1H), 4.18 (s, 2H), 3.10 (sept, J=6.9 Hz, 1H), 2.60 (q, J=7.8 Hz, 2H), 1.15 (d, J=7.0 Hz, 6H), 1.06 (t, J=7.6 Hz, 3H).

General Etherification with Benzyl Bromoacetate.

The phenol (1.6 mmol) was dissolved in DMF (5 ml) with $K_2CO_3$ (4.9 mmol) and heated to 70° C., and benzyl bromo acetate (4.2 mmol) was added. The reaction was heated for 1 hour after which time the solution was diluted with water and extracted with DCM. The combined organic layers were washed with brine and dried ($Na_2SO_4$), and the concentrated product was purified by silica gel chromatography.

(3-Benzyl-2'-ethyl-2"-isopropyl-[1,1':4',1"]terphenyl-4"-yloxy)-acetic acid benzyl ester (48l). $^1$H NMR (500 MHz, $CDCl_3$) δ 7.38-7.16 (m, ~17H), 7.98 (m, 1H), 6.73 (m, 1H), 4.68 (s, 2H), 4.03 (s, 2H), 3.84 (s, ~2H), 3.12 (sept, J=7.0 Hz, 1H), 2.58 (q, J=7.0 Hz, 2H), 1.17 (d, J=7.5 Hz, 6H), 1.08 (t, J=7.0 Hz, 3H). $^{13}$C NMR (125 MHz, $CDCl_3$) δ 172.5, 169.0, 161.3, 157.3, 148.3, 141.9, 141.1, 140.9, 140.6, 139.9, 131,1, 130.0, 129.8, 129.6, 129.0, 128.7, 128.6, 128.5, 128.2, 127.4, 127.1, 126.3, 126.1, 112.5, 67.3, 65,5, 42.0, 29.7, 26.2, 24.3, 15.7.

(2'-Ethyl-2"-isopropyl-3-naphthalen-2-ylmethyl-[1,1':4',1"]terphenyl-4'-yloxy)-acetic acid benzyl ester (51h-2). $^1$H NMR (500 MHz, $CDCl_3$) δ 7.79 (m, 3H), 7.67 (s, 1H), 7.44 (m, 2H), 7.35 (m, 7H), 7.29-7.03 (m, ~9H), 6.96 (d, J=4.0 Hz, 1H), 6.73 (dd J=8.0, 4.0 Hz, 1H), 5.27 (s, 2H), 4.71 (s, 2H), 4.21 (s, 2H), 3.09 (sept, J=7.9 Hz, 1H), 2.60 (q, J=8.0 Hz, 2H), 1.17 (d, J=7.8 Hz, 6H), 1.07 (t, J=8.0 Hz, 3H). $^{13}$C NMR (125 MHz, $CDCl_3$) δ 169.0, 157.3, 148.3, 141.8, 141.1, 140.6, 140.4, 140.4, 139.8, 136.6, 135.2, 134.9, 134.0, 132.2, 131.0, 129.6, 129.7, 129.5, 128.69, 128.67, 128.60 128.56, 128.50, 128.2, 127.5, 127.2, 127.2, 127.1, 126.6, 125.9, 125.6, 124.4, 112.5, 110.9, 67.0, 65.5, 39.2, 29.7, 26.1, 24.3, 15.6. HRMS (EI) m/e calcd for $C_{43}H_{40}O_3$: 604.2977 found: 604.2978.

Hydrolysis of Benzyl Esters

The ester (1.6 mmol) was dissolved in 5 ml 5% KOH in MeOH with a small amount of DCM to aid in solubilization. The solution was stirred at room temperature for 30 min, after which time it was acidified and extracted into DCM. The combined organic layers were washed with acidic brine and dried ($Na_2SO_4$). The product was passed through a plug of silica gel and then purified by reverse phase HPLC. The resulting lyophized product was taken up in distilled water and NH$_4$OH and the solvent was lyophilzed to yield the ammonium salt.

(3-Benzyl-2'-ethyl-2"-isopropyl-[1,1':4',1"]terphenyl-4"-yloxy)-acetic acid (48m). $^1$H NMR (500 MHz, CD$_3$OD) δ 8.00 (bs, 1H), 7.33 (m, 1H), 7.28-7.05 (m, 12H), 6.95 (d, J=4.0 Hz, 1H), 6.78 (dd, J=4.0, 8.0 Hz, 1H), 4.68 (s, 2H), 4.01 (s, 2H), 3.08 (sept, J=7.6 Hz, 1H), 2.55 (q, J=8.1 Hz, 2H), 1.16 (d, J=7.8 Hz, 6H), 1.01 (t, J=7.8 Hz, 3H). HRMS (EI) m/e calcd for C$_{30}$H$_{38}$O$_3$: 446.1494 found: 446.2821.

Ammonium (3-benzyl-2'-ethyl-2"-isopropyl-[1,1':4',1"]terphenyl-4"-yloxy)-acetate (48.NH$_4$). $^1$H NMR (500 MHz, CD$_3$OD) δ 7.36 (m, 1H), 7.29-7.15 (m, 10H), 7.07 (m, 2H), 6.91 (s, 1H), 6.72 (d, J=7.9 Hz, 1H), 5.76 (bs, ~2H), 4.51 (s, 2H), 4.00 (s, 2H), 2.91 (sept, 7.9 Hz, 1H), 2.50 (q, J=8.2 Hz, 2H), 1.20 (d, J=7.5 Hz, 6H), 0.92 (t, 7.9 Hz, 3H). $^{13}$C NMR (125 MHz, CD$_3$OD) δ 158.2, 147.4, 141.68, 141.65, 141.5, 140.9, 140.8, 139.6, 133.2, 130.9, 129.9, 129.8, 129.1, 128.8, 128.7, 127.6, 127.0, 126.4, 112.3, 111.5, 55.3, 48.9, 29.6, 25.9, 24.5, 14.0. HRMS (EI) m/e calcd for C$_{32}$H$_{35}$O$_2$N: 487.2273 found: 487.2268.

(2'-Ethyl-2"-isopropyl-3-naphthalen-1-ylmethyl-[1,1':4',1"]terphenyl-4"-yloxy)-acetic acid (51i-1). $^1$H NMR (500 MHz, CD$_3$OD) δ 8.03 (m, 1H), 7.86 (m, 1H), 7.77 (s, J=8.2 Hz, 1H), 7.54 (m, 3H), 7.33 (m, 2H), 7.23-7.13 (m, 6H), 7.07 (m, 1H), 6.99 (m, 1H), 6.73 (m, 1H), 4.72 (s, 2H), 4.51 (s, 2H), 3.12 (sept, J=6.9 Hz, 1H), 2.49 (q, J=7.6 Hz, 2H), 1.17 (d, J=6.9, 6H), 0.97 (t, J=7.3 Hz, 3H). $^{13}$C NMR (125 MHz, CD$_3$OD) δ 173.9, 156.9, 148.5, 141.8, 141.2, 140.44, 139.9, 136.6, 135.3, 134.0, 132.2, 129.79, 129.72, 129.5, 128.7, 128.2, 127.4, 127.2, 127.2, 127.1, 126.6, 125.9, 125.6, 124.4, 112.6, 110.8, 65.0, 39.2, 29.7, 26.1, 24.3, 15.5. HRMS (EI) m/e calcd for C$_{36}$H$_{34}$O$_3$: 514.2508 found: 514.2509.

(2'-Ethyl-2"-isopropyl-3-naphthalen-2-ylmethyl-[1,1':4',1"]terphenyl-4"-yloxy)-acetic acid (51i-2). $^1$H NMR (500 MHz, CD$_3$OD) δ 7.77 (m, 3H), 7.66 (s, 1H), 7.43 (m, 2H), 7.35 (m, 2H), 7.24-7.16 (m, 6H), 7.09 (d, J=7.6, 1H), 6.99 (s, 1H), 6.76 (d, J=8.2 Hz, 4.71 (s, 2H), 4.19 (s, 2H), 3.11 (sept, J=6.6 Hz, 1H), 2.60 (q, J=7.35 Hz, 2H), 1.17 (d, J=6.9 Hz, 6H), 1.06 (t, J=7.6 Hz, 3H). $^{13}$C NMR (125 MHz, CD$_3$OD) δ 157.0, 148.5, 141.9, 141.1, 140.8, 140.5, 139.9, 138.6, 135.3, 133.6, 132.1, 131.2, 130.1, 129.7, 129.6, 128.2, 128.1, 127.8, 127.7, 127.6, 127.5, 127.2, 126.6, 126.0, 125.4, 112.6, 110.8, 65.1, 42.2, 29.6, 26.2, 24.3, 15.6. HRMS (EI) m/e calcd for C$_{36}$H$_{34}$O$_3$: 514.2508 found: 514.2509.

Figure 6:
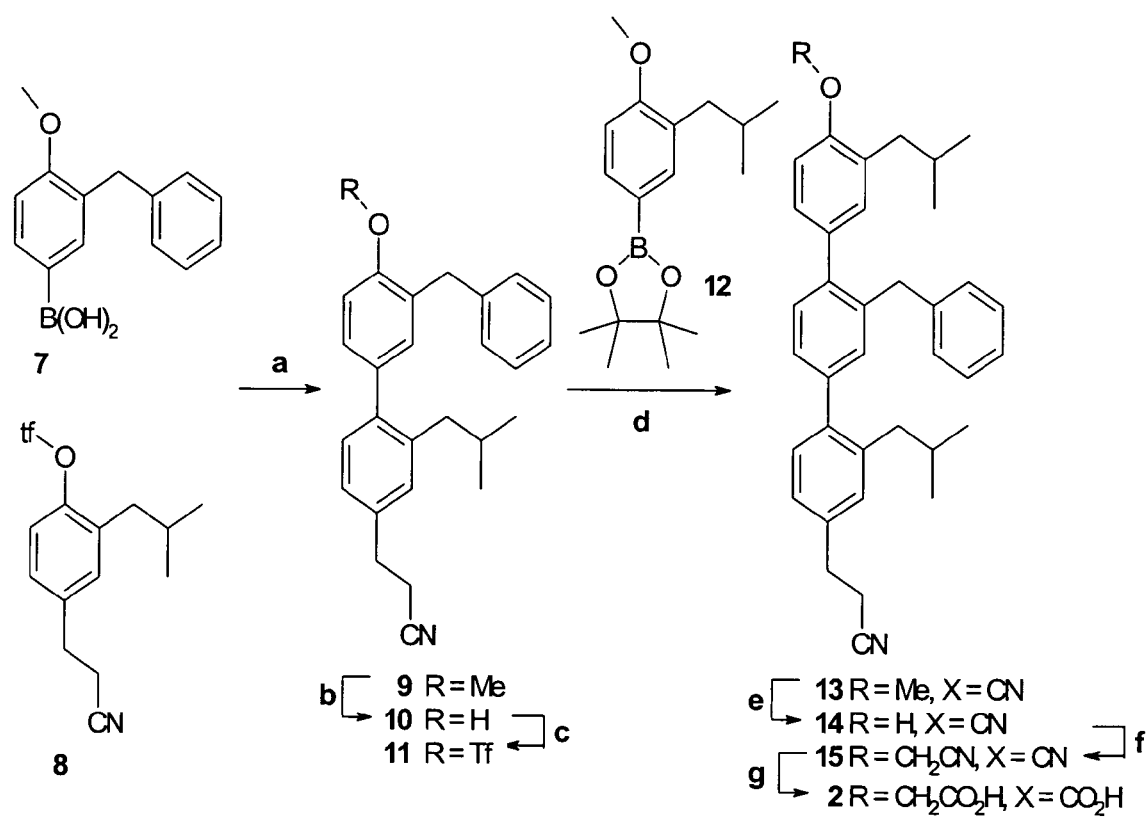
FIG. 6 represents the chemical synthesis of the terphenyl derivatives as indicated. The following legend applies to FIG. 6: a: Pd(Ph$_3$P)$_4$, DME/EtOH (9+1), 2 M aq. Na$_2$CO$_3$, 80° C., 17 h, 52%. b: BBr$_3$, CH$_2$Cl$_2$, 0° C.-r.t., 9 h, 96%. c: Tf$_2$O, Py, 0° C.-r.t., 18 h, 85%. d: Pd(Ph$_3$P)$_4$, DME/EtOH (9+1), 2 M aq. Na$_2$CO$_3$, 80° C., 19 h, 88%. e: BBr$_3$, CH$_2$Cl$_2$, 0° C.-r.t., 6.5 h, 100%. f: K$_2$CO$_3$, acetone, ClCH$_2$CN, 55° C., 40 h, 91%. g: 25% aq. NaOH, MeOH/THF (1:1), rfl., 24 h, 77%.

Synthesis Following the Presentation in FIG. 6, Scheme 6

Synthesis of the benzyl-bisisobutyl-terphenyl derivative 58.

3-(3'-Benzyl-2,3"-diisobutyl-4"-methoxy-1,1':4',1"-terphenyl-4-yl)propanenitrile (55). 134.6 mg (0.27 mmol) Trifluoro-methanesulfonic acid 3-benzyl-4'-(2-Cyano-ethyl)-2'-isobutyl-biphenyl-4-yl ester (54), 96.9 mg (0.33 mmol, 1.24 eq.) 2-(3-isobutyl-4-methoxyphenyl)-4,4,5,5-tetramethyl-[1,3,2]dioxaborolane (11) and 46.7 mg (40 µmol, 0.15 eq.) Pd(Ph$_3$P)$_4$ were dissolved in 7 ml DME/EtOH (9+1). To this yellow solution 0.27 ml (0.54 mmol, 2.00 eq.) of a 2 M aq. Na$_2$CO$_3$-solution was added and the resulting mixture was heated at 80° C. for 19 h. After concentrating the mixture in vacuo the residue was taken up in water and extracted with CH$_2$Cl$_2$. The comb. org. fractions were dried over MgSO$_4$ and evaporated. Column chromatography (hexanes/EtOAc (6+1)) yielded 122.9 mg (0.24 mmol, 88.26%) 3-(3'-Benzyl-2,3"-diisobutyl-4"-methoxy-1,1':4',1"-terphenyl-4-yl)propanenitrile (55) as a clear oil. R$_f$ (hexanes/EtOAc (6+1))=0.20. $^1$H-NMR (500 MHz, CDCl$_3$): δ=0.69 (d, 6H, J=6.62 Hz, 2*CH$_3$), 0.84 (d, 6H, J=6.62 Hz, 2*CH$_3$), 1.63 (m, 1H, CH), 1.83 (m, 1H, CH), 2.42 (d, 2H, J=7.25 Hz, CH$_2$), 2.44 (d, 2H, J=7.25 Hz, CH$_2$), 2.61 (t, 2H, J=7.41 Hz, CH$_2$CH$_2$CN), 2.93 (t, 2H, J=7.41 Hz, CH$_2$CH$_2$CN), 3.81 (s, 3H, OCH$_3$), 3.98 (s, 2H, CH$_2$Ph), 6.81 (d, 1H, J=8.51 Hz), 6.96 (m, 2H), 7.00-7.18 (m, 10H), 7.24-7.26 (d, 1H, J=7.57 Hz). MS (EI): m/z=517 (10), 516 (45), 515 (100), 472 (10), 381 (8), 91 (20). HR-MS (EI): Calcd. for C$_{37}$H$_{41}$NO: 515.318814. Found: 515.319235.

3-(3'-Benzyl-4"-hydroxy-2,3"-diisobutyl-1,1':4',1"-terphenyl-4-yl)propanenitrile (56).

0.71 ml (0.71 mmol, 2.98 eq.) of a 1 M solution of BBr$_3$ in CH$_2$Cl$_2$ was added to a solution of 122.8 mg (0.238 mmol) 3-(3'-Benzyl-2,3"-diisobutyl-4"-methoxy-1,1':4',1"-terphenyl-4-yl)propanenitrile (55) in 5 ml dry CH$_2$Cl$_2$ at 0° C. via syringe. After that the solution was stirred for 90 min at 0° C. and then for 5 h at r.t. The reaction mixture was then added to water and extracted with CH$_2$Cl$_2$. The comb. org. fractions were dried over MgSO$_4$ and evaporated. Column chromatography (hexanes/EtOAc (2+1)) yielded 119.3 mg (0.24 mmol, 99.91%) 3-(3'-Benzyl-4"-hydroxy-2,3"-diisobutyl-1,1':4',1"-terphenyl-4-yl)propanenitrile (56) as a colorless oil. R$_f$ (hexanes/EtOAc (2+1))=0.40. $^1$H-NMR (500 MHz, CDCl$_3$): δ=0.69 (d, 6H, J=6.62 Hz, 2*CH$_3$), 0.86 (d, 6H, J=6.62 Hz, 2*CH$_3$), 1.63 (m, 1H, CH), 1.87 (m, 1H, CH), 2.43 (d, 2H, J=7.25 Hz, CH$_2$), 2.47 (d, 2H, J=7.09 Hz, CH$_2$), 2.61 (t, 2H, J=7.41 Hz, CH$_2$CH$_2$CN), 2.93 (t, 2H, J=7.41 Hz, CH$_2$CH$_2$CN), 3.95 (s, 2H, CH$_2$Ph), 5.51 (s, 1H, OH), 6.88 (d, 1H, J=2.05 Hz), 6.95 (m, 2H), 6.97-7.26 (m, 11H). MS (EI): m/z=502 (40), 501 (100), 458 (4), 367 (10), 327 (7), 307 (8), 263 (8), 91 (43). HR-MS (EI): Calcd. for C$_{36}$H$_{39}$NO: 501.303164. Found: 501.303902.

3-(3'-Benzyl-4"-(cyanomethoxy)-2,3"-diisobutyl-1,1'4'1"-terpehnyl-4-yl)propanenitrile (57)

To a suspension of 116.5 mg (232 µmol) 3-(3'-Benzyl-4"-hydroxy-2,3"-diisobutyl-1,1':4',1"-terphenyl-4-yl)propanenitrile (56) and 46.8 mg (0.34 mmol, 1.46 eq.) K$_2$CO$_3$ in 12 ml acetone 0.15 ml (2.37 mmol, 10.22 eq.) chloroacetonitrile was added. The resulting mixture was stirred for 40 h at 55° C. and then added to 40 ml of a mixture of brine/water (1+1). After extraction with EtOAc the combined org. fractions were washed with brine, dried over MgSO$_4$ and evaporated. Column chromatography (hexanes/EtOAc (2+1)) yielded 114.7 mg (212 µmol, 91.43%) 3-(3'-Benzyl-4"-(cyanomethoxy)-2,3"-diisobutyl-1,1': 4',1"-terphenyl-4-yl)propanenitrile (57) as a colorless oil. R$_f$ (hexanes/EtOAc (2+1))=0.40. $^1$H-NMR (500 MHz, CDCl$_3$): δ=0.71 (d, 6H, J=6.62 Hz, 2*CH$_3$), 0.85 (d, 6H, J=6.62 Hz, 2*CH$_3$), 1.65 (m, 1H, CH), 1.81 (m, 1H, CH), 2.45 (d, 2H, J=7.41 Hz, CH$_2$), 2.46 (d, 2H, J=7.41 Hz, CH$_2$), 2.62 (t, 2H, J=7.57 Hz, CH$_2$CH$_2$CN), 2.94 (t, 2H, J=7.57 Hz, CH$_2$CH$_2$CN), 3.96 (s, 2H, CH$_2$Ph), 4.79 (s, 2H, OCH$_2$CN), 6.88 (d, 1H, J=8.51 Hz), 6.94 (m, 2H), 7.02-7.19 (m, 11H). $^{13}$C-NMR (125 MHz, CDCl$_3$): δ=19.79, 22.81, 22.90, 29.36, 29.95, 31.74, 39.19, 39.51, 42.45, 54.17, 111.70, 115.72, 119.60, 125.80, 126.19, 127.65, 128.29, 128.65, 129.05, 129.06, 130.27, 130.37, 130.97, 131.17, 132.00, 133.07, 136.25, 137.17, 138.11, 138.12, 140.20, 140.39, 141.20, 141.36, 141.87, 154.20. MS (EI): m/z=540 (7), 447 (37), 446 (100), 77 (13). HR-MS (EI): Calcd. for C$_{38}$H$_{40}$N$_2$O: 540.314063. Found: 540.314306.

3-(3'-Benzyl-4"-(carboxymethoxy)-2,3"-diisobutyl-1,1'4'1"-terphenyl-4-yl)propanoic acid (58)

To a solution of 86.4 mg (159.78 µmol) 3-(3'-Benzyl-4"-(cyanomethoxy)-2,3"-diisobutyl-1,1':4',1"-terphenyl-4-yl)

propanenitrile (57) in 6 ml methanol and 6 ml THF 3 ml (24.90 mmol, 155 eq.) 25% aq. NaOH-solution was added. The resulting mixture was refluxed for 24 h and then cooled to 0° C. After acidifying to pH 2 by adding 1 N aq. HCl-solution brine was added and the mixture was extracted with THF. The comb. org. fractions were washed twice with brine, dried over MgSO$_4$ and evaporated. Column chromatography (first CH$_2$Cl$_2$/MeOH (4+1), then EtOAc/HOAc (95+5)) yielded 70.9 mg (122.5 µmol, 76.67%) 3-(3'-Benzyl-4"-(carboxymethoxy)-2,3"-diisobutyl-1,1':4',1"-terphenyl-4-yl)propanoic acid (58) as a white solid. R$_f$ (EtOAc/HOAc (95+5))=0.76. $^1$H-NMR (500 MHz, d$_4$-MeOH+1% d$_4$-HOAc): δ=0.83 (d, 6H, J=6.62 Hz, 2*CH$_3$), 1.02 (d, 6H, J=6.62 Hz, 2*CH$_3$), 1.76 (m, 1H, CH), 2.07 (m, 1H, CH), 2.60 (d, 2H, J=7.25 Hz, CH$_2$), 2.68 (d, 2H, J=7.25 Hz, CH$_2$), 2.77 (t, 2H, J=7.57 Hz, CH$_2$CH$_2$CO$_2$H), 3.06 (t, 2H, J=7.57 Hz, CH$_2$CH$_2$CO$_2$H), 4.14 (s, 2H, CH$_2$Ph), 4.79 (s, 2H, OCH$_2$CO$_2$H), 6.99 (d, 1H, J=8.36 Hz), 7.10 (m, 2H), 7.21-7.33 (m, 10H), 7.39 (d, 1H, J=7.72 Hz). $^{13}$C-NMR (125 MHz, d$_4$-MeOH+1% d$_4$-HOAc): δ=20.89, 22.85, 23.04, 29.82, 30.66, 30.92, 31.78, 35.38, 36, 89, 40.01, 40.52, 44.83, 112.38, 126.21, 126.74, 126.81, 128.36, 128.88, 129.30, 129.76, 131.08, 131.17, 131.31, 132.74, 133.18, 135.33, 139.16, 140.26, 140.92, 141.37, 141.81, 142.40, 143.14, 156.93, 160.58, 171.38, 178.30. MS (ESI): 580 (10), 579 (42), 578 (100), 326 (10), 312 (19), 289 (26), 260 (15), 186 (12), 173 (10). HR-MS (FAB): Calcd. for C$_{38}$H$_{42}$O$_5$: 578.303225. Found: 578.303100.

Bis-ammonia-salt of 58: $^1$H-NMR (500 MHz, d$_4$-MeOH): δ=0.69 (d, 6H, J=6.62 Hz, 2*CH$_3$), 0.87 (d, 6H, J=6.62 Hz, 2*CH$_3$), 1.61 (m, 1H, CH), 1.93 (m, 1H, CH), 2.45 (d, 2H, J=7.25 Hz, CH$_2$), 2.55 (d, 2H, J=7.09 Hz, CH$_2$), 2.60 (t, 2H, J=7.41 Hz, CH$_2$CH$_2$CO$_2$NH$_4$), 2.92 (t, 2H, J=7.72 Hz, CH$_2$CH$_2$CO$_2$NH$_4$), 3.99 (s, 2H, CH$_2$Ph), 4.48 (s, 2H, OCH$_2$CO$_2$NH$_4$), 6.84 (d, 1H, J=8.36 Hz), 6.94-6.99 (m, 3H), 7.06 (dd, 1H, J$_1$=8.20 Hz, J$_2$=2.36 Hz), 7.07-7.19 (m, 8H), 7.24 (d, 1H, J=7.72 Hz). MS (FAB): 579 (11), 578 (21), 454 (9), 279 (10), 220 (10), 219 (54), 195 (34), 155 (38), 135 (26), 119 (100). HR-MS (FAB): Calcd. for C$_{38}$H$_{42}$O$_5$: 578.303225. Found: 578.303000.

Figure 7:
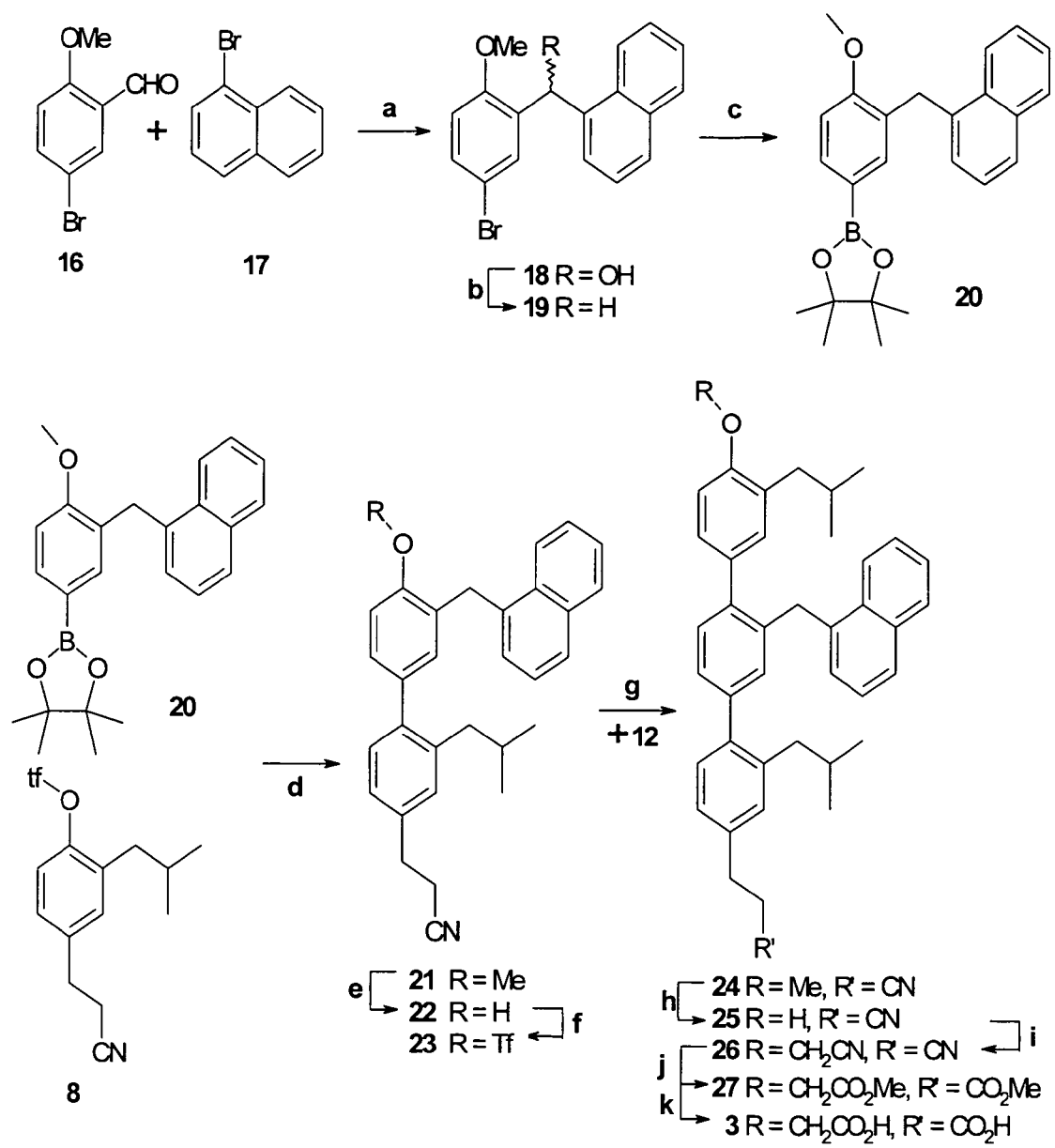
FIG. 7 represents the chemical synthesis of the terphenyl derivatives as indicated. The following legend applies to FIG. 7: a: n-BuLi, THF, −78° C. (1.5 h), −30° C. (2 h), r.t. (3.5 h), 88%. b: NaBH$_4$, TFA, CH$_2$Cl$_2$, r.t., 24 h, 96%. c: bis(pinacolato)diboron, KOAc, PdCl$_2$dppf*CH$_2$Cl$_2$, DMSO, 85° C., 5 h, 67%. d: Pd(Ph$_3$P)$_4$, DME/EtOH (9+1), 2 M aq. Na$_2$CO$_3$, 80° C., 15 h, 88%. e: BBr$_3$, CH$_2$Cl$_2$, 0° C. (2 h), r.t. (14 h), 94%. f: Tf$_2$O, Py, 0° C. (1 h), r.t., 19 h, 90%. g: 12, Pd(Ph$_3$P)$_4$, DME/EtOH (9+1), 2 M aq. Na$_2$CO$_3$, 80° C., 9 h, 94%. h: BBr$_3$, CH$_2$Cl$_2$, 0° C. (1 h), r.t. (12 h), 99%. i: K$_2$CO$_3$, acetone, ClCH$_2$CN, 55° C., 24 h, 98%. J: HCl(g), MeOH, rfl., 1.5 h, 88%. k: 25% aq. NaOH, 40% aq. Bu$_4$NOH, 1,4-dioxane, rfl., 24 h, 100%.

Synthesis Following the Presentation in FIG. 7, Scheme 7

Synthesis of the isobutyl-1-naphthalene-isobutyl-terphenyl-derivative 3.

(5-Bromo-2-methoxy-phenyl)-napthalen-1-yl-methanol (62).

To a solution of 1.70 ml (12.22 mmol) 1-Bromonaphthalene (61) in 40 ml dry THF 7.64 ml (12.22 mmol, 1.00 eq.) of a 1.6 M solution of n-Butyllithium in hexanes were added at −78° C. via syringe. After stirring this mixture for 1 h at −78° C. a solution of 2.63 g (12.23 mmol, 1.00 eq.) 4-bromo-anisaldehyde (60) in 30 ml dry THF was added dropwise via a dropping funnel. The resulting mixture was stirred for another 60 min at −78° C., then for 2 h at −30° C. and finally 15 h at r. t. After quenching the reaction with 1 M aq. HCl-solution and adding ether the org. phase was washed subsequently with water and brine before it was dried over MgSO$_4$ and evaporated. Column chromatography (CH$_2$Cl$_2$) yielded 3.70 g (10.77 mmol, 88.15%) (5-Bromo-2-methoxy-phenyl)-napthalen-1-yl-methanol (62) as pale greenish foam. R$_f$ (CH$_2$Cl$_2$)=0.37. $^1$H-NMR (500 MHz, CDCl$_3$): δ=3.84 (s, 3H, OMe), 6.80 (d, J=8.51 Hz, 1H), 6.81 (s, 1H, HO—CH), 7.18 (d, 1H, J=2.68 Hz), 7.34 (dd, 1H, J$_1$=8.82 Hz, J$_2$=2.52 Hz), 7.42-7.48 (m, 3H), 7.55 (d, 1H, J=7.09 Hz), 7.79 (d, 1H, J=8.20 Hz), 7.83-7.87 (m, 1H), 7.96-8.00 (m, 1H). MS (EI): m/z=345 (14), 344 (76), 343 (17), 342 (77), 326 (14), 325 (12), 324 (14), 311 (10), 309 (10), 245 (25), 217 (12), 215 (88), 213 (84), 202 (19), 201 (12), 157 (18), 155 (37), 141 (21), 129 (66), 128 (100), 127 (42), 108 (12), 101 (24), 77 (14), 63 (11). HR-MS (EI): Calcd. for C$_{18}$H$_{15}$BrO$_2$: 342.025541. Found: 342.025182.

1-(5-Bromo-2-methoxy-benzyl)-naphthalene (63).

3.06 g (80.89 mmol, 10.48 eq.) NaBH$_4$ (granules) were added slowly to 50 ml Trifluoroacetic acid at 0° C. To this mixture a solution of 2.65 g (7.72 mmol) (5-Bromo-2-methoxy-phenyl)-napthalen-1-yl-methanol (62) in 30 ml dry CH$_2$Cl$_2$ was added which led to an brownish mixture. After stirring this mixture for 19 h at r.t. it was diluted with water and cooled again to 0° C. At this temperature NaOH-pellets were added carefully to adjust the pH to 10 before the solution was extracted with ether. The comb. org. fractions were washed with brine, dried over Na$_2$SO$_4$ and evaporated. Column chromatography (CH$_2$Cl$_2$) yielded 2.42 g (7.39 mmol, 95.72%) 1-(5-Bromo-2-methoxy-benzyl)-naphthalene (63) as a pale yellow oil. R$_f$ (CH$_2$Cl$_2$)=0.73. $^1$H-NMR (400 MHz, CDCl$_3$): δ=3.84 (s, 3H, OMe), 4.35 (s, 2H), 6.76 (d, 1H, J=8.72 Hz), 6.91 (d, 1H, J=2.53 Hz), 7.20 (dm, 1H, J$_1$=6.82 Hz), 7.26 (dd, 1H, J$_1$=8.84 Hz, J$_2$=2.53 Hz), 7.38 (m, 1H), 7.41-7.49 (m, 2H), 7.74 (d, 1H, J=8.34 Hz), 7.84 (m, 1H), 7.91 (m, 1H). MS (EI): m/z=329 (18), 328 (97), 327 (20), 326 (100), 248 (16), 247 (35), 232 (22), 231 (25), 216 (20), 215 (41), 203 (17), 202 (25), 142 (21), 141 (61), 115 (10), 101 (14). HR-MS (EI): Calcd. for C$_{18}$H$_{15}$BrO: 326.030626. Found: 326.030567.

2-(4-Methoxy-3-naphthalen-1-ylmethyl-phenyl)-4,4,5,5-tetramethyl-[1,3,2]dioxaborolane (64).

A solution of 839.2 mg (2.56 mmol) 1-(5-Bromo-2-methoxy-benzyl)-naphthalene (63), 689.5 mg (2.72 mmol, 1.06 eq.) bis(pinacolato)diboron, 768.8 mg (7.83 mmol, 3.06 eq.) KOAc and 106.8 mg (130.7 µmol, 0.05 eq.) PdCl$_2$dppf*CH$_2$Cl$_2$ in 16 ml DMSO was heated at 85° C. for 5 h. After that water was added and the mixture was extracted with CH$_2$Cl$_2$. The comb. org. fractions were washed with water, dried over MgSO$_4$ and evaporated. Column chromatography (hexanes/EtOAc (9+1)) yielded 638.5 mg (1.71 mmol, 66.64%) 2-(4-Methoxy-3-naphthalen-1-ylmethyl-phenyl)-4,4,5,5-tetramethyl-[1,3,2]dioxaborolane (64) as a white solid. R$_f$ (hexanes/EtOAc (9+1)): 0.19. $^1$H-NMR (500 MHz, CDCl$_3$): δ=1.26 (s, 12H, 4*CH$_3$), 3.79 (s, 3H, OMe), 4.40 (s, 2H), 6.90 (d, 1H, J=8.21 Hz), 7.04 (dd, 1H, J$_1$=7.07 Hz, J$_2$=1.01 Hz), 7.31 (m, 1H), 7.40-7.49 (m, 2H), 7.55 (d, 1H, J=1.64 Hz), 7.68 (m, 2H), 7.82 (m, 1H), 8.11 (m, 1H). MS (EI): m/z=375 (27), 374 (100), 373 (23), 274 (30), 273 (12), 259 (17), 241 (11), 216 (11), 215 (27), 147 (46), 146 (12), 142 (12), 141 (32), 117 (17), 83 (28). HR-MS (EI): Calcd. for C$_{24}$H$_{27}$BO$_3$: 373.208958. Found: 374.206159.

3-(2-Isobutyl-4'-methoxy-3'-naphthalen-1-ylmethyl-biphenyl-4-yl)propionitrile (65).

452 mg (1.35 mmol) 4-(2-Cyanoethyl)-2-isobutylphenyl-trifluormethanesulfonate (6), 637.8 mg (1.70 mmol, 1.26 eq.) 2-(4-Methoxy-3-naphthalen-1-ylmethyl-phenyl)-4,4,5,5-tetramethyl-[1,3,2]dioxaborolane (64) and 236.8 mg (205 µmol, 0.15 eq.) Pd(Ph$_3$P)$_4$ were dissolved in 20 ml DME/EtOH (9+1). To this yellow solution 1.35 ml (2.70 mmol, 2 eq.) of a 2 M aq. Na$_2$CO$_3$-solution was added and the resulting mixture was heated at 80° C. for 15 h. After concentrating the mixture in vacuo the residue was taken up in water and extracted with CH$_2$Cl$_2$. The comb. org. fractions were dried over MgSO$_4$ and evaporated. Column chromatography (hexanes/EtOAc (3+1)) yielded 513.8 mg (1.19 mmol, 87.78%) 3-(2-Isobutyl-4'-methoxy-3'-naphthalen-1-ylmethyl-biphenyl-4-yl)propionitrile (65) as a clear oil. $R_f$ (hexanes/EtOAc (3+1))=0.40. $^1$H-NMR (500 MHz, CDCl$_3$): δ=0.51 (d, 6H, J=6.62 Hz, 2*CH$_3$), 1.42 (m, 1H, CH), 2.17 (d, 2H, J=7.25 Hz, CH$_2$), 2.56 (t, 2H, J=7.41 Hz, CH$_2$CH$_2$CN), 2.87 (t, 2H, J=7.41 Hz, CH$_2$CH$_2$CN), 3.91 (s, 3H, OCH$_3$), 4.42 (s, 2H, CH$_2$Naphthyl), 6.71 (d, 1H, J=2.21 Hz), 6.94 (m, 3H), 7.00 (d, 1H, J=7.72 Hz), 7.04 (dd, 1H, J$_1$=8.36 Hz, J$_2$=2.36 Hz), 7.22 (m, 1H), 7.35 (m, 1H), 7.41 (m, 2H), 7.69 (d, 1H, J=8.20 Hz), 7.81 (m, 1H), 7.97 (m, 1H). MS (EI): m/z=434 (16), 433 (48), 336 (9), 335 (56), 294 (11), 293 (83), 292 (17), 277 (9), 265 (20), 264 (100), 253 (29). HR-MS (EI): Calcd. for C$_{31}$H$_{31}$NO: 433.240564. Found: 433.241264.

3-(4'-Hydroxy-2-isobutyl-3'-naphthalen-1-ylmethyl-biphenyl-4-yl)-propionitrile (66).

2.55 ml (2.55 mmol, 3.00 eq.) of a 1 M solution of BBr$_3$ in CH$_2$Cl$_2$ was added to a solution of 367.3 mg (0.85 mmol) 3-(2-Isobutyl-4'-methoxy-3'-naphthalen-1-ylmethyl-biphenyl-4-yl)propionitrile (65) in 40 ml dry CH$_2$Cl$_2$ at 0° C. via syringe. After that the solution was stirred for 2 h at 0° C. and then for 14 h at r.t. The reaction mixture was then added to water and extracted with CH$_2$Cl$_2$. The comb. org. fractions were dried over MgSO$_4$ and evaporated. Column chromatography (hexanes/EtOAc (2+1)) yielded 334.9 mg (0.80 mmol, 93.91%) 3-(4'-Hydroxy-2-isobutyl-3'-naphthalen-1-ylmethyl-biphenyl-4-yl)-propionitrile (66) as an oily white solid. $R_f$ (hexanes/EtOAc (2+1))=0.36. $^1$H-NMR (500 MHz, CDCl$_3$): δ=0.56 (d, 6H, J=6.62 Hz, 2*CH$_3$), 1.48 (m, 1H, CH), 2.26 (d, 2H, J=7.41 Hz, CH$_2$), 2.58 (t, 2H, J=7.41 Hz, CH$_2$CH$_2$CN), 2.89 (t, 2H, J=7.41 Hz, CH$_2$CH$_2$CN), 4.44 (s, 2H, CH$_2$Naphthyl), 4.80 (s, br., 1H, OH), 6.83 (d, 1H, J=8.20 Hz), 6.85 (d, 1H, J=2.05 Hz), 6.96-7.00 (m, 3H), 7.04 (d, 1H, J=7.41 Hz), 7.25 (m, 1H), 7.36 (m, 1H), 7.44 (m, 2H), 7.73 (d, 1H, J=8.20 Hz), 7.83 (m, 1H), 8.03 (m, 1H). MS (EI): m/z=419 (2), 335 (14), 293 (22), 253 (8), 161 (18), 160 (100), 91 (18). HR-MS (EI): Calcd. for C$_{30}$H$_{29}$NO: 419.224914. Found: 419.225626.

Trifluoro-methanesulfonic acid 4'-(2-cyano-ethyl)-2'-isobutyl-3-naphthalen-1-ylmethyl-biphenyl-4-yl-ester (67).

0.27 ml (1.61 mmol, 1.80 eq.) triflic anhydride was added to a solution of 374.0 mg (0.89 mmol) 3-(4'-Hydroxy-2-isobutyl-3'-naphthalen-1-ylmethyl-biphenyl-4-yl)-propionitrile (66) in 10 ml pyridine at 0° C. The resulting mixture was stirred at 0° C. for 60 min and then at r.t. for 19 h. After that water was added and the mixture was extracted with ether. The comb. org. fractions were washed with brine, dried over MgSO$_4$ and evaporated. Column chromatography (hexanes/EtOAc (1+1)) yielded 441.7 mg (0.80 mmol, 89.81%) Trifluoro-methanesulfonic acid 4'-(2-cyano-ethyl)-2'-isobutyl-3-naphthalen-1-ylmethyl-biphenyl-4-yl-ester (67) as a colorless oil. $R_f$ (hexanes/EtOAc (1+1))=0.64. $^1$H-NMR (500 MHz, CDCl$_3$): δ=0.43 (d, 6H, J=6.62 Hz, 2*CH$_3$), 1.31 (m, 1H, CH), 2.04 (d, 2H, J=7.25 Hz, CH$_2$), 2.55 (t, 2H, J=7.41 Hz, CH$_2$CH$_2$CN), 2.86 (t, 2H, J=7.41 Hz, CH$_2$CH$_2$CN), 4.52 (s, 2H, CH$_2$Naphthyl), 6.74 (d, 1H, J=2.21 Hz), 6.91-6.97 (m, 3H), 7.13 (dd, 1H, J$_1$=8.36 Hz, J$_2$=2.21 Hz), 7.28 (m, 1H), 7.34-7.45 (m, 4H), 7.75 (m, 1H), 7.78 (m, 1H), 7.82 (m, 1H). MS (EI): m/z=551 (18), 418 (9), 335 (14), 293 (22), 161 (16), 160 (100), 141 (14), 91 (16). HR-MS (EI): Calcd. for C$_{31}$H$_{29}$F$_3$NO$_3$S: 552.182025. Found: 551.174200.

3-(3,2"-Diisobutyl-4-methoxy-2'-naphthalen-1-ylmethyl-[1,1':4',1"]-terphenyl-4"-yl)propionitrile (68).

439.6 mg (0.80 mmol) Trifluoro-methanesulfonic acid 4'-(2-cyano-ethyl)-2'-isobutyl-3-naphthalen-1-ylmethyl-biphenyl-4-yl-ester (67), 266.2 mg (0.92 mmol, 1.15 eq.) 2-(3-isobutyl-4-methoxyphenyl)-4,4,5,5-tetramethyl-[1,3,2]dioxaborolane (11, FIG. 6) and 140.4 mg (121.4 μmol, 0.15 eq.) Pd(Ph$_3$P)$_4$ were dissolved in 15 ml DME/EtOH (9+1). To this yellow solution 0.80 ml (1.60 mmol, 2.00 eq.) of a 2 M aq. Na$_2$CO$_3$-solution was added and the resulting mixture was heated at 80° C. for 9 h. After concentrating the mixture in vacuo the residue was taken up in water and extracted with CH$_2$Cl$_2$. The comb. org. fractions were dried over MgSO$_4$ and evaporated. Column chromatography (CH$_2$Cl$_2$) yielded 426.5 mg (0.75 mmol, 94.23%) 3-(3,2"-Diisobutyl-4-methoxy-2'-naphthalen-1-ylmethyl-[1,1':4',1"]-terphenyl-4"-yl)propionitrile (68) as a clear oil. $R_f$ (hexanes/EtOAc (6+1))=0.12. $^1$H-NMR (500 MHz, CDCl$_3$): δ=0.52 (d, 6H, J=6.62 Hz, 2*CH$_3$), 0.77 (d, 6H, J=6.62 Hz, 2*CH$_3$), 1.47 (m, 1H, CH), 1.74 (m, 1H, CH), 2.24 (d, 2H, J=7.41 Hz, CH$_2$), 2.41 (d, 2H, J=7.25 Hz, CH$_2$), 2.58 (t, 2H, J=7.41 Hz, CH$_2$CH$_2$CN), 2.90 (t, 2H, J=7.41 Hz, CH$_2$CH$_2$CN), 3.79 (s, 3H, OCH$_3$), 4.39 (s, 2H, CH$_2$Naphthyl), 6.83 (d, 1H, J=8.36 Hz), 6.96 (m, 2H), 6.99 (dd, 1H, J$_1$=7.88 Hz, J$_2$=1.89 Hz), 7.08 (d, 1H, J=7.57 Hz), 7.11-7.17 (m, 3H), 7.22 (m, 1H), 7.30-7.35 (m, 3H), 7.38 (m, 1H), 7.67 (dm, 1H, J=7.88 Hz), 7.72 (dm, 1H, J=8.20 Hz), 7.78 (dm, 1H, J=8.20 Hz). MS (EI): m/z=565 (14), 452 (11), 410 (10), 404 (19), 403 (59), 349 (24), 306 (10), 290 (13), 247 (35), 191 (13), 142 (14), 141 (100). HR-MS (EI): Calcd. for C$_{41}$H$_{43}$NO: 565.334464. Found: 565.334575.

3-(4-Hydroxy-3,2"-diisobutyl-2'-naphthalen-1-ylmethyl-[1,1':4',1"]-terphenyl-4"-yl)propionitrile (69).

1.44 ml (1.44 mmol, 3.00 eq.) of a 1 M solution of BBr$_3$ in CH$_2$Cl$_2$ was added to a solution of 270.8 mg (0.48 mmol) 3-(3,2"-Diisobutyl-4-methoxy-2'-naphthalen-1-ylmethyl-[1,1':4',1"]-terphenyl-4"-yl)propionitrile (68) in 25 ml dry CH$_2$Cl$_2$ at 0° C. via syringe. After that the solution was stirred for 60 min at 0° C. and then for 12 h at r.t. The reaction mixture was then added to water and extracted with CH$_2$Cl$_2$. The comb. org. fractions were dried over MgSO$_4$ and evaporated. Column chromatography (hexanes/EtOAc (2+1)) yielded 261.9 mg (0.48 mmol, 98.89%) 3-(4-Hydroxy-3,2"-diisobutyl-2'-naphthalen-1-ylmethyl-[1,1':4',1"]-terphenyl-4"-yl)propionitrile (69) as a colorless oil. $R_f$ (hexanes/EtOAc (2+1))=0.40. $^1$H-NMR (500 MHz, CDCl$_3$): δ=0.53 (d, 6H, J=6.62 Hz, 2*CH$_3$), 0.79 (d, 6H, J=6.62 Hz, 2*CH$_3$), 1.47 (m, 1H, CH), 1.73 (m, 1H, CH), 2.24 (d, 2H, J=7.41 Hz, CH$_2$), 2.39 (d, 2H, J=7.09 Hz, CH$_2$), 2.58 (t, 2H, J=7.41 Hz, CH$_2$CH$_2$CN), 2.90 (t, 2H, J=7.41 Hz, CH$_2$C$_2$CN), 4.38 (s, 2H, CH$_2$Naphthyl), 4.58 (s, 1H, OH), 6.76 (d, 1H, J=8.04 Hz), 6.97 (m, 2H), 7.00 (m, 1H), 7.08-7.16 (m, 5H), 7.30-7.41 (m, 4H), 7.67 (dm, 1H, J=8.04 Hz), 7.72 (dm, 1H, J=8.51 Hz), 7.78 (dm, 1H, J=8.04 Hz). MS (EI): m/z=553 (11), 552 (43), 551 (100), 141 (49). HR-MS (EI): Calcd. for C$_{40}$H$_{41}$NO: 551.318814. Found: 551.318350.

3-(4-Cyanomethoxy-3,2"-diisobutyl-2'-naphthalen-1-ylmethyl-[1,1':4',1"]-terphenyl-4"-yl)propionitrile (70)

To a suspension of 374.5 mg (0.68 mmol) 3-(4-Hydroxy-3,2"-diisobutyl-2'-naphthalen-1-ylmethyl-[1,1':4',1"]-terphenyl-4"-yl)propionitrile (70) and 498.2 mg (3.61 mmol, 5.30 eq.) K$_2$CO$_3$ in 20 ml acetone 0.43 ml (6.79 mmol, 9.99 eq.) chloroacetonitrile was added. The resulting mixture was stirred for 24 h at 55° C. and then added to 100 ml of a mixture of brine/water (1+1). After extraction with EtOAc the combined org. fractions were washed with brine, dried over MgSO$_4$ and evaporated. Column chromatography (hexanes/EtOAc (2+1)) yielded 395.3 mg (0.67 mmol, 98.39%) 3-(4-Cyanomethoxy-3,2"-diisobutyl-2'-naphthalen-1-ylmethyl-[1,1':4':1"]-terphenyl-4"-yl)propionitrile (71) as a colorless oil. $R_f$ (hexanes/EtOAc (2+1))=0.37. $^1$H-NMR (500 MHz, CDCl$_3$): δ=0.55 (d, 6H, J=6.62 Hz, 2*CH$_3$), 0.75 (d, 6H, J=6.62 Hz, 2*CH$_3$), 1.48 (m, 1H, CH), 1.68 (m, 1H, CH), 2.26 (d, 2H, J=7.25 Hz, CH$_2$), 2.40 (d, 2H, J=7.09 Hz, CH$_2$), 2.59 (t, 2H, J=7.41 Hz, CH$_2$CH$_2$CN), 2.90 (t, 2H, J=7.41 Hz, CH$_2$CH$_2$CN), 4.36 (s, 2H, CH$_2$Naphthyl), 4.75 (s, 2H, OCH$_2$CN), 6.89 (d, 1H, J=8.51 Hz), 6.98-7.02 (m, 3H), 7.08-7.18 (m, 4H), 7.30-7.44 (m, 5H), 7.67 (dm, 1H, J=8.67 Hz), 7.72 (dm, 1H, J=8.20 Hz), 7.79 (dm, 1H, J=8.04 Hz). MS (EI): m/z=592 (12), 591 (50), 590 (100), 551 (5), 374 (4), 141 (44). HR-MS (EI): Calcd. for C$_{42}$H$_{42}$N$_2$O: 590.329713. Found: 590.329441.

3-(3,2"-Diisobutyl-4-methoxycarbonylmethoxy-2'-naphthalen-ylmethyl-[1,1':4',1"]-terphenyl-4"-yl)propionic methyl-ester (71)

A solution of 140.0 mg (0.24 mmol) 3-(4-Cyanomethoxy-3,2"-diisobutyl-2'-naphthalen-1-ylmethyl-[1,1':4',1"]-terphenyl-4"-yl)propionitrile (70) in 22 ml methanol was saturated with dried hydrogen chloride at r.t. Then the mixture was refluxed for 1.5 h under continuous passing of hydrogen chloride. After that nitrogen was passed through the solution at r.t. before ice-cold water was added to the mixture. After extracting the mixture with ether the comb. org. fractions were dried over Na$_2$SO$_4$ and evaporated. Column chromatography (hexanes/EtOAc (2+1)) yielded 139.3 mg (0.21 mmol, 88.33%) 3-(3,2"-Diisobutyl-4-methoxycarbonylmethoxy-2'-naphthalen-1-ylmethyl-[1,1':4',1"]-terphenyl-4"-yl)propionic acid methyl ester (71) as a colorless oil. $R_f$ (hexanes/EtOAc (2+1))=0.45. $^1$H-NMR (500 MHz, CDCl$_3$): δ=0.52 (d, 6H, J=6.62 Hz, 2*CH$_3$), 0.77 (d, 6H, J=6.62 Hz, 2*CH$_3$), 1.46 (m, 1H, CH), 1.78 (m, 1H, CH), 2.23 (d, 2H, J=7.41 Hz, CH$_2$), 2.46 (d, 2H, J=7.25 Hz, CH$_2$), 2.59 (t, 2H, J=7.41 Hz, CH$_2$CH$_2$CO$_2$Me), 2.89 (t, 2H, J=7.41 Hz, CH$_2$CH$_2$CO$_2$Me), 3.63 (s, 3H, CO$_2$Me), 3.76 (s, 3H, CO$_2$Me), 4.37 (s, 2H, CH$_2$Naphthyl), 4.62 (s, 2H, OCH$_2$CO$_2$Me), 6.68 (d, 1H, J=8.36 Hz), 6.93-6.98 (m, 3H), 7.01-7.05 (m, 1H), 7.12-7.19 (m, 4H), 7.30-7.40 (m, 4H), 7.66 (dm, 1H, J=8.20 Hz), 7.72 (dm, 1H, J=8.51 Hz), 7.78 (dm, 1H, J=8.51 Hz). $^{13}$C-NMR (125 MHz, CDCl$_3$): δ=22.22, 22.46, 28.65, 29.32, 30.62, 35.68, 36.62, 39.35, 41.87, 51.55, 52.08, 65.53, 110.92, 123.99, 125.32, 125.37, 125.41, 125.75, 126.78, 126.94, 127.28, 127.50, 128.50, 129.78, 129.90, 130.11, 130.47, 131.21, 131.92, 132.17, 133.79, 134.28, 137.10, 137.58, 139.04, 139.25, 140.00, 140.02, 140.83, 155.16, 169.57, 173.36. MS (EI): m/z=658 (15), 657 (50), 656 (100), 141 (38). HR-MS (EI): Calcd. for C$_{44}$H$_{48}$O$_5$: 656.350175. Found: 656.350300.

3-(4-(Carboxymethoxy)-3,2"-diisobutyl-2'-naphthalen-1-yl-methyl-[1,1':4',1"]-terphenyl-4"-yl)propionic acid (72).

To a solution of 50.6 mg (77.03 µmol) 3-(3,2"-Diisobutyl-4-methoxycarbonylmethoxy-2'-naphthalen-1-ylmethyl-[1,1':4',1"]-terphenyl-4"-yl)propionic acid methyl ester (71) in 8 ml 1.4-dioxane 2.8 ml (23.24 mmol, 302 eq.) 25% aq. NaOH-solution and 2.8 ml (4.31 mmol, 56 eq.) 40% aq. solution of Bu$_4$NOH were added. The resulting mixture was refluxed for 27 h and then cooled to 0° C. Acidification to pH 1 by adding 1 N aq. HCl-solution led to a white precipitate which was obtained by filtration. A filtration over silica gel with EtOAc/HOAc (95+5)) as an eluent and a following lyophilization of the obtained oily product from a solution in CH$_3$CN and aq. NH$_3$-solution yielded 51.0 mg (76.9 µmol, 100%) of the bisammonia-salt of 3-(4-(Carboxymethoxy)-3,2"-diisobutyl-2'-naphthalen-1-ylmethyl-[1,1':4',1"]-terphenyl-4"-yl)propionic acid (72) as a white solid. $R_f$ (CH$_2$Cl$_2$/MeOH (10+1))=0.20. $^1$H-NMR (500 MHz, d$_4$-MeOH): δ=0.47 (d, 6H, J=6.62 Hz, 2*CH$_3$), 0.79 (d, 6H, J=6.62 Hz, 2*CH$_3$), 1.38 (m, 1H, CH), 1.81 (m, 1H, CH), 2.22 (d, 2H, J=7.25 Hz, CH$_2$), 2.51 (d, 2H, J=7.25 Hz, CH$_2$), 2.56 (t, 2H, J=7.41 Hz, CH$_2$CH$_2$CO$_2$NH$_4$), 2.87 (t, 2H, J=7.41 Hz, CH$_2$CH$_2$CO$_2$NH$_4$), 4.40 (s, 2H, CH$_2$Naphthyl), 4.49 (s, 2H, OCH$_2$CO$_2$NH$_4$), 6.88 (d, 1H, J=8.83 Hz), 6.91 (d, 1H, J=1.73 Hz), 6.97-7.03 (m, 3H), 7.10-7.13 (m, 2H), 7.19-7.23 (m, 2H), 7.32 (d, 1H, J=7.72 Hz), 7.34-7.42 (m, 3H), 7.71 (m, 2H), 7.81 (m, 1H). $^{13}$C-NMR (125 MHz, d$_4$-MeOH): δ=22.66, 22.99, 29.74, 30.48, 32.01, 37.39, 37.76, 40.52, 43.18, 68.63, 112.78, 125.23, 126.39, 126.57, 126.60, 126.88, 127.99, 128.12, 128.29, 128.81, 129.63, 130.97, 131.03, 131.06, 131.41, 132.23, 132.87, 133.32, 133.81, 134.80, 135.52, 136.66, 138.69, 139.06, 140.21, 141.01, 141.37, 141.78, 142.29, 157.64. MS (FAB+): m/z=669 (18), 668 (45), 667 (100), 651 (13), 628 (12), 609 (11), 347 (11), 309 (19), 301 (10), 280 (18), 279 (95), 195 (20), 193 (20), 177 (15), 155 (32), 149 (66), 141 (26), 135 (21), 119 (70). HR-MS (FAB+): Calcd. for C$_{42}$H$_{44}$O$_5$: 628.318875. Found: 628.318800.

Figure 8:
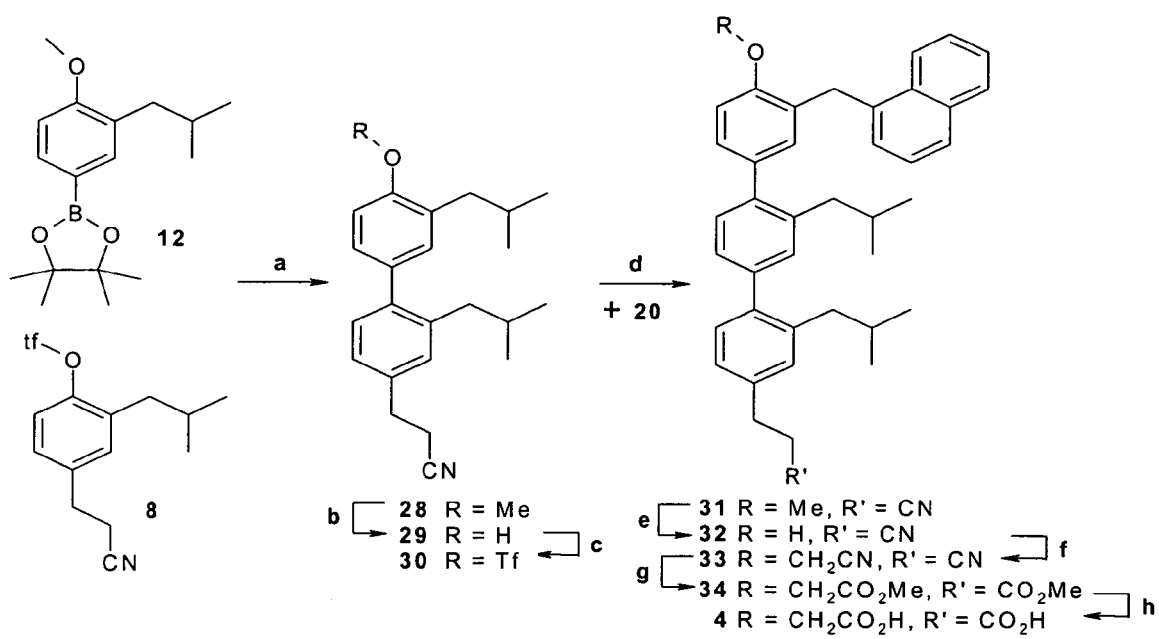
FIG. 8 represents the chemical synthesis of the terphenyl derivatives as indicated. The following legend applies to FIG. 8: a: Pd(Ph$_3$P)$_4$, DME/EtOH (9+1), 2 M aq. Na$_2$CO$_3$, 80° C., 17 h, 99%. b: BBr$_3$, CH$_2$Cl$_2$, 0° C. (3 h), r.t. (10 h), 9 h, 66%. c: Tf$_2$O, Py, 0° C. (3 h), r.t. (14 h), 84%. d: 20, Pd(Ph$_3$P)$_4$, DME/EtOH (9+1), 2 M aq. Na$_2$CO$_3$, 80° C., 22 h, 80%. e: BBr$_3$, CH$_2$Cl$_2$, 0° C. (3 h), r.t. (12 h), 63%. f: K$_2$CO$_3$, acetone, ClCH$_2$CN, 55° C., 40 h, 78%.g: HCl(g), MeOH, rfl., 1 h, 87%. h: 25% aq. NaOH, 40% aq. Bu$_4$NOH, 1,4-dioxane, rfl., 24 h, 100%.

Synthesis Following the Presentation in FIG. 8, Scheme 8

Synthesis of the 1-naphthalene-bisisobutyl-terphenyl-derivative (80).

3-(2,3'-Diisobutyl-4'-methoxy-biphenyl-4-yl)propionitrile (73).

294.8 mg (0.88 mmol) 4-(2-Cyanoethyl)-2-isobutylphenyl-trifluormethanesulfonate (6), 312.9 mg (1.08 mmol, 1.23 eq.) 2-(3-Isobutyl-4-methoxyphenyl)-4,4,5,5-tetramethyl-[1,3,2]dioxaborolane (11) and 156 mg (135 µmol, 0.15 eq.) Pd(Ph$_3$P)$_4$ were dissolved in 20 ml DME/EtOH (9+1). To this yellow solution 0.88 ml (1.76 mmol, 2.00 eq.) of a 2 M aq. Na$_2$CO$_3$-solution was added and the resulting mixture was heated at 80° C. for 17 h. After concentrating the mixture in vacuo the residue was taken up in water and extracted with CH$_2$Cl$_2$. The comb. org. fractions were dried over MgSO$_4$ and evaporated. Column chromatography (CH$_2$Cl$_2$) yielded 305.9 mg (0.88 mmol, 99.45%) 3-(2,3'-Diisobutyl-4'-methoxy-biphenyl-4-yl)propionitrile (73) as a clear oil. $R_f$ (CH$_2$Cl$_2$)=0.68. $^1$H-NMR (500 MHz, CDCl$_3$): δ=0.67 (d, 6H, J=6.62 Hz, 2*CH$_3$), 0.85 (d, 6H, J=6.62 Hz, CH$_2$), 2.59 (t, 2H, J=7.41 Hz, CH$_2$CH$_2$CN), 2.91 (t, 2H, J=7.41 Hz, CH$_2$CH$_2$CN), 3.79 (s, 3H, OCH$_3$), 6.80 (d, 1H, J=8.36 Hz), 6.94 (d, 1H, J=2.21 Hz), 6.98-7.04 (m, 3H), 7.09 (d, 1H, J=7.57 Hz). MS (EI): m/z=350 (23), 349 (90), 307 (10), 306 (35), 290 (39), 250 (15), 248 (17), 247 (100), 246 (24), 209 (21), 191 (16), 178 (10), 174 (10), 147 (10), 145 (17), 144 (19), 117 (13), 105 (25), 83 (11), 57 (18). HR-MS (EI): Calcd. for C$_{24}$H$_{31}$NO: 349.240564. Found: 349.240765.

3-(4'-Hydroxy-2,3'-diisobutyl-biphenyl-4-yl)-propionitrile (74).

2.37 ml (2.37 mmol, 3.00 eq.) of a 1 M solution of BBr$_3$ in CH$_2$Cl$_2$ was added to a solution of 275.6 mg (0.79 mmol) 3-(2,3'-Diisobutyl-4'-methoxy-biphenyl-4-yl)propionitrile (73) in 25 ml dry CH$_2$Cl$_2$ at 0° C. via syringe. After that the solution was stirred for 3 h at 0° C. and then for 10 h at r.t. The reaction mixture was then added to water and extracted with CH$_2$Cl$_2$. The comb. org. fractions were dried over MgSO$_4$ and evaporated. Column chromatography (hexanes/EtOAc (2+1)) yielded 174.9 mg (0.52 mmol, 65.99%) 3-(4'-Hydroxy-2,3'-diisobutyl-biphenyl-4-yl)-propionitrile (74) as an oily white solid. $R_f$ (hexanes/EtOAc (2+1)) =0.38. $^1$H-NMR (500 MHz, CDCl$_3$): δ=0.69 (d, 6H, J=6.62 Hz, 2*CH$_3$), 0.92 (d, 6H, J=6.62 Hz, 2*CH$_3$), 1.63 (m, 1H, CH), 1.93 (m, 1H, CH), 2.45 (d, 2H, J=7.25 Hz, CH$_2$), 2.47 (d, 2H, J=7.25 Hz, CH$_2$), 2.62 (t, 2H, J=7.41 Hz, CH$_2$CH$_2$CN), 2.94 (t, 2H, J=7.41 Hz, CH$_2$CH$_2$CN), 4.60 (s, br., 1H, OH), 6.75 (d, 1H, J=8.36 Hz), 6.92-6.96 (m, 2H), 7.01-7.06 (m, 2H), 7.11 (d, 1H, J=7.57 Hz). MS (EI): m/z=336 (24), 335 (100), 292 (18), 251 (10), 236 (35), 209 (12), 196 (10), 195 (48), 178 (10), 165 (10). HR-MS (EI): Calcd. for C$_{23}$H$_{29}$NO: 335.224914. Found: 335.225330.

Trifluoro-methanesulfonic acid 4'-(2-cyano-ethyl)-3,2'-diisobutyl-biphenyl-4-yl-ester (75).

0.16 ml (0.95 mmol, 1.83 eq.) triflic anhydride was added to a solution of 173.2 mg (0.52 mmol) 3-(4'-Hydroxy-2,3'-diisobutyl-biphenyl-4-yl)-propionitrile (74) in 10 ml pyridine at 0° C. The resulting mixture was stirred at 0° C. for 3 h and then at r.t. for 14 h. After that water was added and the mixture was extracted with ether. The comb. org. fractions were washed with brine, dried over MgSO$_4$ and evaporated. Column chromatography (hexanes/EtOAc (1+1)) yielded 203.3 mg (0.43 mmol, 83.62%) Trifluoro-methanesulfonic acid 4'-(2-cyano-ethyl)-3,2'-diisobutyl-biphenyl-4-yl-ester (75) as a colorless oil. R$_f$ (hexanes/EtOAc (1+1))= 0.68. $^1$H-NMR (500 MHz, CDCl$_3$): δ=0.69 (d, 6H, J=6.62 Hz, 2*CH$_3$), 0.91 (d, 6H, J=6.62 Hz, 2*CH$_3$), 1.59 (m, 1H, CH), 1.94 (m, 1H, CH), 2.42 (d, 2H, J=7.25 Hz, CH$_2$), 2.58 (d, 2H, J=7.25 Hz, CH$_2$), 2.63 (t, 2H, J=7.41 Hz, CH$_2$CH$_2$CN), 2.95 (t, 2H, J=7.41 Hz, CH$_2$CH$_2$CN), 7.06-7.16 (m, 5H), 7.25 (d, 1H, J=8.20 Hz). MS (EI): m/z=469 (9), 468 (28), 467 (100), 425 (10), 368 (12), 335 (19), 334 (72), 327 (11), 293 (16), 292 (52), 279 (19), 278 (39), 251 (12), 250 (19), 248 (11), 237 (17), 236 (16), 235 (15), 233 (10), 209 (12), 207 (12), 195 (17), 179 (16), 178 (12), 165 (14), 105 (10). HR-MS (EI): Calcd. for C$_{24}$H$_{28}$F$_3$NO$_3$S: 467.174201. Found: 467.173888.

3-(2',2"-Diisobutyl-4-methoxy-3-naphthalen-1-ylmethyl-[1,1':4', 1"]-terphenyl-4"-yl)propionitrile (76).

202.8 mg (0.43 mmol) Trifluoro-methanesulfonic acid 4'-(2-cyano-ethyl)-3,2'-diisobutyl-biphenyl-4-yl-ester (75), 186.7 mg (0.50 mmol, 1.16 eq.) 2-(4-Methoxy-3-naphthalen-1-ylmethyl-phenyl)-4,4,5,5-tetramethyl-[1,3,2]dioxaborolane (64) and 74.5 mg (64.4 μmol, 0.15 eq.) Pd(Ph$_3$P)$_4$ were dissolved in 10 ml DME/EtOH (9+1). To this yellow solution 0.43 ml (0.86 mmol, 2.00 eq.) of a 2 M aq. Na$_2$CO$_3$-solution was added and the resulting mixture was heated at 80° C. for 22 h. After concentrating the mixture in vacuo the residue was taken up in water and extracted with CH$_2$Cl$_2$. The comb. org. fractions were dried over MgSO$_4$ and evaporated. Column chromatography (CH$_2$Cl$_2$) yielded 194.3 mg (0.34 mmol, 79.86%) 3-(2',2"-Diisobutyl-4-methoxy-3-naphthalen-1-ylmethyl-[1,1':4',1"]-terphenyl-4"-yl)propionitrile (76) as a clear oil. R$_f$ (hexanes/EtOAc (6+1))= 0.23. $^1$H-NMR (500 MHz, CDCl$_3$): δ=0.52 (d, 6H, J=6.62 Hz, 2*CH$_3$), 0.69 (d, 6H, J=6.62 Hz, 2*CH$_3$), 1.46 (m, 1H, CH), 1.64 (m, 1H, CH), 2.23 (d, 2H, J=7.41 Hz, CH$_2$), 2.45 (d, 2H, J=7.41 Hz, CH$_2$), 2.61 (t, 2H, J=7.41 Hz, CH$_2$CH$_2$CN), 2.93 (t, 2H, J=7.41 Hz, CH$_2$CH$_2$CN), 3.91 (s, 3H, OCH$_3$), 4.44 (s, 2H, CH$_2$Naphthyl), 6.84 (d, 1H, J=2.21 Hz), 6.95 (d, 1H, J=8.67 Hz), 6.97-7.16 (m, 8H), 7.36 (m, 1H), 7.41-7.45 (m, 2H), 7.70 (m, 1H), 7.81 (m, 1H), 8.01 (m, 1H). MS (EI): m/z=565 (23), 468 (30), 467 (100), 425 (13), 374 (11), 368 (13), 335 (23), 334 (72), 327 (13), 324 (17), 319 (31), 293 (22), 292 (55), 279 (14), 278 (45), 277 (13), 276 (17), 264 (24), 263 (19), 251 (13), 250 (24), 249 (26), 248 (89), 237 (20), 236 (18), 235 (22), 234 (15), 233 (26), 221 (20), 220 (37), 217 (25), 215 (31), 179 (71), 178 (57), 165 (30), 160 (20), 142 (22), 141 (62), 115 (15), 91 (14), 57 (86), 55 (16). HR-MS (EI): Calcd. for C$_{41}$H$_{43}$NO: 565.334464. Found: 565.334507.

3-(4-Hydroxy-2',2"-diisobutyl-3-naphthalen-1-ylmethyl-[1,1':4',1"]terphenyl-4"-yl)propionitrile (77).

1.02 ml (1.02 mmol, 3.00 eq.) of a 1 M solution of BBr$_3$ in CH$_2$Cl$_2$ was added to a solution of 192.9 mg (0.34 mmol) 3-(2',2"-Diisobutyl-4-methoxy-3-naphthalen-1-ylmethyl-[1,1':4', 1"]-terphenyl-4"-yl)propionitrile (76) in 20 ml dry CH$_2$Cl$_2$ at 0° C. via syringe. After that the solution was stirred for 3 h at 0° C. and then for 12 h at r.t. The reaction mixture was then added to water and extracted with CH$_2$Cl$_2$. The comb. org. fractions were dried over MgSO$_4$ and evaporated. Column chromatography (hexanes/EtOAc (2+1)) yielded 117.9 mg (0.21 mmol, 62.85%) 3-(4-Hydroxy-2',2"-diisobutyl-3-naphthalen-1-ylmethyl-[1,1':4', 1"]terphenyl-4"-yl)propionitrile (32) as a colorless oil. R$_f$ (hexanes/EtOAc (2+1))=0.37. $^1$H-NMR (500 MHz, CDCl$_3$): δ=0.59 (d, 6H, J=6.62 Hz, 2*CH$_3$), 0.70 (d, 6H, J=6.78 Hz, 2*CH$_3$), 1.50 (m, 1H, CH), 1.65 (m, 1H, CH), 2.32 (d, 2H, J=7.25 Hz, CH$_2$), 2.47 (d, 2H, J=7.25 Hz, CH$_2$), 2.62 (t, 2H, J=7.41 Hz, CH$_2$CH$_2$CN), 2.94 (t, 2H, J=7.41 Hz, CH$_2$CH$_2$CN), 4.47 (s, 2H, CH$_2$Naphthyl), 4.80 (s, 1H, OH), 6.86 (d, 1H, J=8.36 Hz), 6.98-7.16 (m, 9H), 7.38 (m, 1H), 7.43-7.48 (m, 2H), 7.73 (dm, 1H, J=8.73 Hz), 7.83 (m, 1H), 8.06 (m, 1H). MS (EI): m/z=552 (30), 551 (65), 446 (21), 419 (21), 178 (19), 155 (15), 149 (24), 142 (18), 141 (100), 128 (28), 97 (23), 85 (26), 83 (25), 71 (39), 69 (30), 57 (74), 55 (35). HR-MS (EI): Calcd. for C$_{40}$H$_{41}$NO: 551.318814. Found: 551.318768.

3-(4-Cyanomethoxy-2',2"-diisobutyl-3-naphthalen-1-ylmethyl-[1,1":4',1"]-terphenyl-4"-yl)propionitrile (78)

To a suspension of 115.9 mg (0.21 mmol) 3-(4-Hydroxy-2',2"-diisobutyl-3-naphthalen-1-ylmethyl-[1,1':4',1"]terphenyl-4"-yl)propionitrile (77) and 166.0 mg (1.20 mmol, 5.72 eq.) K$_2$CO$_3$ in 20 ml acetone 0.13 ml (2.05 mmol, 9.78 eq.) a-chloroacetonitrile was added. The resulting mixture was stirred for 40 h at 55° C. and then added to 100 ml of a mixture of brine/water (1+1). After extraction with EtOAc the combined org. fractions were washed with brine, dried over MgSO$_4$ and evaporated. Column chromatography (hexanes/EtOAc (2+1)) yielded 96.2 mg (0.16 mmol, 77.54%) 3-(4-Cyanomethoxy-2',2"-diisobutyl-3-naphthalen-1-ylmethyl-[1,1':4',1"]terphenyl-4"-yl)propionitrile (78) as a colorless oil. R$_f$ (hexanes/EtOAC (2+1))=0.33. $^1$H-NMR (500 MHz, CDCl$_3$): δ=0.54 (d, 6H, J=6.62 Hz, 2*CH$_3$), 0.69 (d, 6H, J=6.62 Hz, 2*CH$_3$), 1.47 (m, 1H, CH), 1.64 (m, 1H, CH), 2.24 (d, 2H, J=7.25 Hz, CH$_2$), 2.45 (d, 2H, J=6.94 Hz, CH$_2$), 2.62 (t, 2H, J=7.41 Hz, CH$_2$CH$_2$CN), 2.94 (t, 2H, J=7.41 Hz, CH$_2$CH$_2$CN), 4.46 (s, 2H, CH$_2$Naphthyl), 4.83 (s, 2H, OCH$_2$CN), 6.95 (d, 1H, J=2.05 Hz), 6.99-7.08 (m, 5H), 7.11 (d, 1H, J=7.72 Hz), 7.18-7.22 (m, 2H), 7.33-7.38 (m, 2H), 7.42-7.48 (m, 2H), 7.72 (dm, 1H, J=8.36 Hz), 7.83 (m, 1H), 7.99 (m, 1H). MS (EI): m/z=592 (11), 591 (46), 590 (100), 550 (14), 142 (10), 141 (77), 57 (20). HR-MS (EI): Calcd. for C$_{42}$H$_{42}$N$_2$O: 590.329713. Found: 590.329806.

3-(2',2"-Diisobutyl-4'-methoxycarbonylmethoxy-3-naphthalen-1-ylmethyl-[1,1":4', 1"]-terphenyl-4"-yl)propionic acid methyl ester (79)

A solution of 89.1 mg (0.15 mmol) 3-(4-Cyanomethoxy-2',2"-diisobutyl-3-naphthalen-1-ylmethyl-[1,1':4',1"]terphenyl-4"-yl)propionitrile (78) in 30 ml methanol was saturated with dried hydrogen chloride at r.t. Then the mixture was refluxed for 1 h under continuous passing of hydrogen chloride. After that nitrogen was passed through the solution at r.t. before ice-cold water was added to the mixture. After extracting the mixture with ether the comb. org. fractions were washed with brine and dried over Na$_2$SO$_4$ and evaporated. Column chromatography (hexanes/EtOAc (2+1))

yielded 85.4 mg (0.13 mmol, 86.68%) 3-(2',2"-Diisobutyl-4-methoxycarbonylmethoxy-3-naphthalen-1-ylmethyl-[1,1':4',1"]-terphenyl-4"-yl)propionic acid methyl ester (79) as a colorless oil. $R_f$ (hexanes/EtOAc (2+1))=0.48. $^1$H-NMR (500 MHz, CDCl$_3$): δ=0.51 (d, 6H, J=6.46 Hz, 2*CH$_3$), 0.67 (d, 6H, J=6.46 Hz, 2*CH$_3$), 1.44 (m, 1H, CH), 1.61 (m, 1H, CH), 2.20 (d, 2H, J=7.25 Hz, CH$_2$), 2.43 (d, 2H, J=7.25 Hz, CH$_2$), 2.63 (t, 2H, J=7.57 Hz, CH$_2$CH$_2$CO$_2$Me), 2.92 (t, 2H, J=7.57 Hz, CH$_2$CH$_2$CO$_2$Me), 3.65 (s, 3H, CO$_2$Me), 3.80 (s, 3H, CO$_2$Me), 4.53 (s, 2H, CH$_2$Naphthyl), 4.73 (s, 2H, OCH$_2$CO$_2$Me), 6.81 (d, 1H, J=8.67 Hz), 6.88 (d, 1H, J=1.89 Hz), 6.97-7.07 (m, 6H), 7.09 (dd, 1H, J$_1$=8.04 Hz, J$_2$=2.05 Hz), 7.28 (m, 1H), 7.36 (m, 1H), 7.40-7.44 (m, 2H), 7.70 (dm, 1H, J=8.36 Hz), 7.81 (m, 1H), 8.05 (m, 1H). $^{13}$C-NMR (125 MHz, CDCl$_3$): δ=22.18, 22.34, 29.27, 29.49, 30.67, 32.59, 35.74, 41.94, 42.06, 51.57, 52.16, 65.77, 110.98, 124.38, 125.35, 125.41, 125.47, 125.86, 126.49, 126.91, 127.13, 128.21, 128.53, 129.09, 129.63, 129.78, 130.19, 130.92, 131.69, 132.27, 133.86, 135.46, 136.46, 138.64, 139.00, 139.24, 139.92, 140.24, 140.42, 154.39, 169.58, 173.40. MS (EI): m/z=658 (12), 657 (52), 656 (100), 524 (9), 141 (52), 91 (11), 85 (13), 57 (21), 55 (14). MS (FAB+): m/z=658 (14), 657 (49), 656 (100), 655 (11), 530 (10), 529 (24), 141 (79). HR-MS (FAB+): Calcd. for C$_{44}$H$_{48}$O$_5$: 656.350175. Found: 656.350400.

3-(4-(Carboxymethoxy)-2,2"-diisobutyl-3-naphthalen-1-yl-methyl-[1,1':4',1"]-terphenyl-4"-yl)propionic acid (80).

To a solution of 36.3 mg (55.26 µmol) 3-(2',2"-Diisobutyl-4-methoxycarbonylmethoxy-3-naphthalen-1-ylmethyl-[1,1':4',1"]-terphenyl-4"-yl)propionic acid methyl ester (79) in 8 ml 1.4-dioxane 2.0 ml (16.60 mmol, 301 eq.) 25% aq. NaOH-solution and 2.0 ml (3.08 mmol, 56 eq.) 40% aq. solution of Bu$_4$NOH were added. The resulting mixture was refluxed for 24 h and then cooled to 0° C. Acidification to pH 1 by adding 1 N aq. HCl-solution led to a white precipitate which was obtained by filtration. A filtration over silica gel with EtOAc/HOAc (95+5) as an eluent and a following lyophilization of the obtained oily product from a solution in CH$_3$CN and aq. NH$_3$-solution yielded 36.6 mg (55.2 µmol, 100%) of the bisammonia-salt of 3-(4-(Carboxymethoxy)-2,2"-diisobutyl-3-naphthalen-1-ylmethyl-[1,1':4',1"]-terphenyl-4"-yl)propionic acid (80) as a white solid. $R_f$ (hexanes/EtOAc (1+1), sample dissolved in HOAc)=0.49. $^1$H-NMR (500 MHz, d$_4$-MeOH): δ=0.43 (d, 6H, J=6.62 Hz, 2*CH$_3$), 0.65 (d, 6H, J=6.62 Hz, 2*CH$_3$), 1.35 (m, 1H, CH), 1.58 (m, 1H, CH), 2.14 (d, 2H, J=7.41 Hz, CH$_2$), 2.44 (d, 2H, J=7.25 Hz, CH$_2$), 2.56 (t, 2H, J=7.41 Hz, CH$_2$CH$_2$CO$_2$NH$_4$), 2.90 (t, 2H, J=7.57 Hz, CH$_2$CH$_2$CO$_2$NH$_4$), 4.58 (s, 2H, CH$_2$Naphthyl), 4.59 (s, 2H, OCH$_2$CO$_2$NH$_4$), 6.62 (d, 1H, J=2.05 Hz), 6.89-7.08 (m, 8H), 7.38-7.45 (m, 4H), 7.73 (m, 1H), 7.83 (m, 1H), 8.08 (m, 1H). $^{13}$C-NMR (125 MHz, d$_4$-MeOH): δ=22.97, 23.13, 30.75, 31.02, 32.69, 33.91, 38.49, 43.45, 43.73, 68.54, 112.71, 126.33, 126.85, 126.92, 126.99, 127.26, 128.00, 128.35, 129.01, 129.22, 129.90, 130.84, 131.09, 131.41, 131.49, 132.31, 132.42, 134.19, 135.91, 135.95, 138.60, 140.16, 140.53, 141.56, 141.86, 142.22, 142.28, 157.00, 177.34, 178.03. MS (FAB-): m/z=629 (18), 628 (29), 627 (54), 570 (42), 569 (100), 568 (16), 567 (24), 527 (24), 526 (30), 525 (70), 524 (30), 523 (58), 481 (30), 347 (14), 153 (96). HR-MS (FAB-): not possible.

Figure 9:
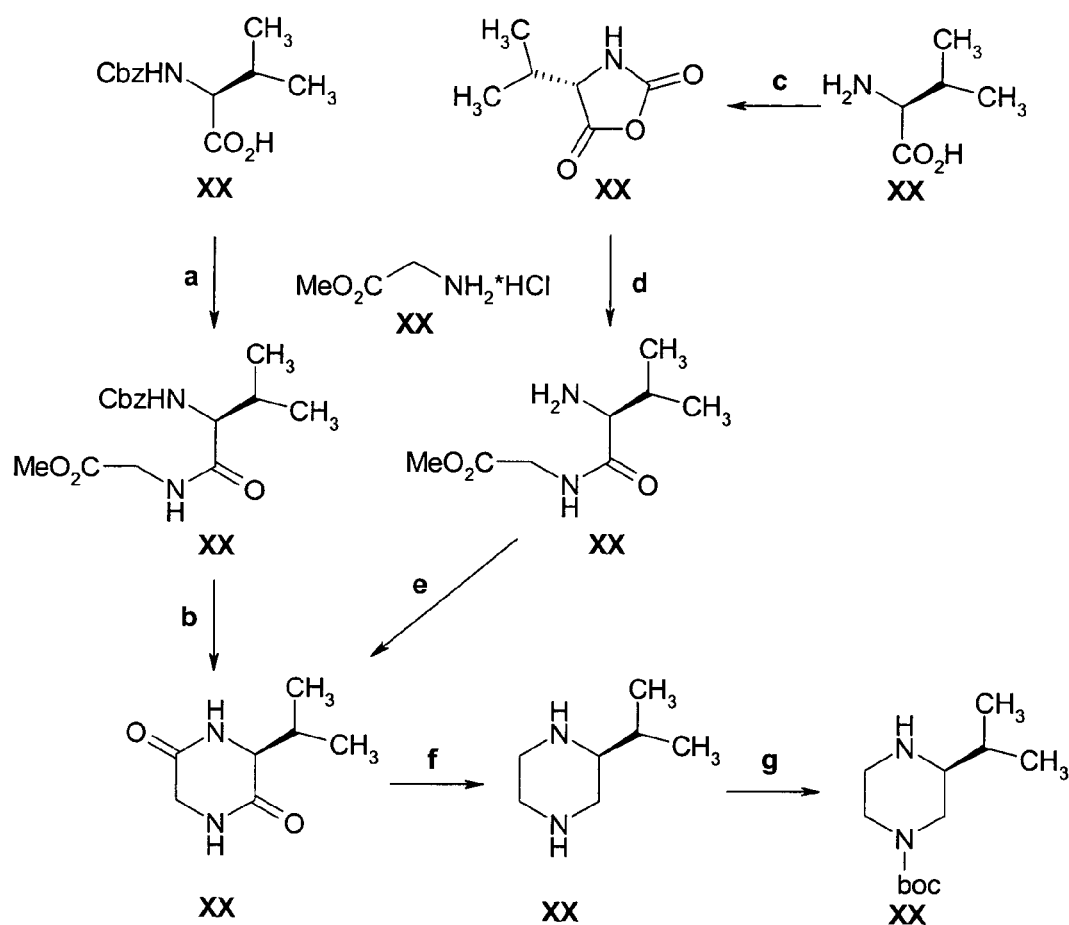
FIG. 9 represents the chemical synthesis of the piperazine derivatives as indicated. The following legend applies to FIG. 9: a: (i) 4-methylmorpholine, EtOAc, −15° C.; (ii) ethyl chloroformate, 15 min, −15° C.; (iii) 4-methylmorpholine, 1 h (−15° C.), 12 h (r.t.), (93%). b: (i) Pd/C, H$_2$, MeOH, r.t., 4 h; (ii) MeOH, rfl., 24 h, (100%). c: (i) COCl$_2$ (20% soln. in toluene), THF, 55° C., 4 h, (47%). d: (i) NEt$_3$, CHCl$_3$, −78° C. (3 h), −20° C. (12 h). e: (i) toluene, rfl., 24 h, (21%). f: (i) 1.) BH$_3$*THF, THF, rfl., 30 h; 2.) 30% HBr in HOAc; 3.) NH$_4$OH, (94%). g: Boc$_2$O, t-BuOH, H$_2$O, 2.5 N aq. NaOH, 0° C. (1 h), r.t. (24 h), (98%).
Figure 10:
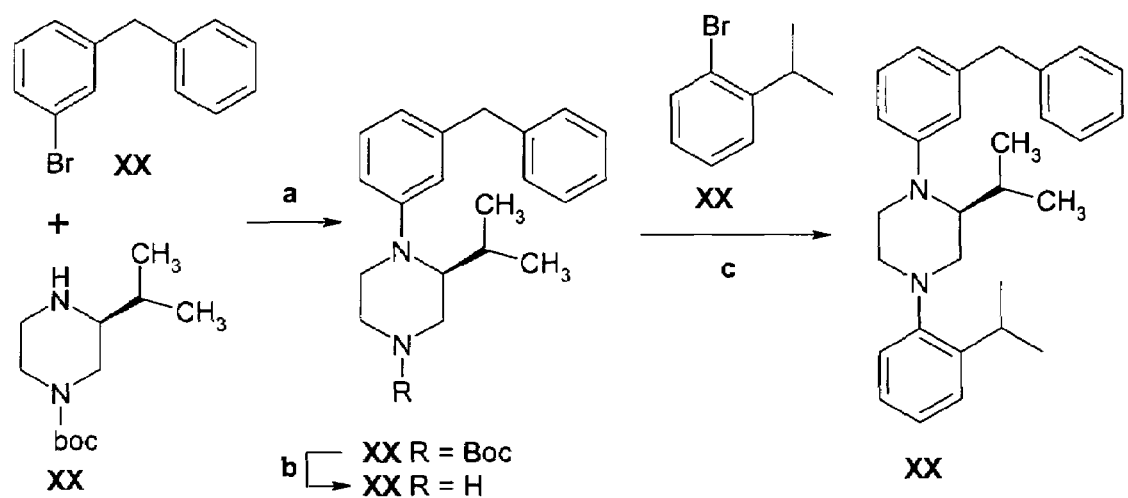
FIG. 10 represents the chemical synthesis of the piperazine derivatives as indicated. The following legend applies to FIG. 10: a: Pd$_2$(dba)$_3$, P(o-tolyl)$_3$, toluene, NaOt-Bu, 100° C., 19 h, (19%); (23%). b: Pd$_2$(dba)$_3$, P(o-tolyl)$_3$, toluene, NaOt-Bu, 100° C., 19 h, (11%).

Synthesis of Piperazine Derivatives Following the Presentation in FIG. 9, Scheme 9, and FIG. 10, Scheme 10

Synthesis of the Isopropyl-substituted Piperazine Derivative

Route A

N-Benzyloxycarbonyl-valine-glycine-methylester (82)

A solution of 2.30 ml (20.92 mmol, 1.06 eq.) 4-methylmorpholine in 2.5 ml EtOAc was added slowly to a suspension of 4.97 g (19.77 mmol) Z-valine (81) in 40 ml EtOAc at −15 ° C., followed by a solution of 1.90 ml (19.87 mmol, 1.01 eq.) ethyl chloroformate in 5 ml EtOAc. The resulting mixture was stirred for 15 min at −15° C. before a solution of 2.30 ml (20.92 mmol, 1.06 eq.) 4-methylmorpholine in 2.5 ml EtOAc, followed by 2.47 g (19.67 mmol, 1.00 eq.) glycine methylester-hydrochloride were added slowly. After stirring the mixture for another 60 min. at −15° C. and 12 h at r.t. 20 ml water and 20 ml EtOAc were added. The aq. layer was extracted with EtOAc and the comb. org. fractions were washed successively with sat. aq. NaHCO$_3$-solution, brine, 2% HCl-solution and brine. After drying the org. layer over Na$_2$SO$_4$ and evaporation of the solvent 5.95 g (18.46 mmol, 93.39%) N-Benzyloxycarbonyl-valine-glycine-methylester (82) was obtained as a white solid.

$^1$H-NMR (500 MHz, CDCl$_3$): δ=0.94 (d, 3H, J=6.94 Hz, CH$_3$), 0.99 (d, 3H, J=6.78 Hz, CH$_3$), 2.18 (m, 1H, CH, i-prop.), 3.76 (s, 3H, OCH$_3$), 3.99-4.13 (m, 3H, CH and CH$_2$), 5.11 (m, 2H, CH$_2$Ph), 5.38 (d, 1H, J=8.20 Hz, NH), 6.48 (s, br., 1H, NH), 7.30-7.40 (m, 5H, Ph).

6-(S)-Isopropyl-piperazine-2,5-dione (83).

Route A:

170 mg Pd/C-catalyst and 35 ml (345.53 mmol, 18.91 eq.) cyclohexene were added to a solution of 5.89 g (18.27 mmol) N-Benzyloxycarbonyl-valine-glycine-methylester (82) in 60 ml dry methanol. After refluxing the resulting mixture for 5 h the solvent was evaporated. The residue was then suspended in 70 ml dry methanol and heated at 65° C. for 110 h. Then the solvent was evaporated, the residue was dissolved in hot water and filtered through celite. After evaporation of the solvent the residue was suspended in 100 ml acetone and heated at 60° C. for 3 h. Cooling of this solution led to the precipitation of a white solid, which was filtered and dried in HV. This led to 1.43 g (9.13 rnmol, 50.00%) 6-(S)-Isopropyl-piperazine-2,5-dione (83) as a white solid.

Route B:

A solution of 27.14 g (84.19 mmol) N-Benzyloxycarbonyl-valine-glycine-methylester (82) in 600 ml dry methanol was hydrogenated by adding Pd/C-catalyst and stirring the resulting mixture under H$_2$ at r.t. for 4 h. After that the mixture was filtered through celite and the remaining solution was refluxed for 24 h. Evaporation of the solvent yielded 13.17 g (84.33 mmol, 100%) 6-(S)-Isopropyl-piperazine-2,5-dione (83) as a white solid.

$^1$H-NMR (400 MHz, D$_2$O): δ=0.56 (d, 3H, J=6.95 Hz, CH$_3$), 0.65 (d, 3H, J=7.07 Hz, CH$_3$), 1.90 (m, 1H, CH, i-prop.), 3.55 (dt, 1H, X-part of a ABX-system, J$_1$=3.66 Hz, J$_{AX}$=J$_{BX}$=1.14 Hz, CH, ring), 3.59 (dd, 1H, B-part of a ABX-system, J$_{AB}$=20.00 Hz, J$_{BX}$=1.14 Hz, CH$_2$, ring), 3.76 (dd, 1H, A-part of a ABX-system, J$_{AB}$=20.00 Hz, J$_{AX}$=1.14 Hz, CH$_2$, ring).

2-(S)-Isopropyl-piperazine (84).

Route A:

203.3 mg (1.30 mmol) 6-(S)-Isopropyl-piperazine-2,5-dione (83) was added by portion to a suspension of 248 mg (6.53 mmol, 5.03 eq.) lithium aluminum hydride in 25 ml dry THF at 0 ° C. The resulting mixture was heated at 65° C. for 72 h, then 0.8 ml (6.03 mmol, 4.64 eq.) triethanolamine was added at r.t. and the mixture was stirred for another hour at r.t. After adding 0.8 ml (44.44 mmol, 34.19 eq.) of water and stirring for another 12 h at r.t. the mixture was filtered and evaporated. The resulting oil was dissolved in 10% aq. HCl-solution and washed with ether. After that the pH of the aq. layer was adjusted to 10-12 by adding NaOH-pellets and then the aq. layer was extracted with CH$_2$Cl$_2$. The comb. org. fractions were dried over Na$_2$SO$_4$ and evaporated. This led to 52.8 mg (0.41 mmol, 31.68%) 2-(S)-Isopropyl-piperazine (84) as colorless crystals.

Route B:

120 ml (120 mmol, 6.25 eq.) of a 1M solution of BH3*THF in THF were added via syringe to a suspension of 3.00 g (19.21 mmol) 6-(S)-Isopropyl-piperazine-2,5-dione (82) in 100 ml dry THF at r.t. After heating the reaction mixture for 4 h under reflux another 110 ml (110 mmol, 5.73 eq.) of a 1M solution of BH$_3$*THF in THF were added via syringe. Then the reaction mixture was refluxed for another 26 h and filtered after that. Then the solution was cooled in ice and treated with ca. 50 ml 30% HBr in HOAc. After stirring the mixture overnight at r.t. the precipitate was collected by filtration and dried under HV. Column chromatography (CH$_2$Cl$_2$/MeOH/NH$_4$OH (16+2+1)) yielded 2.31 g (17.99 mmol, 93.65%) 2-(S)-Isopropyl-piperazine (84) as a white solid.

$^1$H-NMR (500 MHz, CDCl$_3$): δ=0.91 (d, 3H, J=6.78 Hz, CH$_3$), 0.94 (d, 3H, J=6.78 Hz, CH$_3$), 1.53 (m, 1H, CH, i-prop.), 2.33 (m, 1H, CH, ring), 2.42 (m, 1H, CH, ring), 2.67-2.82 (m, 2H, CH, ring), 2.89 (m, 1H, CH, ring), 3.01 (m, 2H, CH, ring).

3-(S)-Isopropyl-piperazine-1-carboxylic acid tert-butyl ester (85).

Route A:

341 mg (2.66 mmol) 2-(S)-Isopropyl-piperazine (84) and 657 mg (2.67 mmol, 1.00 eq.) BOC-ON© (2-(tert-Butoxycarbonyloxyimino)-2-phenylacetonitrile) were dissolved in 20 ml 1,4-dioxane and 20 ml water. After adding 2.04 ml (14.64 mmol, 5.50 eq.) triethylamine the solution was stirred at r.t. for 24 h. Then the mixture was added to water and extracted with EtOAc. The comb. org. fractions were washed with brine, dried over Na$_2$SO$_4$ and evaporated. Column chromatography (CH$_2$Cl$_2$/MeOH (3+1)) yielded 454.9 mg (1.99 mmol, 74.90%) 3-(S)-Isopropyl-piperazine-1-carboxylic acid tert-butyl ester (85) as a clear oil.

Route B:

5.68 ml (14.20 mmol, 1.00 eq.) of a 2.5 N aq. NaOH-solution were added to a solution of 1.82 g (14.19 mmol) 2-(S)-Isopropyl-piperazine (82) in 70 ml tert-Butanol and 70 ml H$_2$O. After cooling to 0° C. 3.10 g (14.20 mmol, 1.00 eq.) Boc-anhydride was added and the mixture was stirred at 0° C. for 1 h. Then the solution was warmed to r.t. and stirred overnight. After evaporating the tert-Butanol the mixture was extracted with CH$_2$Cl$_2$. The comb. org. fractions were dried over Na$_2$SO$_4$ and evaporated. Column chromatography (CH$_2$Cl$_2$/MeOH (10+1)) yielded 3.19 g (13.96 mmol, 98.37%) 3-(S)-Isopropyl-piperazine-1-carboxylic acid tert-butyl ester (85) as a clear oil.

R$_f$ (CH$_2$Cl$_2$/MeOH (3+1))=0.71. $^1$H-NMR (500 MHz, CDCl$_3$): δ=0.95 (d, 3H, J=6.82 Hz, CH$_3$), 0.97 (d, 3H, J=6.82 Hz, CH$_3$), 1.47 (s, 9H, t-Bu), 1.58 (m, 1H, CH, i-prop.), 2.30 (m, 1H, CH, ring), 2.50 (m, 1H, CH, ring), 2.68-2.85 (m, 2H, CH, ring), 2.99 (m, 1H, CH, ring), 3.86-4.16 (m, 2H, CH, ring).

1.1.1.1 Route B (S)-4-Isopropyl-oxazolidine-2,5-dione (86).

30.4 ml (57.47 mmol, 1.08 eq.) of a 20% solution of phosgene in toluene were added slowly at r.t. to a stirred solution of 6.26 g (53.44 mmol) L-valine (81a) in 63 ml dry THF. After the complete addition the mixture was heated at 55° C. for 4 h. Then a stream of nitrogen was bubbled through the solution and passed after that through a 1M aq. NaOH-solution for 20 min. before the solvent was evaporated. Recrystallization of the obtained residue from PE/Ether (2:1) yielded 3.62 g (25.29 mmol, 47.32%) (S)-4-Isopropyl-oxazolidine-2,5-dione (86) as a white solid.

$^1$H-NMR (500 MHz, CDCl$_3$): δ=1.03 (d, 3H, J=6.78 Hz, CH$_3$), 1.09 (d, 3H, J=6.94 Hz, CH$_3$), 2.24 (m, 1H, CH, i-prop.), 4.19 (m, 1H, CH, ring), 6.80 (s, br., 1H, NH).

6-(S)-Isopropyl-piperazine-2,5-dione (83).

3.10 ml (22.24 mmol, 2.12 eq.) Triethylamine was added to a solution of 1.39 g (11.07 mmol, 1.06 eq.) glycine methylester-hydrochloride in 13 ml chloroform at −78° C. Then a solution of 1.50 g (10.48 mmol) (S)-4-Isopropyl-oxazolidine-2,5-dione (86) in 7.7 ml dry THF was added under stirring. After stirring for another 4 h at −78° C. the mixture was stored for 12 h at −20° C. before it was filtered and the filtrate was evaporated at r.t. The resulting oil was dissolved in 8 ml THF, filtered again and evaporated. The resulting unstable oil was dissolved in 8 ml toluene and refluxed for 24 h. Then the solvent was evaporated and the obtained residue was dissolved in 20 ml water and refluxed with decolorising charcoal for 1 h. After filtration through celite 10 ml EtOH were added and the solvent was evaporated, which led to 338.4 mg (2.17 mmol, 20.68%) 6-(S)-Isopropyl-piperazine-2,5-dione (83) as a white powder.

$^1$H-NMR (400 MHz, D$_2$O): δ=0.56 (d, 3H, J=6.95 Hz, CH$_3$), 0.65 (d, 3H, J=7.07 Hz, CH$_3$), 1.90 (m, 1H, CH, i-prop.), 3.55 (dt, 1H, X-part of a ABX-system, J$_1$=3.66 Hz, J$_{AX}$=J$_{BX}$=1.14 Hz, CH, ring), 3.59 (dd, 1H, B-part of a ABX-system, J$_{AB}$=20.00 Hz, J$_{BX}$=1.14 Hz, CH$_2$, ring), 3.76 (dd, 1H, A-part of a ABX-system, J$_{AB}$=20.00 Hz, J$_{AX}$=1.14 Hz, CH$_2$, ring).

Synthesis of the Benzyl-substituted Piperazine Derivative N-Benzyloxycarbonyl-phenylalanine-glycine-methylester A solution of 7.71 ml (66.82 mmol, 1.05 eq.) 4-methylmorpholine in 13 ml EtOAc was added slowly to a suspension of 20.00 g (66.82 mmol) Z-phenylalanine in 200 ml EtOAc at −15° C., followed by a solution of 6.39 ml (70.08 mmol, 1.00 eq.) ethyl chloroformate in 25 ml EtOAc. The resulting mixture was stirred for 15 min at −15° C. before a solution of 7.71 ml (66.82 mmol, 1.05 eq.) 4-methylmorpholine in 13 ml EtOAc, followed by 8.40 g (66.90 mmol, 1.00 eq.) glycine methylester-hydrochloride were added slowly. After stirring the mixture for another 60 min at −15° C. and 12 h at r.t. 250 ml water and 200 ml EtOAc were added. The aq. layer was extracted with EtOAc and the comb. org. fractions were washed successively with sat. aq. NaHCO$_3$-solution, brine, 2% HCl-solution and brine. After drying the org. fractions over Na$_2$SO$_4$ and evaporation of the solvent 23.30 g (62.91 mmol, 94.14%) N-Benzyloxycarbonyl-phenylalanine-glycine-methylester was obtained as a white solid.

$^1$H-NMR (500 MHz, CDCl$_3$): δ=3.11 (m, 2H, CH$_2$), 3.74 (s, 3H, OCH$_3$), 3.93 (dd, 1H, B-part of a ABX-system, J$_{AB}$=20.00 Hz, J$_{BX}$=6.15 Hz, CH$_2$), 4.04 (dd, 1H, A-part of a ABX-system, J$_{AB}$=20.00 Hz, J$_{BX}$=6.15 Hz, CH$_2$), 4.48 (m, 1H, CH), 5.09 (m, 2H, CH$_2$Ph), 5.28 (d, 1H, J=6.94 Hz, NH), 6.28 (s, br., 1H, NH), 7.14-7.38 (m, 10H, 2*Ph).

6-(S)-Benzyl-piperazine-2,5-dione

A solution of 23.30 g (62.91 mmol) N-Benzyloxycarbonyl-phenylalanine-glycine-methylester (obtained above) in 650 ml dry methanol was hydrogenated by adding Pd/C-catalyst and stirring the resulting mixture under H$_2$ at r.t. for 3 h. After that, the mixture was filtered through celite and then half of the solvent was evaporated. The remaining solution was refluxed for 17 h. Filtration of the white precipitate and washing it twice with methanol yielded 10.71 g (52.45 mmol, 83.37%) 6-(S)-Benzyl-piperazine-2,5-dione as a white solid.

$^1$H-NMR (500 MHz, d$_6$-DMSO): δ=2.76 (d, 1H, J=17.34 Hz), 2.89 (dd, 1H, J$_1$=13.56 Hz, J$_2$=5.04 Hz), 3.09 (dd, 1H, J$_1$=13.56 Hz, J$_2$=4.57 Hz), 3.36 (dd, 1H, J$_1$=17.50 Hz, J$_2$=2.84 Hz), 4.07 (m, 1H), 7.14-7.19 (m, 2H), 7.24-7.32 (m, 3H), 7.89 (s, 1H), 8.15 (s, 1H).

2-(S)-Benzyl-piperazine.

120 ml (120 mmol, 5.93 eq.) of a 1M solution of BH$_3$*THF in THF were added via syringe to a suspension of 4.13 g (20.22 mmol) 6-(S)-Benzyl-piperazine-2,5-dione (XX) in 100 ml dry THF at r.t. After heating the reaction mixture for 4 h under reflux another 130 ml (130 mmol, 6.43 eq.) of a 1M solution of BH3*THF in THF were added via syringe. Then the reaction mixture was refluxed for another 27 h. Then the solution was cooled in ice and treated with 78 ml 30% HBr in HOAc. After stirring the mixture overnight at r.t. the precipitate was collected by filtration and dried under HV. Column chromatography (CH$_2$Cl$_2$/MeOH/NH$_4$OH (16+2+1)) yielded 2.94 g (16.70 mmol, 82.60%) 2-(S)-Benzyl-piperazine as a pale yellow solid.

R$_f$ (CH$_2$Cl$_2$/MeOH/NH$_4$OH (16+2+1))=0.33. $^1$H-NMR (500 MHz, CDCl$_3$): δ=2.47-2.55 (m, 2H), 2.68 (m, 1H), 2.71-2.80 (m, 2H), 2.87 (m, 1H), 2.90 (s, 1H), 2.92 (s, 1H), 2.98 (dd, 1H, J$_1$=11.90 Hz, J$_2$=2.12 Hz), 7.15-7.22 (m, 3H), 7.25-7.30 (m, 2H). MS (EI): m/z=176 (1), 146 (2), 132 (10), 117 (6), 92 (12), 91 (18), 85 (100), 65 (5), 56 (23). HR-MS (EI): Calcd. for C$_{11}$H$_{16}$N$_2$: 176.131348. Found: 176.131736.

3-(S)-Benzyl-piperazine-1-carboxylic acid tert-butyl ester.

6.67 ml (16.68 mmol, 1.00 eq.) of a 2.5 N aq. NaOH-solution were added to a solution of 2.94 g (16.68 mmol) 2-(S)-Benzyl-piperazine in 80 ml tert-Butanol and 80 ml H$_2$O. After cooling to 0° C. 3.64 g (16.68 mmol, 1.00 eq.) Boc-anhydride was added and the mixture was stirred at 0° C. for 2 h. Then the solution was warmed to r.t. and stirred overnight. After evaporating the tert-Butanol the mixture was extracted with CH$_2$Cl$_2$. The comb. org. fractions were dried over Na$_2$SO$_4$ and evaporated. Column chromatography (CH$_2$Cl$_2$/MeOH (10+1)) yielded 3.82 g (13.82 mmol, 82.87%) 3-(S)-Benzyl-piperazine-1-carboxylic acid tert-butyl ester as a clear oil.

R$_f$ (CH$_2$Cl$_2$/MeOH (10+1))=0.45. $^1$H-NMR (500 MHz, CDCl$_3$): δ=1.42 (s, 9H, t-Bu), 2.46-2.66 (m, 3H), 2.71-2.94 (m, 4H), 3.45 (s, 1H), 3.78-4.16 (m, 2H), 7.13-7.7.22 (m, 3H, Ph-H), 7.24-7.30 (m, 2H, Ph-H). MS (EI): m/z=277 (8, M+H), 185 (30), 129 (100), 91 (15), 85 (15), 57 (25). HR-MS (EI): Calcd. for C$_{16}$H$_{25}$N$_2$O$_2$: 277.191603. Found: 277.191137.

Synthesis of the Phenyl Compounds (3-Bromo-phenyl)-phenyl-methanone.

1.65 ml (12.50 mmol) 3-Bromobenzoyl chloride was dissolved in 10 ml of dry benzene. This solution was then added cautiously under stirring to a suspension of 2.00 g (15.00 mmol, 1.20 eq.) aluminum chloride in 20 ml dry benzene at 10° C. After the complete addition the resulting mixture was refluxed for 5 h. After quenching the mixture by adding water and conc. hydrochloric acid the aq. layer was extracted with ethyl acetate. The comb. org. fractions were dried over Na$_2$SO$_4$ and evaporated. Column chromatography (hexanes/ether (9+1)) yielded 3.02 g (11.55 mmol, 92.40%) (3-Bromo-phenyl)-phenyl-methanone as a white solid. R$_f$(hexanes/ether (9+1))=0.40. $^1$H-NMR (500 MHz, CDCl$_3$): δ=7.37 (t, 1H, J=7.88 Hz), 7.51 (m, 2H), 7.62 (tt, 1H, J$_1$=7.41 Hz, J$_2$=1.42 Hz), 7.72 (m, 2H), 7.79 (m, 2H), 7.94 (t, 1H, J=1.80 Hz).

(3-Bromo-phenyl)-phenyl-methanol.

To a solution of 2.39 g (9.15 mmol) (3-Bromo-phenyl)-phenyl-methanone in 100 ml dry methanol 370 mg (9.78 mmol, 1.07 eq.) sodium borohydride was added cautiously at r.t. After stirring this solution for 2 h at r.t. the solvent was evaporated and the residue was taken up in 50 ml water and 50 ml ether. After extracting the aq. layer with ether the comb. org. fractions were washed twice with water, dried over Na$_2$SO$_4$ and evaporated. This yielded 2.24 g (8.52 mmol, 93.16%) (3-Bromo-phenyl)-phenyl-methanol as a white solid.

$^1$H-NMR (500 MHz, CDCl$_3$): δ=2.26 (d, 1H, J=3.47 Hz, OH), 5.79 (d, 1H, J=3.47 Hz, CH), 7.19 (t, 1H, J=7.88 Hz, Ph-H), 7.27-7.31 (m, 2H, Ph-H), 7.34-7.36 (m, 4H, Ph-H), 7.39 (m, 1H, Ph-H), 7.56 (t, 1H, J=1.89 Hz, Ph-H).

1-Benzyl-3-bromo-benzene (87).

To a suspension of 422 mg (11.12 mmol, 1.31 eq.) lithium aluminum hydride in 30 ml dry ether a solution of 1.38 g (10.35 mmol, 1.22 eq.) aluminum chloride in 18 ml dry ether was added cautiously under stirring. After the complete addition the resulting mixture was stirred for 30 min at r.t. before a solution of 2.24 g (8.52 mmol) (3-Bromo-phenyl)-phenyl-methanol (prepared above) in 19 ml dry ether was added dropwise. Then the mixture was refluxed for 12 h and after that cooled to 0° C. in an ice-bath. After adding cautiously 10 ml of a mixture of ether/methanol (1:1) 28 ml 1 N HCl-solution was added and the mixture was extracted with ether. The comb. org. fractions were washed with brine, dried over Na$_2$SO$_4$ and evaporated. Column chromatography (PE/CH$_2$Cl$_2$ (9+1)) yielded 1.50 g (6.06 mmol, 71.17%) 1-Benzyl-3-bromo-benzene (87) as a colorless liquid.

R$_f$ (PE/CH$_2$Cl$_2$ (9+1))=0.43. $^1$H-NMR (500 MHz, CDCl$_3$): δ=3.94 (s, 2H, CH$_2$), 7.08-7.23 (m, 5H, Ph-H), 7.25-34 (m, 4H, Ph-H).

4-Iodo-2-isobutylphenol.

2.43 ml (2.43 mmol, 2.98 eq.) of a 1 M solution of BBr$_3$ in CH$_2$Cl$_2$ was added to a solution of 176.0 mg (0.61 mmol) 4-Iodo-2-isobutylanisole in 25 ml dry CH$_2$Cl$_2$ at 0° C. via syringe. After that the solution was stirred for 3 h at 0° C. and then for 12 h at r.t. The reaction mixture was then added to water and extracted with CH$_2$Cl$_2$. The comb. org. fractions were dried over MgSO$_4$ and evaporated. Column chromatography (hexanes/EtOAc (3+1)) yielded 84.5 mg (0.31 mmol, 50.17%) 4-Iodo-2-isobutylphenol as a colorless oil.

R$_f$ (hexanes/EtOAc (3+1))=0.43. $^1$H-NMR (500 MHz, CDCl$_3$): δ=0.89 (d, 6H, J=6.57 Hz, 2*CH$_3$), 1.87 (m, 1H, CH), 2.38 (d, 2H, J=7.33 Hz, CH$_2$), 4.60 (s, 1H), 6.51 (d, 1H, J=8.21 Hz, 6-Ph-H), 7.30-7.36 (m, 2H, 3-and 5-Ph-H). MS (EI): m/z=277 (10), 276 (85), 234 (24), 233 (100), 107 (11), 106 (11), 78 (22), 77 (10). HR-MS (EI): Calcd. for C$_{10}$H$_{13}$IO: 276.001117. Found: 276.001260.

Carbonic acid tert-butyl ester 4-iodo-2-isobutyl-phenyl ester.

80.2 mg (0.29 mmol) 4-Iodo-2-isobutylphenol, 86.0 mg (0.39 mmol, 1.36 eq.) Boc-anhydride and 6.0 mg (49 μmol, 0.17 eq.) DMAP were dissolved in 8 ml hexanes and stirred at r.t. for 1.5 h. After adding EtOAc, brine and 1 M aq. HCl-solution the organic layer was washed with aq. NaHCO$_3$-solution, dried over Na2SO4 and evaporated. Column chromatography (hexanes/EtOAc (3+1)) yielded 87.9 mg (0.23 mmol, 80.56%) Carbonic acid tert-butyl ester 4-iodo-2-isobutyl-phenyl ester as a colorless oil.

$R_f$ (hexanes/EtOAc (3+1))=0.60. $^1$H-NMR (500 MHz, CDCl$_3$): δ=0.87 (d, 6H, J=6.62 Hz, 2*CH$_3$), 1.51 (s, 9H, t-Bu), 1.83 (m, 1H, CH), 2.35 (d, 2H, J=7.25 Hz, CH$_2$), 6.82 (d, 1H, J=8.04 Hz, 6-Ph-H), 7.46-7.52 (m, 2H, 3-and 5-Ph-H). MS (EI): m/z=376 (12), 361 (13), 276 (38), 233 (16), 57 (100). HR-MS (EI): Calcd. for C$_{15}$H$_{21}$IO$_3$: 376.053547. Found: 376.053399.

(4-Bromo-2-methyl-phenyl)-methanol 12.40 ml (12.40 mmol, 1.31 eq.) of a 1M solution of BH$_3$*THF in THF were added via syringe to a suspension of 2.04 g (9.49 mmol) 4-Bromo-2-methyl-benzoic acid (XX) in 15 ml dry THF at 0° C. After that the resulting mixture was slowly warmed to r.t. over a period of 2 h. Then the mixture was quenched by addition of 2.8 ml of 50% aq. THF, dried with Na$_2$CO$_3$ over 1h and evaporated. The residue was dissolved in H$_2$O and extracted with ether. The comb. org. fractions were washed with H$_2$O, sat. NaHCO$_3$-solution and finally with brine. The comb. aq. fractions were back-extracted with ether and washed with sat. NaHCO$_3$-solution and brine. The comb. org. fractions were dried over Na$_2$SO$_4$ and evaporated, which led after drying under high vacuum to 1.80 g (8.97 mmol, 94.49%) (4-Bromo-2-methyl-phenyl)-methanol in form of a white solid.

$^1$H-NMR (400 MHz, CDCl$_3$): δ=2.28 (s, 3H, CH$_3$), 4.60 (s, 2H, CH$_2$), 7.19 (m, 1H, Ph-H), 7.29 (m, 2H, Ph-H). MS (EI): m/z=202 (77), 201 (15), 200 (77), 199 (13), 187 (24), 185 (47), 184 (95), 183 (24), 182 (100), 173 (10), 171 (17), 121 (59), 104 (18), 103 (45), 93 (75), 92 (59), 91 (84), 90 (20), 89 (21), 78 (33), 77 (85), 65 (23), 63 (34). HR-MS (EI): Calcd. for C$_8$H$_9$BrO: 199.983676. Found: 199.984267.

Coupling Reactions 4-(3'-Benzylphenyl)-3-(S)-isopropyl-piperazine-1-carboxylic acid tert-butyl ester (88).

Route A:

17.9 mg (19.55 μmol, 0.044 eq.) Pd$_2$(dba)$_3$ and 5.9 mg (19.38 μmol, 0.044 eq.) P(o-tolyl)$_3$ were dissolved in 6 ml dry toluene. Then 58.9 mg (610 μmol, 1.39 eq.) NaOt-Bu was added, followed by a solution of 101 mg (442 μmol) 3-(S)-Isopropyl-piperazine-1-carboxylic acid tert-butyl ester (85) and 110 mg (445 μmol, 1.01 eq.) 1-Benzyl-3-bromo-benzene (87). The resulting mixture was heated at 100° C. for 19 h. After filtrating the reaction mixture through celite the solvent was evaporated. Column chromatography (hexanes/EtOAc (3+1)) yielded 39.6 mg (100 μmol, 22.71%) 4-(3'-Benzylphenyl)-3-(S)-iso-propyl-piperazine-1-carboxylic acid tert-butyl ester (88).

$R_f$ (hexanes/EtOAc (3+1))=0.55. $^1$H-NMR (500 MHz, CDCl$_3$): δ=0.79 (d, 3H, J=6.78 Hz, CH$_3$), 0.99 (d, 3H, J=6.62 Hz, CH$_3$), 1.47 (s, 9H, Ot-Bu), 2.11 (m, 1H, CH in iso-propyl), 2.96-3.14 (m, 2H, ring-CH$_2$), 3.20 (m, 1H, ring-CH), 3.29-3.48 (m, 2H, ring-CH$_2$), 3.92 (s, 2H, Ph-CH$_2$), 3.96-4.06 (m, 2H, ring-CH$_2$), 6.56 (m, 1H, Ph-H), 6.64 (m, 1H, Ph-H), 7.13 (t, 1H, J=7.88 Hz, Ph-H), 7.17-7.23 (m, 3H, Ph-H), 7.29 (m, 2H, Ph-H). MS (EI): m/z =394 (6), 351 (15), 296 (15), 295 (72), 272 (16), 195 (16), 169 (14), 168 (99), 167 (100), 166 (17), 165 (41), 153 (17), 152 (22), 105 (18), 91 (26), 86 (43), 84 (63), 77 (11), 57 (14). HR-MS (EI): Calcd. for C$_{25}$H$_{34}$N$_2$O$_2$: 394.26203. Found: 394.262138.

Route B:

9.4 mg (10.3 μmol, 0.013 eq.) Pd$_2$(dba)$_3$ and 11.4 mg (29.9 μmol, 0.04 eq.) 2-Diphenylphosphino-2'-dimethy-lamino-biphenyl were dissolved in 6 ml dry toluene. Then 170.7 mg (1.78 mmol, 2.32 eq.) NaOt-Bu was added, followed by a solution of 175.0 mg (0.77 mmol) 3-(S)-Isopropyl-piperazine-1-carboxylic acid tert-butyl ester (85) and 290.6 mg (1.18 μmol, 1.54 eq.) 1-Benzyl-3-bromo-benzene (87). The resulting mixture was heated at 80° C. for 22 h. After cooling to room temperature the mixture was diluted with ether and washed with brine. The comb. org. fractions were dried over Na$_2$SO$_4$ and evaporated. Column chromatography (hexanes/EtOAc (3+1)) yielded 276.5 mg (0.70 mmol, 91.49%) 4-(3'-Benzylphenyl)-3-(S)-iso-propyl-piperazine-1-carboxylic acid tert-butyl ester (88).

$R_f$ (hexanes/EtOAc (3+1))=0.55. $^1$H-NMR (500 MHz, CDCl$_3$): δ=0.76 (d, 3H, J=6.62 Hz, CH$_3$), 0.96 (d, 3H, J=6.46 Hz, CH$_3$), 1.45 (s, 9H, Ot-Bu), 2.09 (m, 1H, CH in iso-propyl), 2.92-3.12 (m, 2H, ring-CH$_2$), 3.16 (m, 1H, ring-CH), 3.25-3.44 (m, 2H, ring-CH$_2$), 3.90 (s, 2H, Ph-CH$_2$), 3.92-4.04 (m, 2H, ring-CH$_2$), 6.54 (m, 1H, Ph-H), 6.59-6.66 (m, 2H, Ph-H), 7.10 (t, 1H, J=8.04 Hz, Ph-H), 7.14-7.18 (m, 3H, Ph-H), 7.25 (m, 2H, Ph-H).

4-(3'-Benzylphenyl)-3-(S)-isopropyl-piperazine (88a).

275.6 mg (0.70 mmol) 4-(3'-Benzylphenyl)-3-(S)-iso-propyl-piperazine-1-carboxylic acid tert-butyl ester (88) were dissolved in 8 ml dry CH$_2$Cl$_2$ and treated with 8 ml TFA, 0.42 ml H$_2$O and 0.42 ml Et$_3$SiH. The resulting mixture was then stirred at r.t. for 3.5 h before it was poured slowly into sat. aq. NaHCO$_3$-solution. After adding 10% NaOH-solution to the mixture until it became alkaline the solution was extracted with CH$_2$Cl$_2$. The comb. org. fractions were dried over Na$_2$SO$_4$ and evaporated. Column chromatography (CH$_2$Cl$_2$/MeOH (4+1)) yielded 191.1 mg (0.65 mmol, 92.92%) 4-(3'-Benzylphenyl)-3-(S)-isopropyl-piperazine (88a) as an oil.

$R_f$ (CH$_2$Cl$_2$/MeOH (4+1))=0.64. $^1$H-NMR (500 MHz, CDCl$_3$): δ=0.78 (d, 3H, J=6.78 Hz, CH$_3$), 0.90 (d, 3H, J=6.62 Hz, CH$_3$), 2.31 (m, 1H, CH in iso-propyl), 2.73 (s, br., 1H), 2.89-2.95 (m, 3H), 3.01 (dd, 1H, J$_1$=12.45 Hz, J$_2$=3.54 Hz, ring-CH), 3.16 (m, 1H), 3.23 (m, 1H), 3.32 (m, 1H), 3.90 (s, 2H, CH$_2$Ph), 6.56 (m, 1H, Ph-H), 6.65-6.70 (m, 2H, Ph-H), 7.11 (t, 1H, J=7.71 Hz, Ph-H), 7.14-7.19 (m, 3H, Ph-H), 7.25 (m, 2H, Ph-H). MS (EI): m/z=294 (7), 252 (21), 251 (100), 222 (5), 196 (10), 165 (7), 91 (10), 56 (11). HR-MS (EI): Calcd. for C$_{20}$H$_{26}$N$_2$: 294.209598. Found: 294.210197.

1-(3-Benzyl-phenyl)-2-(S)-isopropyl-4-(2-isopropyl-phenyl)-piperazine (89).

110.7 mg (0.38 mmol) 4-(3'-Benzylphenyl)-3-(S)-isopropyl-piperazine (88a), 123.5 mg (0.62 mmol, 1.65 eq.) 1-Bromo-2-isopropyl-benzene 11.7 mg (12.7 μmol, 0.034 eq.) Pd$_2$(dba)$_3$, 7.4 mg (19.3 μmol, 0.05 eq.) 2-Diphenylphosphino-2'-dimethylamino-biphenyl and 87.3 mg (0.91 mmol, 2.42 eq.) NaOt-Bu were dissolved in 5 ml dry toluene. The resulting mixture was heated under N$_2$ at 80° C. for 15.5 h. After cooling to room temperature the mixture was diluted with ether and washed with brine. The comb. org. fractions were dried over Na$_2$SO$_4$ and evaporated. Column chromatography (hexanes/EtOAc (9+1)) yielded 96.5 mg (0.23 mmol, 62.20%) 1-(3-Benzyl-phenyl)-2-(S)-isopropyl-4-(2-isopropyl-phenyl)-piperazine (89) as a clear oil.

$R_f$ (hexanes/EtOAc (9+1))=0.44. $^1$H-NMR (500 MHz, CDCl$_3$): δ=0.80 (d, 3H, J=6.94 Hz, CH$_3$), 0.89 (d, 3H, J=6.78 Hz, CH$_3$), 1.17 (d, 3H, J=6.94 Hz, CH$_3$), 1.21 (d, 3H, J=6.94 Hz, CH$_3$), 2.66 (m, 1H, CH, i-prop), 2.76-2.90 (m, 2H), 2.93-3.02 (m, 2H), 3.34 (m, 1H, CH, i-prop), 3.36-3.52 (m, 2H), 3.61 (m, 1H), 3.91 (s, 2H, CH$_2$Ph), 6.54 (m, 1H, Ph-H), 6.71 (m, 2H, Ph-H), 7.05-7.20 (m, 7H), 7.24-7.28 (m, 3H, Ph-H). MS (EI): m/z=412 (6, M+), 370 (34), 369 (100), 222 (14), 195 (11), 132 (10), 91 (11). HR-MS (EI): Calcd. for $C_{29}H_{36}N_2$: 412.287848. Found: 412.288287.

Figure 19:
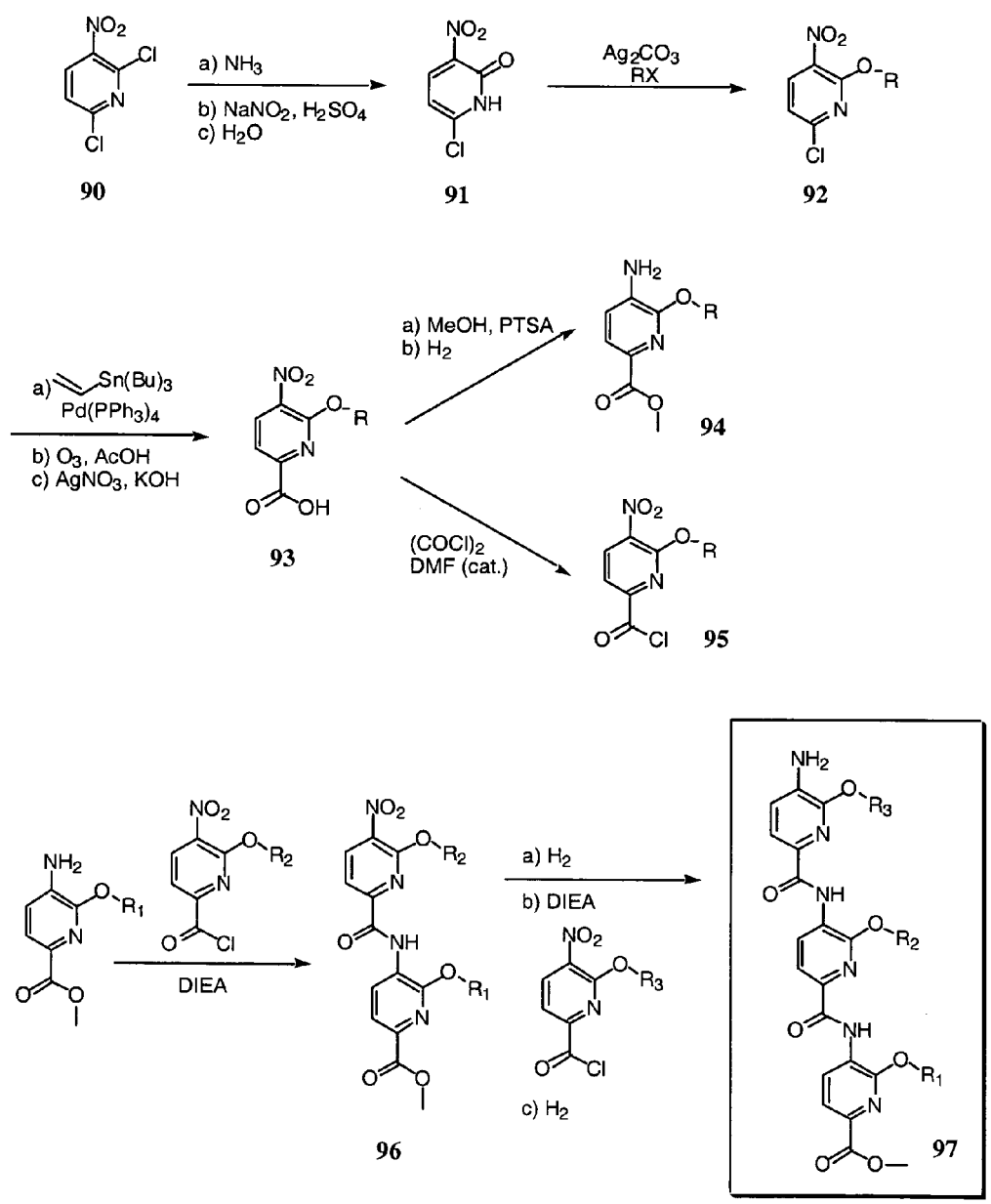
FIG. 19, Scheme 19, represents a synthetic route to alternative terpyridyl derivatives of the present invention.

General Procedure for the Preparation of Terpyridyl Proteomimetics According to FIG. 19, Scheme 19

Nicotinoyl chloride hydrochloride (0.3 g, 1.685 mmol), DIEA (0.65 g, 5.06 mmol, 3.0 eqv), and ortho- or meta-anisidine (0.21 g, 1.68 mmol, 1 eqv) were dissolved in CH2Cl2 and stirred at rt for 48 h. The solution was extracted with 1N HCl solution. The aqueous layer was neutralized with a NaHCO₃ solution and extracted with CH2Cl2. The organic extracts were combined, dried (MgSO4), filtered, and concentrated in vacuo to give a white solid.

N-(3-methoxyphenyl)nicotinamide; 88% yield.

$^1$H NMR (400 MHz, CDCl3) d 3.84 (s, 3H), 6.74 (d, J=8.4 Hz, 1H), 7.13 (d, J=8.0 Hz, 1H), 7.27 (t, J=8.4 Hz, 1H), 7.42 (s, 1H), 7.46 (dd, J1=8.4 Hz, J2=7.2 Hz, 1H), 8.03 (s, 1H), 8.24 (d, J=8.0 Hz, 1H), 8.78 (d, J=4.8 Hz, 1H), 9.13 (s, 1H); $^{13}$C NMR (125 MHz, CDCl$_3$) d 55.31, 106.23, 110.85, 112.61, 123.77, 129.79, 130.95, 135.74, 138.72, 147.62, 151.99, 160.18, 163.79; HRMS (EI) Calcd for C13H12N2O2: 228.0899. Found 228.0901.

N-(2-methoxyphenyl)nicotinamide; 75% yield.

1H NMR (400 MHz, CDCl3) d 3.93 (s, 3H), 6.93 (d, J=8.0 Hz, 1H), 7.02 (t, J=8.0 Hz, 1H), 7.11 (t, J=7.2 Hz, 1H), 7.44 (dd, J1=8.0 Hz, J2=6.8 Hz, 1H), 8.22 (d, J=8.0 Hz, 1H), 8.49 (d, J=8.0 Hz, 1H), 8.55 (s, 1H), 8.77 (d, J=5.2 Hz, 1H), 9.12 (s, 1H); 13C NMR (125 MHz, CDCl3) d 55.80, 109.96, 119.93, 121.18, 123.64, 124.36, 127.25, 130.97, 135.19, 147.88, 148.12, 152.38, 163.21; HRMS (EI) Calcd for C13H12N2O2: 228.0899. Found 228.0902.

Picolinic acid (1.0 g, 8.12 mmol) and (COCl)2 (3.0 g, 24.0 mmol, 3 eqv) were dissolved in CH2Cl2 and allowed to stir at rt for 2 h. The solvent was evaporated to yield the crude acid chloride. Ortho- or meta-anisidine (1.0 g, 8.12 mmol, 1.0 eqv) and DIEA (2.1 g, 16.24 mmol, 2.0 eqv) were dissolved in CH2Cl2 and added to the acid chloride. The solution was stirred at rt for 12 h. The solvent was concentrated in vacuo. Column chromatography [Hexanes/EtOAc (1/1)] yielded a white solid.

N-(3-methoxyphenyl)-2-pyridinecarboxamide; 83% yield.

1H NMR (400 MHz, CDCl3) d 3.85 (s, 3H), 6.71 (d, J=9.2 Hz, 1H), 7.28 (m, 2H), 7.48 (t, J=7.6 Hz, 1H), 7.58 (s, 1H), 7.91 (t, J=7.6 Hz, 1H), 8.30 (d, J=8.8 Hz, 1H), 8.62 (d, J=4.8 Hz, 1H), 10.03 (s, 1H); 13C NMR (125 MHz, CDCl3) d 55.33, 105.12, 110.48, 111.92, 122.38, 126.45, 129.72, 137.70, 138.93, 147.94, 149.77, 160.25, 161.96; HRMS (EI) Calcd for C13H12N2O2: 228.0899. Found 228.0899.

N-(2-methoxyphenyl)-2-pyridinecarboxamide; 89% yield.

1H NMR (400 MHz, CDCl3) d 3.98 (s, 3H), 6.94 (d, J=6.8 Hz, 1H), 7.03 (t, J=7.6 Hz, 1H), 7.10 (t, J=7.6 Hz, 1H), 7.47 (t, J=5.6 Hz, 1H), 7.90 (t, J=7.6 Hz, 1H), 8.30 (d, J=7.6 Hz, 1H), 8.62 (d, J=8.0 Hz, 1H), 8.66 (d, J=7.6 Hz, 1H), 10.58 (s, 1H); 13C NMR (125 MHz, CDCl3) d 55.82, 110.06, 119.72, 121.03, 122.31, 123.94, 126.19, 127.50, 137.46, 148.15, 148.76, 150.33, 161.98; HRMS (EI) Calcd for $C_{13}H_{12}N_2O_2$: 228.0899. Found 228.0894.

6-Chloro-3-nitro-2-pyridinamine (90a); 89% yield.

2,6-Dichloro-3-nitropyridine 90 (10.0 g, 51.8 mmol) was dissolved in 37 ml of a 7N solution of $NH_3$ in EtOH (0.26 mol, 5.0 eqv) and the solution was stirred at rt for 24 h. H2O (40 ml) was added and the resulting mixture was filtered to collect the crude yellow product. The solid material was dissolved in $CH_2Cl_2$ and then extracted with a 1N HCl solution. The aqueous extracts were combined and then neutralized with NaHCO₃ before being re-extracted with $CH_2Cl_2$. The organic fractions were combined, dried ($MgSO_4$), filtered, and concentrated in vacuo to yield 8.0 g of a yellow solid (89%): $^1$H NMR (400 MHz, d$_6$-DMSO) d 6.77 (d, J=8.8 Hz, 1H), 8.27 (s, 2H), 8.39 (d, J=8.4 Hz, 1H); $^{13}$C NMR (125 MHz, d$_6$-DMSO) d 111.89, 126.02, 138.28, 153.36, 154.88; HRMS (EI) Calcd for $C_5H_4ClN_3O_2$: 172.9997. Found 172.9996.

6-chloro-3-nitro-2(1H)-pyridone (91).

6-Chloro-3-nitro-2-pyridinamine (90a) (0.3 g, 1.73 mmol) was dissolved in 5 ml of conc. $H_2SO_4$ at 0ø C. A solution of NaNO₂ (0.24 g, 3.46 mmol, 2.0 eqv) in 2 ml of $H_2O$ was added cautiously to the arylamine solution and the mixture was stirred at 0ø C. for 30 min. $H_2O$ (10 ml) was added and the solid precipitate was filtered and washed with cold $H_2O$ several times. The solid was dried under vacuum to give 0.2 g of a yellow solid (67%): $^1$H NMR (400 MHz, d6-DMSO) d 7.08 (d, J=6.4 Hz, 1H), 8.43 (d, J=6.8 Hz, 1H); 13C NMR (125 MHz, d6-DMSO) d 113.93, 132.10, 138.90, 150.27, 156.47; HRMS (EI) Calcd for C5H3C₁N2O3: 173.9832. Found 173.9830.

General Procedure for Alkylation of 6-chloro-3-nitro-2(1H)-pyridone to Yield Derivatives of Structure 92.

6-chloro-3-nitro-2(1H)-pyridone (6-7) (1.34 g, 7.67 mmol), Ag2CO3 (1.27 g, 4.61 mmol), and desired electrophile (7.67 mmol, 1.0 eqv) were added to 25 ml of toluene. The mixture was stirred at 85ø C. for 18 h and then cooled to rt. The silver salts were filtered off. The filtrate was washed with a NaHCO3 solution and then H2O before being concentrated in vacuo. Column chromatography [Hexanes/EtOAc (5/1)] yielded the alkylated product as yellow/white solid.

6-Chloro-2-methoxy-3-nitropyridine (92a); 86% yield.

$^1$H NMR (400 MHz, CDC$^{13}$) d 4.14 (s, 3H), 7.05 (d, J=8.4 Hz, 1H), 8.28 (d, J=8.4 Hz, 1H); 13C NMR (125 MHz, CDCl3) d 55.62, 116.63, 132.36, 137.52, 152.99, 156.33; HRMS (EI) Calcd for C6H5ClN2O3: 187.9983. Found 187.9983.

6-Chloro-2-isopropoxy-3-nitropyridine (92b); 81% yield.

$^1$H NMR (400 MHz, CDCl3) d 1.43 (d, J=6.0 Hz, 6H), 5.50 (m, 1H), 6.97 (d, J=8.0 Hz, 1H), 8.21 (d, J=8.4 Hz, 1H); 13C NMR (125 MHz, CDCl3) d 21.71, 72.49, 115.87, 132.68, 137.32, 152.73, 155.73; HRMS (EI) Calcd for C8H9ClN2O3: 216.0302. Found 216.0298.

2-(Benzyloxy)-6-chloro-3-nitropyridine (92c); 47% yield.

$^1$H NMR (400 MHz, CDCl3) d 5.57 (s, 2H), 7.04 (d, J=8.0 Hz, 1H), 7.35 (m, 3H), 7.52 (d, J=8.0 Hz, 2H), 8.27 (d, J=8.0 Hz, 1H); 13C NMR (125 MHz, CDCl3) d 69.67, 116.72, 127.75, 128.14, 128.41, 132.26, 135.05, 137.51, 152.62, 155.45; HRMS (FAB) Calcd for C12H10ClN2O3: 265.0379. Found 265.0379.

General Procedure for Conversion of Aryl Chlorides (92) to Aryl Carboxylic Acids (93).

The aryl chloride (92) (4.2 mmol), vinyltributyltin (4.6 mmol, 1.1 eqv), and Pd(PPh3)4 (5 mol %) were dissolved in toluene and refluxed for 18 h. The solvent was removed in vacuo, H₂O was added, and the mixture was extracted with $CH_2Cl_2$. The organic fractions were combined, dried (MgSO4), filtered, and concentrated in vacuo to give the crude olefin as a dark oil. The olefin was dissolved in 20 ml of $CH_2Cl_2$ and 0.5 ml of AcOH at −78ø C. Ozone was bubbled through the solution for 1 h or until the solution turned blue. The solution was neutralized with NaHCO$_3$ (aq) before being extracted with CH$_2$Cl$_2$. The organic fractions were combined, dried (MgSO4), filtered, and concentrated in vacuo to give the crude aldehyde as a yellow solid/oil. The crude material was dissolved in 40 ml of EtOH. To this solution was added AgNO3 (10.4 mmol, 2.5 eqv) in 7.0 ml of H2O. A solution of NaOH (83.8 mmol, 20.0 eqv) in 60.0 ml of H2O was added dropwise over 1 h. The resulting mixture was allowed to stir for 2 h at rt before being filtered. The filtrate was extracted with CH2Cl2 and the organic fractions were discarded. The aqueous layer was acidified to pH 3.0 using 1N HCl and re-extracted with CH2Cl2. The organic fractions were combined, dried (MgSO4), filtered, and concentrated in vacuo to give the aryl carboxylic acid as a white solid.

6-Methoxy-5-nitro-2-pyridinecarboxylic acid (93a); 76% yield.

1H NMR (400 MHz, CDCl3) d 4.22 (s, 3H), 7.97 (d, J=8.0 Hz, 1H), 8.43 (d, J=8.0 Hz, 1H); 13C NMR (125 MHz, CDCl3) d 55.52, 117.34, 136.98, 137.28, 146.47, 155.84, 162.08; HRMS (EI) Calcd for C7H6N2O5: 198.0277. Found 198.0282.

6-Isopropoxy-5-nitro-2-pyridinecarboxylic acid (93b); 76% yield.

1H NMR (400 MHz, CDCl3) d 1.48 (d, J=6.0 Hz, 6H), 5.50 (m, 1H), 7.91 (d, J=8.0 Hz, 1H), 8.36 (d, J=8.0 Hz, 1H); 13C NMR (125 MHz, CDCl3) d 21.69, 72.69, 116.64, 136.61, 137.68, 146.29, 155.06, 162.54; HRMS (EI) Calcd for C9H10N2O5: 227.0668. Found 227.0668.

6-(Benzyloxy)-5-nitro-2-pyridinecarboxylic acid (93c); 70% yield.

1H NMR (400 MHz, CDCl3) d 5.62 (s, 2H), 7.39 (m, 3H), 7.49 (m, 2H), 7.92 (d, J=8.0 Hz, 1H), 8.37 (d, J=8.0 Hz, 1H); 13C NMR (125 MHz, CDCl3) d 69.90, 118.00, 127.69, 128.48, 128.70, 134.99, 136.56, 136.98, 146.84, 155.18, 164.62; HRMS (FAB) Calcd for C13H11N2O5: 275.0668. Found 275.0668.

General Procedure for the Synthesis of Methyl Esters (93e).

The aryl carboxylic acid (93) (2.22 mmol), and a catalytic amount of p-toluenesulfonic acid (50 mg) were dissolved in 10 ml of anhydrous MeOH. The solution was stirred at 55ø C. for 48 h. The reaction mixture was cooled to rt and concentrated in vacuo. Column chromatography [Hexanes/EtOAc (2/1)] yielded the methyl ester as a white solid.

Methyl 6-methoxy-5-nitro-2-pyridinecarboxylate (93e1); 87% yield.

1H NMR (400 MHz, CDCl3) d 4.00 (s, 3H), 4.19 (s, 3H), 7.80 (d, J=8.0 Hz, 1H); 8.32 (d, J=8.0 Hz, 1H); 13C NMR (125 MHz, CDCl3) d 53.20, 55.22, 117.97, 135.69, 136.14, 148.71, 156.07, 163.76; HRMS (EI) Calcd for C8H8N2O5: 212.0433. Found 212.0431.

Methyl 6-isopropoxy-5-nitro-2-pyridinecarboxylate (93e2); 92% yield.

1H NMR (400 MHz, CDCl3) d 1.43 (d, J=6.4 Hz, 6H), 3.99 (s, 3H), 5.63 (m, 1H), 7.73 (d, J=8.0 Hz, 1H), 8.24 (d, J=8.0 Hz, 1H); 13C NMR (125 MHz, CDCl3) d 21.73, 53.09, 71.82, 117.22,135.33, 136.47, 148.54, 155.39, 163.96; HRMS (EI) Calcd for $C_{10}H_{12}N_2O_5$: 241.0824. Found 241.0823.

Methyl 6-(benzyloxy)-5-nitro-2-pyridinecarboxylate (93e3); 89% yield.

1H NMR (400 MHz, CDCl3) d 4.01 (s, 3H), 5.65 (s, 2H), 7.37 (m, 3H), 7.55 (d, J=7.2 Hz, 2H), 7.79 (d, J=8.0 Hz, 1H), 8.30 (d, J=8.0 Hz, 1H); 13C NMR (125 MHz, CDCl3) d 53.15, 69.38, 118.09, 128.22, 128.24, 128.44, 135.44, 135.77, 136.10, 148.45, 155.33, 163.65; HRMS (EI) Calcd for C14H12N2O5: 287.0668. Found 287.0666.

General Procedure for the Reduction of Arylnitro Derivatives 93e, 96, and 96b to Yield Aryl Amines 94a-c, 95a-d, and 97a-f.

The arylnitro compound (1.2 mmol) and 10% Pd/C (50 mg) were added to 12 ml of MeOH. (PtO2 and THF solvent were used with compounds possessing a benzyloxy side chain.) The mixture was stirred at rt for 10 h under 1 atm of H2. The reaction mixture was filtered through celite and then concentrated. Column chromatography [Hexanes/EtOAc (3/1)] yielded the arylamine as a white solid.

Methyl 5-amino-6-methoxy-2-pyridinecarboxylate (94a); 81% yield.

1H NMR (400 MHz, CDCl3) d 3.91 (s, 3H), 4.08 (s, 3H), 4.23 (s, 2H), 6.85 (d, J=8.0 Hz, 1H), 7.65 (d, J=8.8 Hz, 1H); 13C NMR (125 MHz, CDCl3) d 52.14, 53.58, 117.88, 121.25, 132.92, 135.09, 151.62, 165.92; HRMS (EI) Calcd for C8H10N2O3: 182.0691. Found 182.0691.

Methyl 5-amino-6-isopropoxy-2-pyridinecarboxylate (94b); 91% yield.

1H NMR (400 MHz, CDCl3) d 1.37 (d, J=4.4 Hz, 6H), 3.89 (s, 3H), 5.52 (m, 1H), 6.86 (d, J=6.0 Hz, 1H), 7.61 (d, J=6.4 Hz, 1H); 13C NMR (125 MHz, CDCl3) d 22.13, 52.03, 68.65, 117.98, 120.63, 133.10, 135.08, 150.85, 166.04; HRMS (EI) Calcd for C10H14N2O3: 211.1083. Found 211.1084.

Methyl 5-amino-6-(benzyloxy)-2-pyridinecarboxylate (94c); 63% yield.

1H NMR (400 MHz, CDCl3) d 3.91 (s, 3H), 4.36 (s, 2H), 5.48 (s, 2H), 6.84 (d, J=8.0 Hz, 1H), 7.36 (m, 3H), 7.47 (d, J=8.0 Hz, 1H), 7.65 (d, J=7.6 Hz, 1H); 13C NMR (125 MHz, CDCl3) d 52.04, 67.90, 117.90, 121.42, 127.93, 128.33, 128.42, 132.33, 135.21, 136.86, 150.86, 165.85; HRMS (EI) Calcd for C14H14N2O3: 258.1004. Found 258.1003.

Methyl 5-{[(5-amino-6-methoxy-2-pyridinyl)carbonyl]amino}-6-methoxy-2-pyridinecarboxylate (96a); 100% yield.

1H NMR (400 MHz, CDCl3) d 3.95 (s, 3H), 4.12 (s, 3H), 4.16 (s, 3H), 4.18 (s, 2H), 6.96 (d, J=7.2 Hz, 1H), 7.75 (d, J=7.6 Hz, 1H), 7.82 (d, J=8.0 Hz, 1H), 8.87 (d, J=8.4 Hz, 1H), 10.39 (s, 1H); 13C NMR (125 MHz, CDCl3) d 52.41, 53.33, 54.25, 118.16, 119.05, 120.66, 124.58, 126.94, 134.65, 135.04, 137.45, 150.58, 152.81, 163.45, 165.48; HRMS (EI) Calcd for C15H16N4O5: 332.1120. Found 332.1119.

Methyl 5-{[(5-amino-6-isopropoxy-2-pyridinyl)carbonyl]amino}-6-isopropoxy-2-pyridinecarboxylate (96b); 87% yield.

1H NMR (400 MHz, CDCl3) d 1.43 (d, J=6.0 Hz, 6H), 1.46 (d, J=6.4 Hz, 6H), 3.93 (s, 3H), 4.26 (s, 2H), 5.54 (m, 1H), 5.65 (m, 1H), 6.95 (d, J=7.6 Hz, 1H), 7.73 (d, J=7.6 Hz, 1H), 7.77 (d, J=8.0 Hz, 1H), 8.90 (d, J=8.0 Hz, 1H), 10.25 (s, 1H); 13C NMR (125 MHz, CDCl3) d 22.13, 22.16, 52.30, 68.57, 69.26, 117.72, 118.99, 120.04, 124.68, 127.03, 134.66, 135.25, 137.44, 149.69, 151.91, 163.61, 165.58; HRMS (EI) Calcd for C19H24N4O5: 389.1825. Found 389.1825.

Methyl 5-{[(5-amino-6-(benzyloxy)-2-pyridinyl)carbonyl]amino}-6-(benzyloxy)-2-pyridinecarboxylate (96c); 76% yield.

1H NMR (400 MHz, CDCl3) d 3.96 (s, 3H), 4.28 (s, 2H), 4.97 (s, 2H), 5.55 (s, 2H), 6.91 (d, J=7.6 Hz, 1H), 7.03 (t, J=7.6 Hz, 1H), 7.13 (t, J=7.2 Hz, 2H), 7.25 (m, 2H), 7.33 (m,

3H), 7.43 (d, J=7.2 Hz, 2H), 7.74 (d, J=7.6 Hz, 1H), 7.85 (d, J=8.0 Hz, 1H), 8.95 (d, J=8.4 Hz, 1H), 10.27 (s, 1H); 13C NMR (125 MHz, CDCl3) d 52.40, 67.72, 68.89, 118.36, 118.91, 120.72, 124.93, 126.83, 128.14, 128.26, 128.29, 128.30, 128.41, 128.71, 134.14, 135.18, 136.10, 136.39, 137.25, 149.78, 152.25, 163.46, 165.38; HRMS (FAB) Calcd for C27H25N4O5: 485.1825. Found 485.1826.

Methyl 5-{[(5-amino-6-(benzyloxy)-2-pyridinyl)carbonyl]amino}-6-isopropoxy-2-pyridinecarboxylate (96d); 76% yield.

1H NMR (400 MHz, CDCl3) d 1.38 (d, J=6.4 Hz, 6H), 3.92 (s, 3H), 4.39 (s, 2H), 5.53 (s, 2H), 5.58 (m, 1H), 6.97 (d, J=7.6 Hz, 1H), 7.41 (m, 3H), 7.50 (d, J=8.0 Hz, 2H), 7.77 (d, J=8.0 Hz, 1H), 8.89 (d, J=8.0 Hz, 1H), 10.38 (s, 1H); 13C NMR (125 MHz, CDCl3) d 22.12, 52.27, 67.97, 69.42, 118.33, 119.07, 119.99, 124.36, 126.92, 128.32, 128.34, 128.60, 134.21, 135.14, 136.24, 137.31, 149.81, 151.82, 163.31, 165.51; HRMS (FAB) Calcd for C23H25N4O5: 437.1825. Found 437.1824.

Methyl 5-{[(5-{[(5-amino-6-methoxy-2-pyridinyl)carbonyl]amino}-6-methoxy-2-pyridinyl)carbonyl]amino}-6-methoxy-2-pyridinecarboxylate (97a); 96% yield.

1H NMR (500 MHz, CD2Cl2) d 3.89 (s, 3H), 4.12 (s, 3H), 4.13 (s, 3H), 4.19 (s, 3H), 4.33 (s, 2H), 8.96 (d, J=8.0 Hz, 1H), 7.69 (d, J=7.5 Hz, 1H), 7.77 (d, J=8.0 Hz, 1H), 7.88 (d, J=8.0 Hz, 1H), 8.84 (d, J=8.0 Hz, 1H), 8.93 (d, J=8.0 Hz, 1H), 10.34 (s, 1H), 10.40 (s, 1H); 13C NMR (125 MHz, CD2Cl2) d 52.54, 53.72, 54.40, 54.50, 117.72, 118.36, 119.19, 120.73, 124.94, 125.65, 127.03, 127.53, 134.77, 135.78, 138.29, 139.19, 151.03, 152.33, 153.30, 163.02, 163.54, 165.53; HRMS (FAB) Submitted.

Methyl 5-{[(5-{[(5-amino-6-isopropoxy-2-pyridinyl)carbonyl]amino}-6-isopropoxy-2-pyridinyl)carbonyl]amino}-6-isopropoxy-2-pyridinecarboxylate (97b); 99% yield.

1H NMR (400 MHz, CDCl3) d 1.45 (d, J=6.0 Hz, 6H), 1.49 (d, J=6.4 Hz, 6H), 1.53 (d, J=6.4 Hz, 6H), 3.94 (s, 3H), 5.55 (m, 1H), 5.67 (m, 1H), 6.98 (d, J=8.0 Hz, 1H), 7.75 (d, J=8.0 Hz, 1H), 7.79 (d, J=8.0 Hz, 1H), 7.93 (d, J=8.4 Hz, 1H), 8.93 (d, J=8.4 Hz, 1H), 9.02 (d, J=8.4 Hz, 1H), 10.25 (s, 1H), 10.30 (s, 1H); 13C NMR (125 MHz, CDCl3) d 22.18, 22.18, 22.18, 52.36, 68.58, 69.24, 69.36, 117.35, 117.86, 119.06, 120.04, 125.02, 125.84, 126.70, 127.18, 134.60, 135.29, 137.85, 138.86, 149.68, 150.85, 151.96, 162.94, 163.50, 165.51; HRMS (EI) Calcd for C28H34N6O7: 566.2489. Found 566.2489.

Methyl 5-{[(5-{[(5-amino-6-(benzyloxy)-2-pyridinyl)carbonyl]amino}-6-(benzyloxy)-2-pyridinyl)carbonyl]amino}-6-(benzyloxy)-2-pyridinecarboxylate (97c); 61% yield.

1H NMR (400 MHz, d6-DMSO) d 3.90 (s, 3H), 5.16 (s, 2H), 5.31 (s, 2H), 5.57 (s, 2H), 5.64 (s, 2H), 7.04 (d, J=7.6 Hz, 1H), 7.14 (m, 5H), 7.34 (m, 8H), 7.49 (d, J=6.8 Hz, 2H), 7.62 (d, J=7.6 Hz, 1H), 7.82 (d, J=8.0 Hz, 1H), 7.89 (d, J=8.0 Hz, 1H), 8.83 (d, J=8.0 Hz, 1H), 8.90 (d, J=8.4 Hz, 1H), 10.09 (s, 1H), 10.22 (s, 1H); HRMS (FAB) Calcd for C40H35N6O7: 711.2567. Found 711.2569.

Methyl 5-{[(5-{[(5-amino-6-isopropoxy-2-pyridinyl)carbonyl]amino}-6-(benzyloxy)-2-pyridinyl)carbonyl]amino}-6-isopropoxy-2-pyridinecarboxylate (97d); 66% yield.

1H NMR (400 MHz, CDCl3) d 1.11 (d, J=5.6 Hz, 6H), 1.36 (d, J=6.0 Hz, 6H), 3.93 (s, 3H), 4.19 (s, 2H), 4.91 (m, 1H), 5.60 (m, 1H), 5.64 (s, 2H), 6.91 (d, J=8.0 Hz, 1H), 7.42 (m, 5H), 7.72 (d, J=8.0 Hz, 1H), 7.79 (d, J=8.0 Hz, 1H), 7.99 (d, J=8.0 Hz, 1H), 8.91 (d, J=8.4 Hz, 1H), 9.10 (d, J=8.4 Hz, 1H), 10.18 (s, 1H), 10.43 (s, 1H); 13C NMR (125 MHz, CDCl3) d 21.79, 22.20, 52.20, 68.90, 69.17, 69.68, 117.86, 117.99, 118.88, 119.99, 124.93, 126.37, 126.72, 127.15, 128.71, 128.74, 128.87, 134.65, 135.42, 136.09, 138.11, 138.97, 149.89, 151.39, 152.08, 162.69, 163.61, 165.47; HRMS (FAB) Calcd for C32H35N6O7: 615.2567. Found 615.2570.

Methyl 5-{[(5-{[(5-amino-6-isopropoxy-2-pyridinyl)carbonyl]amino}-6-(benzyloxy)-2-pyridinyl)carbonyl]amino}-6-(benzyloxy)-2-pyridinecarboxylate (97e); 52% yield.

1H NMR (400 MHz, CDCl3) d 1.09 (d, J=6.0 Hz, 6H), 3.96 (s, 3H), 4.22 (s, 2H), 4.82 (m, 1H), 5.05 (s, 2H), 5.55 (s, 2H), 6.86 (d, J=7.6 Hz, 1H), 7.01 (t, J=7.2 Hz, 1H), 7.09 (t, J=7.2 Hz, 2H), 7.30 (m, 2H), 7.40 (m, 5H), 7.67 (d, J=8.0 Hz, 1H), 7.84 (d, J=8.4 Hz, 1H), 7.93 (d, J=8.0 Hz, 1H), 8.96 (d, J=8.0 Hz, 1H), 9.04 (d, J=8.0 Hz, 1H), 10.04 (s, 1H), 10.25 (s, 1H); 13C NMR (125 MHz, CDCl3) d 21.70, 52.45, 68.51, 68.96, 68.97, 117.72, 117.87, 118.61, 120.66, 125.27, 125.92, 125.93, 126.47, 127.01, 128.25, 128.39, 128.52, 128.74, 129.18, 134.18, 135.31, 135.97, 136.04, 137.67, 138.50, 149.62, 151.13, 152.29, 162.77, 163.55, 165.30; HRMS (FAB) Calcd for C36H35N6O7: 663.2567. Found 663.2569.

General Procedure for Coupling Aryl Acid Chlorides (95) and Aryl Amines (94 and 96a) to Yield Dimer (96) and Trimer Structures.

The aryl carboxylic acid (0.44 mmol), (COCl)2 (8.8 mmol, 20 eqv), and DMF (cat.) were dissolved in 5 ml of CH2Cl2. The solution was allowed to stir for 2 h at rt and was then concentrated in vacuo. A solution of the aryl amine (0.44 mmol, 1.0 eqv) and DIEA (1.33 mmol, 3.0 eqv) in 5 ml of CH2Cl2 was added to the crude acid chloride. The solution was stirred for 12 h at rt and was then concentrated in vacuo. Column chromatography [Hexanes/EtOAc (2/1)] yielded the arylamide as a white/yellow solid.

Methyl 6-methoxy-5-{1[(6-methoxy-5-nitro-2-pyridinyl)carbonyl]amino}-2-pyridinecarboxylate; 98% yield.

1H NMR (400 MHz, CDCl3) d 3.97 (s, 3H), 4.18 (s, 3H), 4.28 (s, 3H), 7.85 (d, J=8.0 Hz, 1H), 8.01 (d, J=8.4 Hz, 1H), 8.46 (d, J=8.0 Hz, 1H), 8.86 (d, J=8.0 Hz, 1H), 10.37 (s, 1H); 13C NMR (125 MHz, CDCl3) d 52.57, 54.53, 54.95, 115.70, 120.43, 125.54, 125.57, 136.36, 136.92, 139.04, 149.80, 152.90, 155.51, 160.44, 165.16; HRMS (EI) Calcd for C15H14N4O7: 362.0862. Found 362.0854.

Methyl 6-isopropoxy-5-{[(6-isopropoxy-5-nitro-2-pyridinyl)carbonyl]amino}-2-pyridinecarboxylate; 76% yield.

1H NMR (400 MHz, CDCl3) d 1.44 (d, J=6.0 Hz, 6H), 1.53 (d, J=6.0 Hz, 6H), 3.95 (s, 3H), 5.67 (m, 1H), 7.80 (d, J=8.0 Hz, 1H), 7.96 (d, J=8.0 Hz, 1H), 8.38 (d, J=8.4 Hz, 1H), 8.89 (d, J=8.0 Hz, 1H), 10.22 (s, 1H); 13C NMR (125 MHz, CDCl3) d 21.82, 22.14, 52.46, 69.76, 71.70, 115.10, 119.81, 125.65, 125.65, 136.53, 136.79, 138.99, 149.71, 152.06, 154.73, 160.71, 165.28; HRMS (FAB) Calcd for C19H23N4O7: 419.1567. Found 419.1569.

Methyl 6-(benzyloxy)-5-{[(6-(benzyloxy)-5-nitro-2-pyridinyl)carbonyl]amino}-2-pyridinecarboxylate; 82% yield.

1H NMR (400 MHz, CDCl3) d 4.04 (s, 3H), 5.17 (s, 2H), 5.65 (s, 2H), 7.28 (m, 5H), 7.36 (m, 3H), 7.51 (d, J=7.2 Hz, 2H), 7.93 (d, J=8.4 Hz, 1H), 8.01 (d, J=8.0 Hz, 1H), 8.43 (d, J=7.6 Hz, 1H), 8.97 (d, J=8.4 Hz, 1H), 10.30 (s, 1H); 13C NMR (125 MHz, CDCl3) d 52.56, 69.16, 69.35, 115.74, 120.50, 125.46, 125.91, 128.15, 128.44, 128.45, 128.62, 128.63, 128.94, 134.82, 135.78, 136.48, 136.71, 138.88, 149.45, 152.42, 154.69, 160.48, 165.05; HRMS (FAB) Calcd for C27H23N4O7: 515.1567. Found 515.1567.

Methyl 5-({[(6-(benzyloxy)-5-nitro-2-pyridinyl]carbonyl}amino)-6-isopropoxy-2-pyridinecarboxylate; 78% yield.

1H NMR (400 MHz, CDCl3) d 1.44 (d, J=6.0 Hz, 6H), 3.95 (s, 3H), 5.65 (m, 1H), 5.70 (s, 2H), 7.42 (m, 3H), 7.55 (d, J=6.8 Hz, 2H), 7.81 (d, J=8.0 Hz, 1H), 8.01 (d, J=8.0 Hz, 1H), 8.45 (d, J=8.0 Hz, 1H), 8.88 (d, J=8.0 Hz, 1H), 10.35 (s, 1H); 13C NMR (125 MHz, CDCl3) d 22.22, 52.46, 69.48, 70.03, 115.91, 119.79, 125.55, 125.56, 127.84, 128.66, 128.80, 134.68, 136.42, 136.89, 139.03, 149.75, 152.04, 154.84, 160.37, 165.22; HRMS (FAB) Calcd for C23H23N4O7: 467.1566. Found 467.1566.

Methyl 6-methoxy-5-{[(6-methoxy-5-{[(6-methoxy-5-nitro-2-pyridinyl)carbonyl]amino}-2-pyridinyl)carbonyl]amino}-2-pyridinecarboxylate; 97% yield.

1H NMR (400 MHz, CDCl3, 50ø C.) d 3.96 (s, 3H), 4.19 (s, 3H), 4.25 (s, 3H), 4.30 (s, 3H), 7.84 (d, J=8.4 Hz, 1H), 8.02 (dd, J1=8.0 Hz, J2=7.6 Hz, 2H), 8.44 (d, J=7.6 Hz, 1H), 8.89 (d, J=8.4 Hz, 1H), 8.98 (d, J=8.0 Hz, 1H), 10.31 (s, 1H), 10.36 (s, 1H); HRMS (EI) Calcd for C22H20N6O9: 512.1292. Found 512.1294.

Methyl 6-isopropoxy-5-{[(6-isopropoxy-5-{[(6-isopropoxy-5-nitro-2-pyridinyl)carbonyl]amino}-2-pyridinyl)carbonyl]amino}-2-pyridinecarboxylate; 79% yield.

1H NMR (500 MHz, CDCl3) d 1.45 (d, J=6.0 Hz, 6H), 1.53 (d, J=6.5 Hz, 6H), 1.55 (d, J=6.5 Hz, 6H), 3.95 (s, 3H), 5.69 (m, 1H), 7.80 (d, J=8.0 Hz, 1H), 7.98 (dd, J1=8.0 Hz, J2=8.0 Hz, 2H), 8.39 (d, J=8.0 Hz, 1H), 8.92 (d, J=8.0 Hz, 1H), 9.02 (d, J=8.5 Hz, 1H), 10.21 (s, 1H), 10.27 (s, 1H); 13C NMR (125 MHz, CDCl3) d 21.86, 22.19, 22.19, 52.34, 69.44, 69.76, 71.68, 115.23, 117.24, 120.01, 125.17, 125.83, 126.45, 126.85, 136.57, 136.87, 138.14, 140.39, 149.61, 151.06, 151.96, 154.74, 160.62, 162.51, 165.44; HRMS (FAB) Calcd for C28H33N6O9: 597.2309. Found 597.2312.

Methyl 6-(benzyloxy)-5-{[(6-(benzyloxy)-5-{[(6-(benzyloxy)-5-nitro-2-pyridinyl)carbonyl]amino}-2-pyridinyl)carbonyl]amino}-2-pyridinecarboxylate; 69% yield.

1H NMR (400 MHz, CDCl3) d 3.96 (s, 3H), 5.09 (s, 3H), 5.56 (s, 2H), 6.97 (t, J=7.6 Hz, 1H), 7.07 (t, J=7.6 Hz, 2H), 7.85 (d, J=8.0 Hz, 1H), 7.95 (d, J=8.0 Hz, 1H), 8.01 (d, J=8.0 Hz, 1H), 8.34 (d, J=8.0 Hz, 1H), 8.97 (d, J=8.4 Hz, 1H), 9.00 (d, J=8.0 Hz, 1H), 10.11 (s, 1H), 10.23 (s, 1H); 13C NMR (125 MHz, CDCl3) d 52.41, 69.15, 69.20, 69.25, 115.90, 117.88, 120.67, 125.54, 125.72, 126.34, 127.06, 128.36, 128.36, 128.48, 128.56, 128.58, 128.67, 128.81, 128.90, 129.20, 134.96, 135.42, 136.19, 136.31, 136.74, 136.62, 138.23, 140.39, 149.50, 151.59, 152.44, 154.79, 160.47, 162.42, 165.28; HRMS (FAB) Calcd for C40H33N6O9: 741.2309. Found 741.2308.

Methyl 5-{[(6-(benzyloxy)-5-{[(6-isopropoxy-5-nitro-2-pyridinyl)carbonyl]amino}-2-pyridinyl)carbonyl]amino}-6-isopropoxy-2-pyridine carboxylate; 84% yield.

1H NMR (400 MHz, CDCl3) d 1.12 (d, J=6.0 Hz, 6H), 1.35 (d, J=6.4 Hz, 6H), 3.93 (s, 3H), 4.97 (m, 1H), 5.58 (m, 1H), 5.63 (s, 2H), 7.45 (m, 3H), 7.52 (m, 2H), 7.79 (d, J=8.0 Hz, 1H), 7.94 (d, J=8.0 Hz, 1H), 8.03 (d, J=8.0 Hz, 1H), 8.33 (d, J=8.0 Hz, 1H), 8.90 (d, J=8.0 Hz, 1H), 9.08 (d, J=8.0 Hz, 1H), 10.14 (s, 1H), 10.45 (s, 1H); 13C NMR (125 MHz, CDCl3) d 21.38, 22.16, 52.32, 69.26, 69.71, 72.26, 115.08, 117.79, 119.97, 124.94, 125.69, 126.40, 127.18, 128.84, 129.02, 129.06, 135.52, 136.31, 136.91, 138.23, 140.33, 149.39, 151.51, 151.99, 154.77, 160.76, 162.22, 165.40; HRMS (FAB) Calcd for C32H33N6O9: 645.2309. Found 645.2309.

Methyl 6-(benzyloxy)-5-{[(6-(benzyloxy)-5-{[(6-isopropoxy-5-nitro-2-pyridinyl)carbonyl]amino}-2-pyridinyl)carbonyl]amino}-2-pyridinecarboxylate; 79% yield.

1H NMR (400 MHz, CDCl3) d 1.15 (d, J=6.0 Hz, 6H), 3.97 (s, 3H), 4.96 (m, 1H), 5.10 (s, 2H), 5.56 (s, 2H), 7.02 (t, J=7.6 Hz, 1H), 7.09 (t, J=6.8 Hz, 2H), 7.31 (m, 2H), 7.42 (m, 5H), 7.84 (d, J=8.0 Hz, 1H), 7.91 (d, J=8.0 Hz, 1H), 7.99 (d, J=8.0 Hz, 1H), 8.29 (d, J=8.0 Hz, 1H), 8.96 (d, J=8.0 Hz, 1H), 9.03 (d, J=8.0 Hz, 1H), 10.01 (s, 1H), 10.24 (s, 1H); 13C NMR (125 MHz, CDCl3) d 21.44, 52.39, 68.96, 69.06, 72.21, 115.10, 117.83, 120.62, 125.53, 125.76, 126.31, 127.10, 128.30, 128.44, 128.74, 128.76, 128.89, 129.24, 135.72, 136.22, 136.94, 138.18, 140.24, 146.52, 149.40, 151.50, 152.39, 154.76, 160.76, 162.39, 165.23; HRMS (FAB) Calcd for C36H33N6O9: 693.2309. Found 693.2308.

5-{[(5-{1[(5-amino-6-isopropoxy-2-pyridinyl)carbonyl]amino}-6-isopropoxy-2-pyridinyl)carbonyl]amino}-6-isopropoxy-2-pyridinecarboxylic acid.

Methyl 5-{[(5-{[(5-amino-6-isopropoxy-2-pyridinyl)carbonyl]amino}-6-isopropoxy-2-pyridinyl)carbonyl]amino}-6-isopropoxy-2-pyridinecarboxylate (6-1b) (15.0 mg, 0.026 mmol) was dissolved in 3 ml of dioxane. NaOH (0.15 ml of a 1 N solution) was added and the resulting mixture was stirred for 20 h at rt. The reaction was acidified with 1N HCl to pH 1.0 and then extracted with CH2Cl2. The organic fractions were combined, dried (MgSO4), filtered, and concentrated in vacuo. The crude product was washed several times with hexanes to yield 11.2 mg of a white solid (78%): 1H NMR (500 MHz, CDCl3) d 1.49 (d, J=6.0 Hz, 6H), 1.50 (d, J=6.5 Hz, 6H), 1.53 (d, J=6.5 Hz, 6H), 5.48 (m, 1H), 5.54 (m, 1H), 5.65 (m, 1H), 6.99 (d, J=8.0 Hz, 1H), 7.76 (d, J=8.0 Hz, 1H), 7.93 (d, J=8.0 Hz, 1H), 7.95 (d, J=8.0 Hz, 1H), 9.04 (d, J=8.0 Hz, 1H), 9.08 (d, J=8.0 Hz, 1H), 10.25 (s, 1H), 10.30 (s, 1H); 13C NMR (125 MHz, CDCl3) d 22.08, 22.17, 22.20, 68.59, 69.25, 70.30, 117.62, 117.90, 118.92, 120.04, 125.87, 126.37, 127.43, 128.02, 134.61, 135.57, 138.07, 138.49, 149.72, 150.86, 151.14, 162.91, 163.49, 163.72; HRMS (FAB) Calcd for C27H33N6O7: 553.2411. Found 553.2411.

Methyl 5-{[(5-{[(5-{[(5-amino-6-isopropoxy-2-pyridinyl)carbonyl]amino}-6-isopropoxy-2-pyridinyl)carbonyl]amino}-6-isopropoxy-2-pyridinyl)carbonyl]amino}-6-isopropoxy-2-pyridinecarboxylate.

6-Isopropoxy-5-nitro-2-pyridinecarboxylic acid (24.0 mg, 0.105 mmol), (COCl)2 (0.268 g, 2.12 mmol, 20 eqv), and DMF (cat.) were dissolved in 3 ml of CH2Cl2. The solution was allowed to stir for 2 h at rt and was then concentrated in vacuo. A solution of Methyl 5-{[(5-{[(5-amino-6-isopropoxy-2-pyridinyl)carbonyl]amino}-6-isopropoxy-2-pyridinyl)carbonyl]amino}-6-isopropoxy-2-pyridinecarboxylate (6-1b) (30.0 mg, 0.052 mmol, 0.5 eqv) and DIEA (27.3 mg, 0.21 mmol, 2.0 eqv) in 3 ml of CH2Cl2 was added to the crude acid chloride. The solution was stirred for 12 h at rt. The precipitate was filtered, and washed several times with cold CH2Cl2. The nitro-derivative and 10% Pd/C (5 mg) were added to 5 ml of 1:1 MeOH/CH2Cl2 and the suspension was stirred for 20 min at rt under 1 atm H2. The solution was filtered through celite and the filtrate was concentrated in vacuo to give 36 mg of a white solid (92%): 1H NMR (500 MHz, CDCl3) d 1.45 (d, J=6.5 Hz, 6H), 1.50 (d, J=6.5 Hz, 6H), 1.54 (d, J=6.0 Hz, 12H), 3.94 (s, 3H), 5.55 (m, 1H), 5.68 (m, 3H), 7.00 (d, J=7.5 Hz, 1H), 7.75 (d, J=8.0 Hz, 1H), 7.79 (d, J=8.0 Hz, 1H), 7.94 (d, J=8.0 Hz, 2H), 8.92 (d, J=8.0 Hz, 1H), 9.03 (dd, J1=8.0 Hz, J2=8.0 Hz 2H), 10.24 (s, 1H), 10.27 (s, 1H), 10.28 (s, 1H); 13C NMR (125 MHz, CDCl3) d 22.17, 22.17, 22.20, 22.20, 52.35, 68.56, 69.23, 69.33, 69.36, 117.32, 117.42, 117.86, 119.03, 120.02, 125.03, 125.83, 126.12, 126.63, 126.81, 127.25, 134.52, 135.33, 137.88, 138.71, 139.22, 149.67, 150.81, 150.87, 151.93, 162.78, 162.80, 163.46, 165.47; HRMS (FAB) Submitted.

Biological Data

The helix mimetic molecules described in this application show chemical and biological properties that are analogous to those of natural a-helix peptides. Three biological targets were assessed for inhibition properties against different classes of helix mimics.

Calmodulin and its Phosphodiesterase Activativating Properties.

Figure 12:
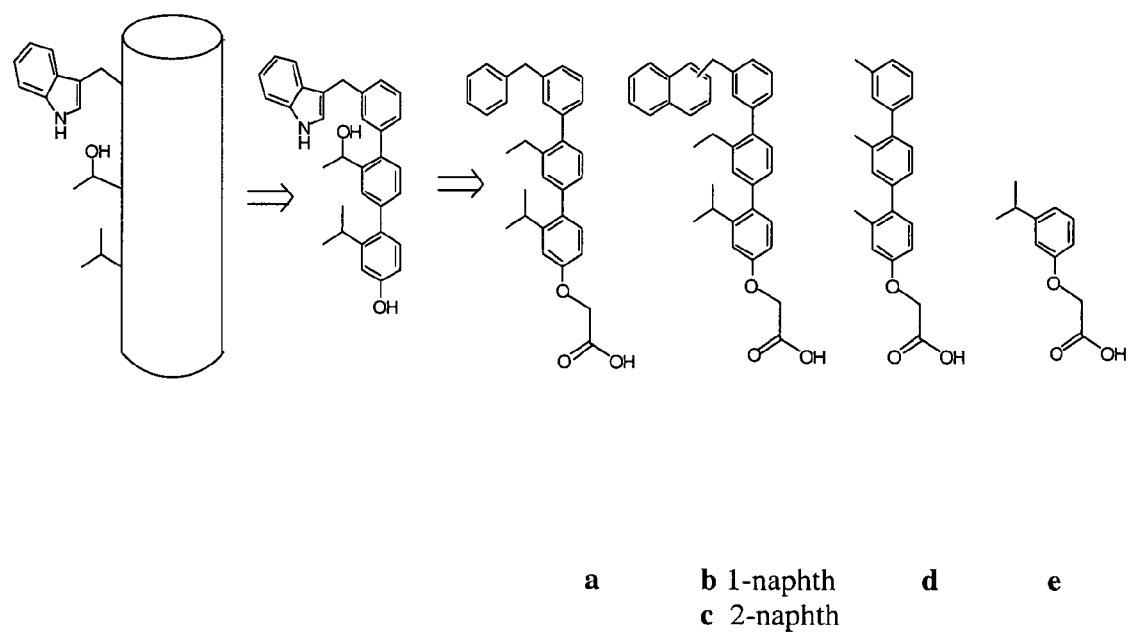
FIG. 12 represents shows the design of a number of compounds according to the present invention using as a template the RS20 20 mer peptide of smMLCK. Four proteomimetic compounds according to the present invention are set forth in FIG. 12.

To test the idea of α-helix mimicry by terphenyl derivatives, we focussed on the interaction between calmodulin (CaM) and an α-helical domain of smooth muscle myosin light chain kinase (smMLCK).[16] CaM also represents an interesting target in our continuing search[17] for molecules that influence cell cycle events.[18] Moreover, earlier work from DeGrado has shown that CaM provides an effective recognition surface for a variety of peptides in an α-helical conformation.[19] The sequence of a 20-mer fragment (RS20) in smMLCK is shown in FIG. 12 and mutational studies have established a key role for three i, i+3 and i+7 residues (Trp800, Thr803, and Val807) in binding to the C-terminal domain of CaM in a complex that also involves the collapsed N-terminal region.[20] The hydrophobic side chains of this key trio of residues can be mimicked by the corresponding 3,2',2''-terphenyl a which, in a staggered conformation, should project them with a similar rise and angle to that in smMLCK. For synthetic simplicity we changed the indole of Trp800 to phenyl and removed the hydroxyl of Thr803. Using Negishi couplings of differently substituted phenyltriflates, we prepared terphenyl a as a mimic of the calmodulin binding face of smMLCK. The free hydroxyl at the end of the iterative terphenyl synthesis was alkylated with benzyl bromoacetate, the ester was hydrolyzed and the resulting carboxylic acid was converted to the ammonium salt of a, which proved to be surprisingly soluble in buffer with <1% DMSO. FIG. 12 shows a number of the derivatives synthesized and utilized in this assay.

Figure 13:
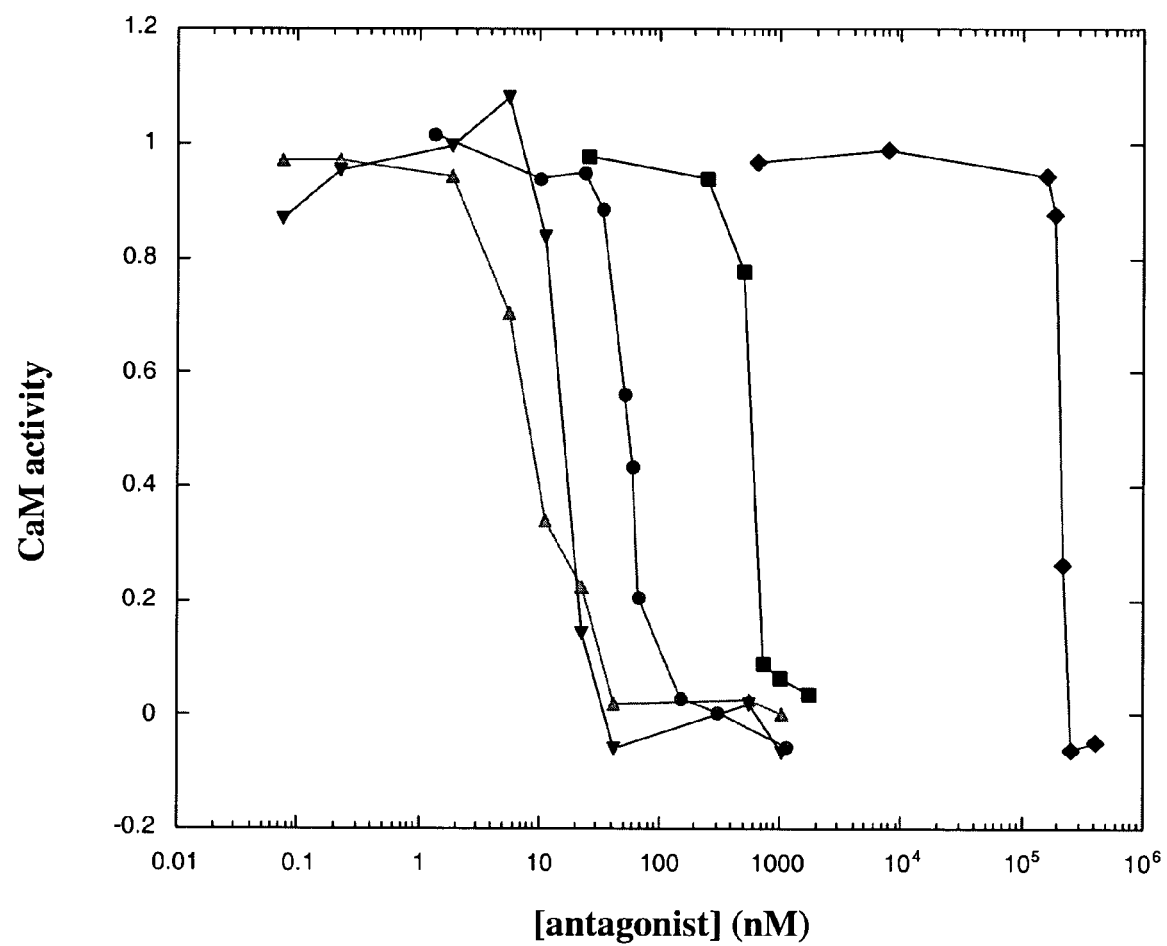
FIG. 13 shows the results of an experiment wherein the antagonism of CaM was monitored by phosphodiesterase hydrolysis of mant-cGMP for the compounds which are set forth in FIG. 12. The following legend applies to FIG. 13 ♦=d, ■=a, ●=RS-20, ▼=b ▲=c. 13.9 nM CaM, 50 mu/ml PDE, 8 μM mant-cGMP, 10 mM Mops, 0.5 mM MgCl$_2$, 90 mM KCl, 0.73 mM CaCl$_2$, 0.2% DMSO, pH 7.0.

Passage of a through an avidin based affinity resin derivatized with biotinylated CaM led to retention of the terphenyl on the column. Discrete complex formation to CaM was indicated by the release of a from the column, as monitored by HPLC, on elution with 5M biotin. The control experiment with an underivatized avidin resin resulted in no observable retention of a. In addition, polyacrylamide gel permeation chromatography (6 kD cutoff) showed that 2 alone (70 μM in buffer) was retained on the column but passed through when mixed with one equivalent of CaM, due presumably to the formation of a CaM:a complex. To amplify the binding event between CaM and a, an enzymatic assay was also employed. CaM activates the enzyme 3'-5' cyclic nucleotide phosphodiesterase (PDE) through an interaction that is thought to involve the same hydrophobic region that binds to smMLCK.[21] Addition of a to a solution of CaM and PDE caused a dose-dependant reduction in the ability of CaM to activate the enzyme for the hydrolysis of substrate (FIG. 13).[22] The inhibitory potency of a ($IC_{50}$=800 nM) in this PDE assay is only 10-fold less than the 20-mer α-helical peptide RS20 ($IC_{50}$=80 nM) and much stronger than the trimethylterphenyl d ($IC_{50}$>20 μM)[23] that lacks the trio of binding substituents or monophenyl e ($IC_{50}$=150 μM). This result suggests that a acts as a functional mimic of a natural CaM substrate by antagonizing the binding interaction between CaM and PDE. FIG. 13 shows the antagonism of CaM by monitoring PDE hydrolysis of substrate in the presence of inhibitors.

1- and 2-naphthyl derivatives b and c as improved analogs of the Trp800 indole side chain in smMLCK. FIG. 13 shows that both b and c are very potent inhibitors of CaM activation of PDE enzyme activity with $IC_{50}$ values of 9 nM and 20 nM, respectively. For b this potency corresponds to an 8-fold improvement over the helical peptide RS20 from smMLCK and renders it among the most active CaM antagonists known. However, the full extent of helix mimicry by a, b, and c in terms of their precise conformations and modes of binding to CaM awaits high-resolution structures of these complexes.

gp41-Virus Fusion Protein

We have designed a proteomimetic of an α-helical 4-3 hydrophobic repeat that inhibits the assembly of a six helix bundle corresponding to the fusion-active conformation of gp41 protein.[24] This intra-protein surface disruption results in reduced levels of HIV-1 entry into host cells. The gp41 ectodomain contains a N-terminal glycine-rich fusion sequence, as well as two helical regions containing hydrophobic 4-3 heptad (abcdefg) repeats denoted as the N and C helical regions. Recent evidence has shown that upon binding target surface cell receptors gp41 undergoes a conformational change which exposes the hydrophobic N helix regions and allows the fusion peptides to insert into the host cell membrane. This transient gp41 intermediate then refolds into a stabilized six helix bundle structure, which brings both the viral and target cell membranes into proximity resulting in completion of the fusion process. The fusion-critical helix bundle has been shown by X-ray diffraction data to exist as a gp41 trimer in which the N helix regions form a parallel trimeric coiled-coil and the C helix regions subsequently pack in an antiparallel fashion into the hydrophobic grooves formed by the coiled-coil.

Antagonists that bind the exposed N helix regions of the transient gp41 intermediate can potentially trap this structure prior to bundle formation, leading to inhibition of viral fusion.[25] Peptides with sequences corresponding to the C helix region of gp41 are potent inhibitors of HIV fusion, one of which is currently in human trials.[26] Small molecules that bind into a hydrophobic pocket in the N helix trimer inhibit viral fusion in vitro, with activities in the low micromolar range.[27] However, other sites along the hydrophobic grooves of the N helix trimer are also important for C helix recognition,[28] as evidenced by the strong binding of C-terminal peptides that lack the key Trp residues ($W_{628}$ and $W_{631}$ in gp41). Also, small peptides corresponding to the pocket binding region have negligible viral fusion inhibition and mutations of C peptide residues distant from the $W_{628}$ and $W_{631}$ binding region abolish inhibition activity.[29]

Figure 14:
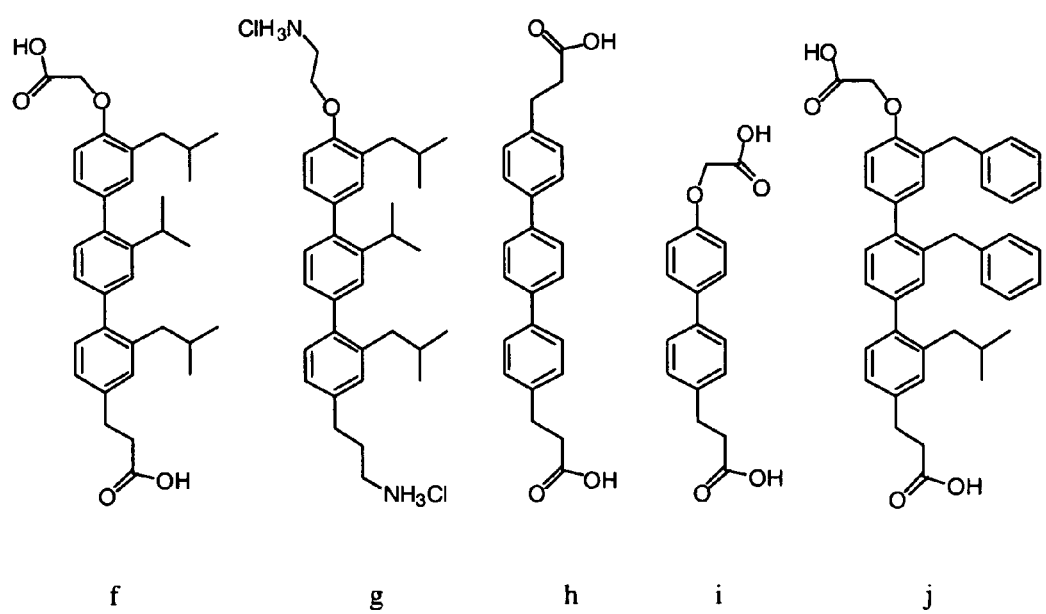
FIG. 14 shows a number of exemplary inhibitors of gp-41 disruption (HIV).

Tris-functionalized 3,2',2''-terphenyl derivatives serve as effective mimics of the surface functionality projected along one face of an α-helix. To target the gp41 complex we prepared terphenyl derivative f, which mimics the side chains of a i, i+4, i+7 dad hydrophobic surface as found in the C and N heptad repeat regions. Although there are a range of hydrophobic residues at the a and d positions, Leu and Ile are the most prevalent. Therefore, we have incorporated related branched alkyl substituents, isobutyl and isopropyl (to avoid complications from chirality in sec-butyl group), into our initial design. Terminal carboxylate groups were also added to mimic the anionic character of the C peptide helix and to improve the aqueous solubility. A number of these compounds are presented in attached FIG. 14.

Figure 15:
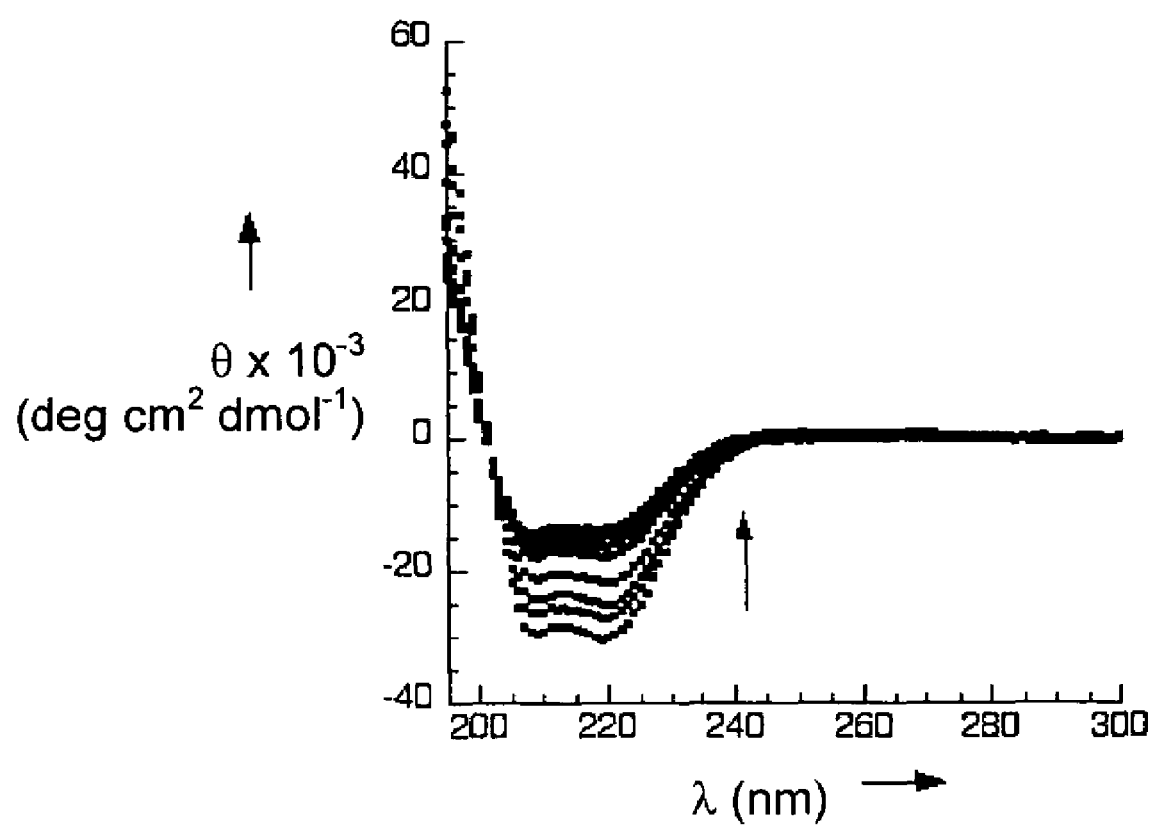
FIG. 15 shows the CD spectra of a 10 μM solution (50 mM PBS, 150 mM NaCl, pH 7.0, 4° C.) of the gp41 core model upon titration of f (0-50 μM). The arrow indicates the reduction in signal at θ222 and 208 nm.
Figure 16:
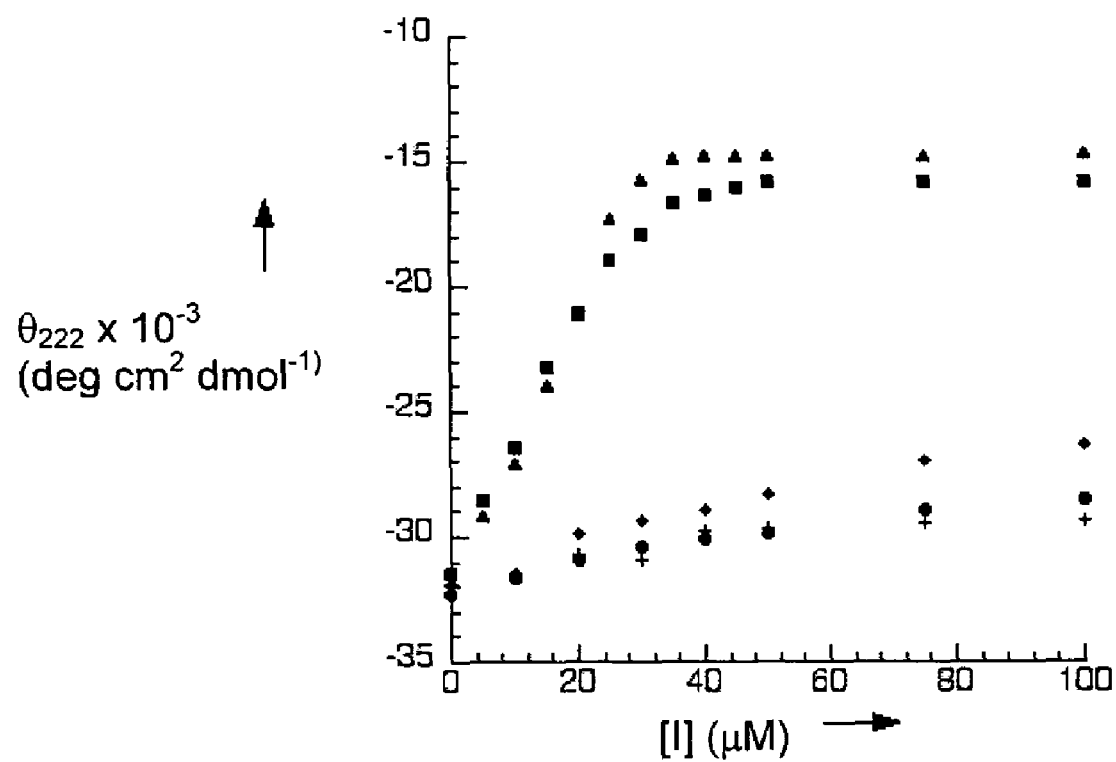
FIG. 16 shows the CD signal at θ222 nm versus inhibitor concentration: f (■); g (♦); h (●); i (+); j (▲). The inhibitors were titrated into a 10 μM aqueous solution of the gp41 model complex (50 mM PBS, 150 mM NaCl, pH 7.0, 4° C.).

The ability of f to influence the disruption of the gp41 core was studied using CD spectroscopy. A model system composed of two peptides (N36 and C34), from the N and C heptad repeat regions of gp41, forms a stable six helix bundle ($T_m$=66° C.) that is analogous to the gp41 core. CD experiments show that the C34 peptide alone in solution is random coil and the N36 peptide forms concentration dependent aggregates. Titration of f into a 10 μM solution (50 mM PBS, 150 mM NaCl, pH 7.0, 4° C.) of the preformed gp41 core model resulted in a decrease of the CD signal at Θ222 and 208 nm, corresponding to a reduction in the helicity of the hexameric bundle. A plot of Θ222 versus inhibitor concentration (FIG. 15) shows saturation at approximately three equivalents of f. The CD spectrum with excess f was similar to the theoretical addition of the individual N36 and C34 spectra at the same concentration. Both the hydrophobic and electrostatic features of f are important for its ability to disrupt the bundle. Analogs h and i, lacking the key alkyl side chains and analog g with positively charged substituents on the hydrophobic core have little effect on the protein CD spectrum even at high concentrations (FIG. 16). To test the scope of this strategy we have increased the size of the hydrophobic substituents in f, using the bis-benzyl substituted j. This molecule shows a modest enhancement in activity compared to f (FIG. 16), fully disrupting the hexameric bundle at a lower concentration. The disruption of the hexameric bundle seen in the CD experiments was supported by an ELISA for gp41 core disruption using an antibody that binds the N36/C34 helix bundle but not the individual peptides. Mimetic f effectively disrupts N36/C34 complexation with an $IC_{50}$ of 13.18±2.54 μg/ml in comparison to g-i which have no effect at 100 μg/ml.

Finally, the effects of antagonist f on HIV-1 mediated fusion were studied using a dye transfer cell fusion assay.[30] If the gp41 core is being disrupted, as implied by the CD and ELISA experiments, then the fusion mechanism of HIV-1 should be inhibited. Indeed, f shows inhibition of HIV-1 mediated cell-to-cell fusion with an $IC_{50}$ of 15.70±1.30 μg/. In comparison, compounds g-i had no inhibitory activity and proved to be cytotoxic at similar concentrations.

BcLxL/Bak Complex in Apoptosis

To further extend this strategy we tried to mimic parts of the α-helical, pro-apoptotic Bak- and Bad-proteins, which interact by heterodimerizatibn with the anti-apoptotic protein Bcl-$x_L$. Bcl-$x_L$ is overexpressed in many types of cancer and protects transformed cells from cell death, leading to uncontrolled cell growth even if apoptotic signals generated by chemo- or radiotherapy are present. A designed Bak/Bad-mimetic could interact with the anti-apoptotic BCl-$x_L$ protein and thus enable the apoptotic cascade leading to cell death. We based our design on the crystal and solution structures of BCl-$x_L$, which show the helical Bak-peptide binding into a hydrophobic cleft formed by the BH1-BH3 domains of BCl-$x_L$. From alanine scans of the Bak-peptide it is clear that four hydrophobic residues (Val[74], Leu[78], Ile[81], Ile[85]) along one edge of the helix are involved in binding. In addition, Asp[83] forms an ion pair with a lysine residue of BCl-$x_L$. A related 26-mer peptide derived from the Bad-protein binds better to BCl-$x_L$, exploiting larger hydrophobic residues (Tyr, Phe) to induce a slight structural change in the binding region of Bcl-$x_L$.

Figure 17:
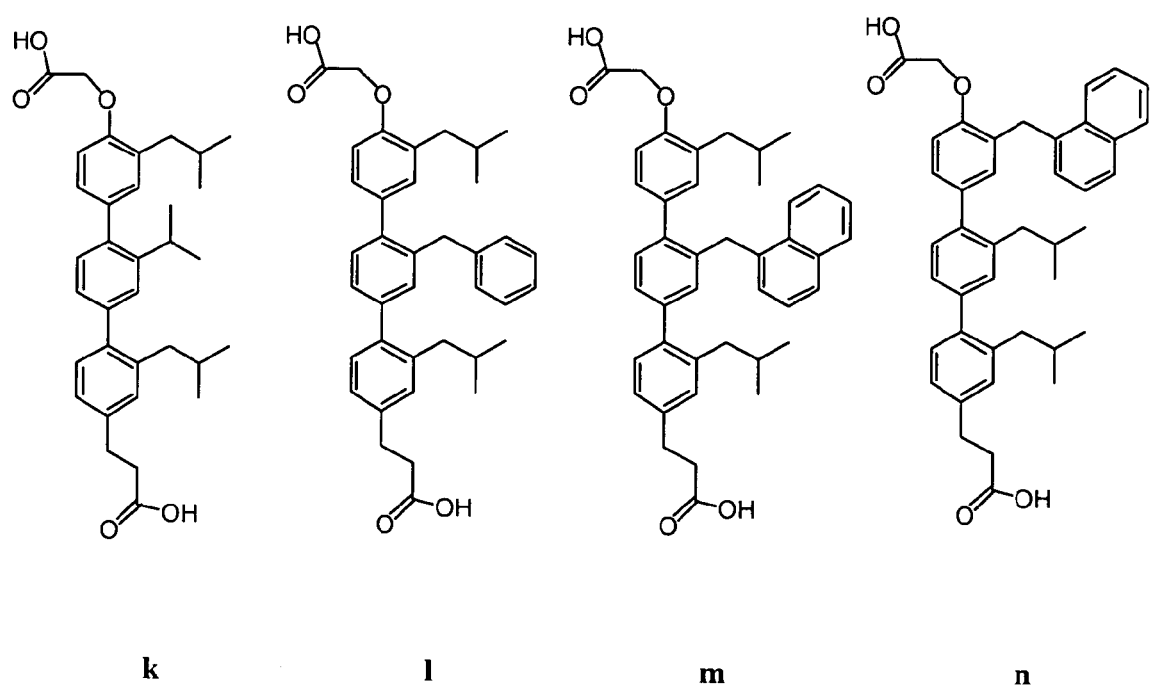
FIG. 17 shows a number of proteomimetic compounds for Bcl-x$_L$.
Figure 18:
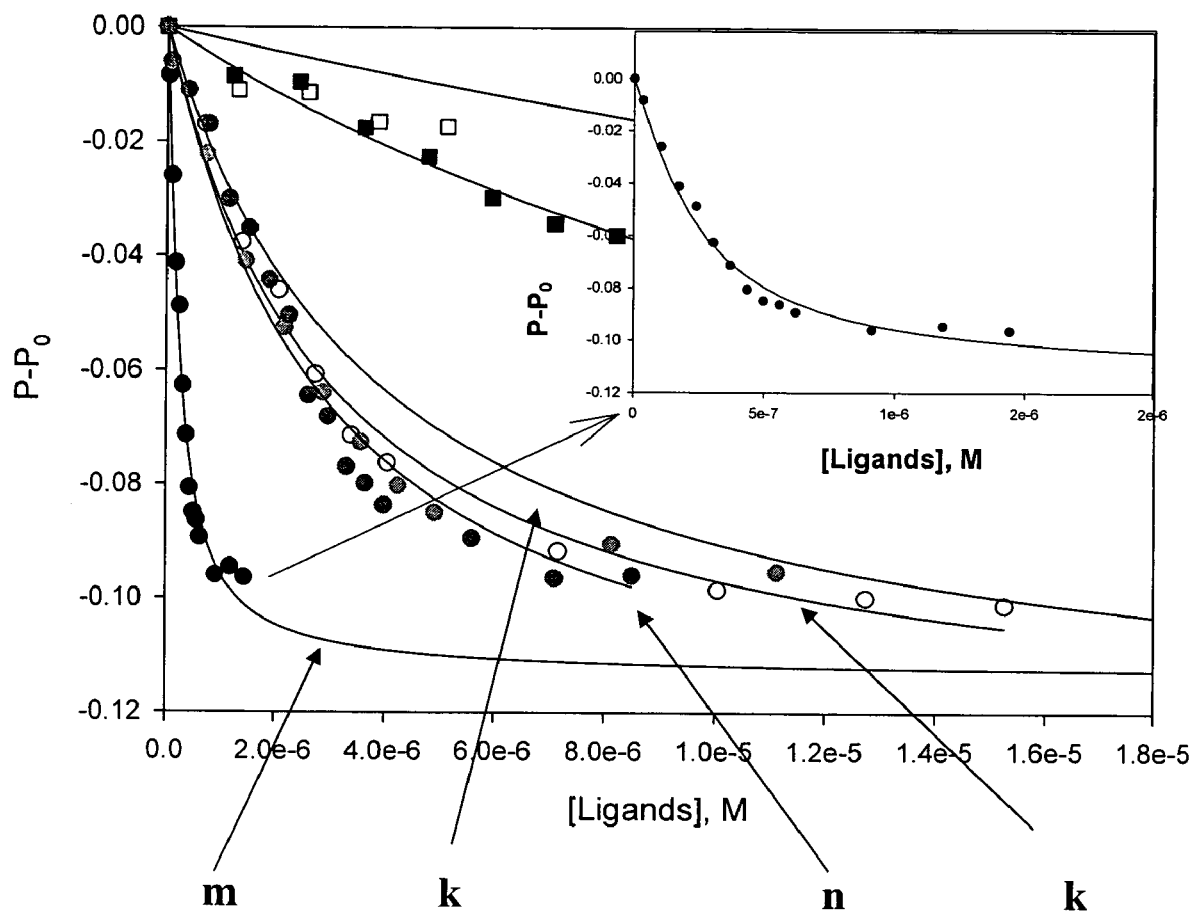
FIG. 18 shows the results of an assay system using the compounds presented in FIG. 17. The figure exhibits the results of fluorescence polarization experiments measuring the displacement of fluorescein labelled Bak peptide from BcLxL.

Based on these structural requirements we designed a series of terphenyl molecules (k-n) containing alkyl or aryl substituents on the three ortho positions (to mimic the key i, i+3, and i+7 groups in Bak or Bad) and carboxylic acid substituents on either end (to mimic the additional ion pair) (FIG. 17). The binding affinity of these molecules for Bcl-$x_L$ was assessed by a fluorescence polarization assay using fluoresceine-labeled 16-mer Bak-peptide. Displacement of this probe through competitive binding of the terphenyl into the hydrophobic cleft of BCl-$x_L$ would lead to a decrease in its fluorescence polarization which in turn could be related to the known affinity of the 16-mer Bak/Bcl-$x_L$ complex. This assay showed (FIG. 18) that the terphenyl molecule with two carboxylic acids and the isobutyl, 1-naphthalenemethylene, isobutyl sequence (m) shows the strongest binding to Bcl-$x_L$ with a $K_D$-value of 114 nM, whereas less hydrophobic terphenyls with only alkyl side chains (k) or with one benzyl side chain (l) show less binding affinity, emphasizing the importance of hydrophobic interactions for binding to the hydrophobic cleft in Bcl-$x_L$. The analogue compound n with the naphthalenemethylene side chain at the top phenyl unit shows a significant loss in binding affinity indicating the importance of the relative positions of the terphenyl side chains.

It is to be understood by those skilled in the art that the foregoing description and examples are illustrative of practicing the present invention, but are in no way limiting. Variations of the detail presented herein may be made without departing from the spirit and scope of the present invention as defined by the following claims.

References

1. Andrews, M. J. I.; Tabor, A. B. *Tetrahedron* 1999, 55, 11711-11743.
2. Smith, A. B; Knight, S. D.; Sprengeler, P. A.; Hirschmann, R. *Bioorg. Med. Chem.* 1996, 4, 1021-1034. Abbenante, G.; March, D. R.; Bergman, D. A.; Hunt, P. A.; Garnham, B.; Dancer, R. J.; Martin, J. L.; Fairlie, D. P. *J Am. Chem. Soc.* 1995, 117, 10220.
3. See, for example, Sasaki, T.; Lieberman, M. "Protein Mimetics" in *Comprehensive Supramolecular Chemistry*, Vol. 4, Murakami, Y. Ed. Pergamon Press, Oxford, 1996, pp193-242.
4. See Park, H. S.; Lin, Q.; Hamilton, A. D. *J. Am. Chem. Soc.* 1999, 121, 8-13.
5. For recent exceptions see; O'Donnell, M.; Garippa, R. J.; O'Neill, N. C.; Bolin, D. R.; Cotrell, J. M. *J. Biol. Chem.* 991, 266, 6389-6392. Nolan, W. P.; Ratcliffe, G. S.; Rees, D. C. *Tet. Lett.* 1992, 33, 6879-6882. Xuereb, H.; Maletic, M.; Gildersleeve, J.; Pelczer, I.; Kahne, D. *J. Am. Chem. Soc.* 2000, 122, 1883-1890.
6. For a recent review see; Fairlie, D. P.; West, M. L.; Wong, A. K. *Curr. Med. Chem.* 1998, 5, 29-62.
7. Jackson, D. Y.; King, D. S.; Chmielewski, J.; Singh, S.; Schultz, P. G. *J. Am. Chem. Soc.* 1991, 113, 9391-9392. Ruan, F.; Chen, Y.; Hopkins, P. B. *J. Am. Chem. Soc.* 1990,112, 9403-9404. Ghadiri, M. R.; Choi, C. *J. Am. Chem. Soc.* 1990, 112, 1630-1632. Öspay, G.; Taylor, J. W. *J. Am. Chem. Soc.* 1992,114, 6966-6973. Albert, J. S.; Hamilton, A. D. *Biochemistry*, 1995, 34, 984-990. Merutka, G.; Stellwagen, E. *Biochemistry* 1991, 30, 1591-1594.
8. Kemp, D. S.; Allen, T. J.; Oslick, S. L.; Boyd, J. G. *J. Am. Chem. Soc.* 1996, 118, 4240. Austin, R. E.; Maplestone, R. A.; Sefler, A. M.; Lui, K.; Hruzewicz, W. N.; Lui, C. W.; Cho, H. S.; Wemmer, D. E.; Bartlett, P. A. *J. Am. Chem. Soc.* 1997, 119, 6461. Müller, K.; Obrecht, D.; Knierzinger, A.; Stankovic, C.; Spiegler, C.; Bannwarth, W.; Trzeciak, A.; Englert, G.; Labhardt, A. M.; Schönholzer, P. in *Perspectives in Medicinal Chemistry*, Testa, B.; Kyburz, E.; Fuhrer, W.; Giger, R., Eds. 1993, pp 513-531, VCH Press, Weinheim.
9. Zondlo, N. J.; Schepartz, A. S., *J. Am. Chem. Soc.* 1999, 121, 6938-6939. Struthers, M. D.; Cheng, R. P.; Imperiali, B., *J. Am. Chem. Soc.* 1996, 118, 3073-3081.
10. Gellman, S. H. *Acc. Chem. Res.* 1998, 31, 173. Hinterman, T.; Gademann, K.; Jaun, B.; Seebach, D. *Helv. Chim. Acta*, 1998, 81, 983. Hamuro, Y.; Geib, S. J.; Hamilton, A. D., *J. Am. Chem. Soc.* 1997, 119, 10587-10593.
11. Peczuh, M. W.; Hamilton, A. D.; Sanchez-Quesada, J.; deMendoza, J.; Haack, T.; Giralt, E. *J. Am. Chem. Soc.* 1997, 119, 9327-9328.
12. Albert, J. S.; Peczuh, M. W.; Hamilton, A. D. *Bioorg. Med. Chem.* 1997, 5, 1455-1467.
13. For an example of 2,3'-disubstituted biphenyls as constrained turn mimics see; Nesloney, C. L.; Kelly, J. W. *J. Am. Chem. Soc.* 1996, 118, 5836-5845.
14. Using the MacroModel program, Still, W. C. Columbia University.
15. Stereoisomerism will occur if one of the rings rotates by 180°, however there should be rapid interconversion between the different forms with the optimum conformation being populated on binding to the target.
16. Meador, W. E.; Means, A. R.; Quicho, F. A. *Science* 1992, 257, 1251-1255.
17. Sebti, S. M.; Hamilton, A. D. *Methods in Enzymology*, 2000, 325, 381-388.
18. Taulés, M.; Rius, E.; Talaya, D.; López-Girona, A.; Bachs, O.; Agell, N. *J. Biol. Chem.* 1998, 273, 33279-33286.
19. O'Neil, K. T.; DeGrado, W. F. *TIBS* 1990, 15, 59-64.
20. Meador, W. E.; Means, A. R.; Quiocho, F. A. *Science* 1992, 257, 1251-1255.
21. Yuan, T.; Walsh, M. P.; Sutherland, C.; Fabian, H.; Vogel, H. J. *Biochemistry*, 1999, 38, 1446-1455.
22. Johnson, J. D.; Walters, J. D.; Mills, J. S., *Anal. Biochem.*, 1987, 162, 291-295.
23. A precise $IC_{50}$ value could not be achieved due to poor solubility above 20 μM.
24a) D. C. Chan, D. Fass, J. M. Berger, P. S. Kim, *Cell* 1997, 89, 263-273; b) M. Lu, P. S. Kim, *J. Bio. Mol. Struct. Dyn.* 1997, 15, 465-471.
25a) M. Lu, S. C. Blacklow, P. S. Kim, *Nat. Struct. Biol.* 1995, 2, 1075-1082; b) M. Ferrer, T. M. Kapoor, T. Strassmaier, W. Weissenhom, J. J. Skehel, D. Oprian, S. L. Shreiber, D. C. Wiley, S. C. Harrison, *Nat. Struct. Biol.* 1999, 6, 953-960.
26a) R. A. Furuta, C. T. Wild, Y. Weng, C. D. Weiss, *Nat. Struct. Biol.* 1998, 5, 276-279; B)J. M. Kilby, S. Hopkins, T. M. Venetta, B. DiMassimo, G. A. Cloud, J. Y. Lee, L. Alldredge, E. Hunter, D. Lambert, D. Bolognesi, T. Matthews, M. R. Johnson, M. A. Nowak, G. M. Shaw, M. S. Saag, *Nat. Med.* 1998, 4, 1302-1307.
27. S. Jiang, K. Lin, N. Strick, A. R. Neurath, *Biochem. Biophys. Res. Commun.*, 1993, 195, 533-538.
28 For the role of the Bcl-2 protein family in apoptosis see e.g.: (a) A. Gross, J. M. McDonnell, S. J. Korsmeyer, *Genes & Development* 1999, 13, 1899-1911. (b) D. T. Chao, S. J. Korsmeyer, *Annu. Rev. Immunol.* 1998, 16, 395-419.
29 structure reviews: (a) S. W. Fesik, *Cell* 2000, 103, 273-282. (b) H. Liang, S. W. Fesik, *J. Mol. Biol.* 1997, 274, 291-302.
30 M. Sattler, H. Liang, D. Nettesheim, R. P. Meadows, J. E. Harlan, M. Eberstadt, H. S. Yoon, S. B. Shuker, B. S. Chang, A. J. Minn, C. B. Thompson, S. W. Fesik, *Science* 1997, 275, 983-986.

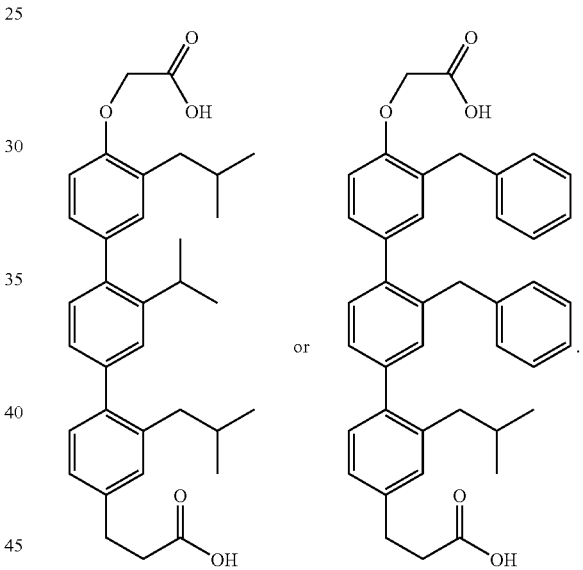

What is claimed is:

1. A method of inhibiting cellular invasion of HIV in an individual, said method comprising administering to said individual an effective amount of a compound of formula